(12) United States Patent
Aldrich et al.

(10) Patent No.: US 11,325,944 B2
(45) Date of Patent: May 10, 2022

(54) MACROCYCLIC PEPTIDES AND DERIVATIVES THEREOF WITH OPIOID ACTIVITY

(71) Applicant: University of Florida Research Foundation, Incorporated, Gainesville, FL (US)

(72) Inventors: Jane V. Aldrich, Gainesville, FL (US); Laura E. Hanold, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 253 days.

(21) Appl. No.: 16/622,749

(22) PCT Filed: Jun. 15, 2018

(86) PCT No.: PCT/US2018/037822
§ 371 (c)(1),
(2) Date: Dec. 13, 2019

(87) PCT Pub. No.: WO2018/232285
PCT Pub. Date: Dec. 20, 2018

(65) Prior Publication Data
US 2020/0109168 A1    Apr. 9, 2020

Related U.S. Application Data

(60) Provisional application No. 62/520,992, filed on Jun. 16, 2017.

(51) Int. Cl.
*C07K 5/12* (2006.01)
*A61K 38/07* (2006.01)
*A61K 38/12* (2006.01)
*A61K 38/00* (2006.01)

(52) U.S. Cl.
CPC .............. *C07K 5/126* (2013.01); *A61K 38/00* (2013.01)

(58) Field of Classification Search
None
See application file for complete search history.

(56) References Cited

U.S. PATENT DOCUMENTS

| | | |
|---|---|---|
| 6,399,568 B1 | 6/2002 | Nishino et al. |
| 8,809,278 B2 | 8/2014 | Aldrich et al. |
| 10,259,843 B2 | 4/2019 | Aldrich et al. |
| 2013/0108655 A1 | 5/2013 | Zabrocki et al. |
| 2020/0109168 A1 | 4/2020 | Aldrich et al. |
| 2021/0163532 A1 | 6/2021 | Aldrich et al. |

OTHER PUBLICATIONS

PCT/US2018/037822, Aug. 30, 2018, International Search Report and Written Opinion.
PCT/US2018/037822, Dec. 26, 2019, International Preliminary Report on Patentability.
PCT/US2019/027928, Oct. 29, 2020, International Preliminary Report on Patentability.

(Continued)

*Primary Examiner* — Kevin S Orwig
(74) *Attorney, Agent, or Firm* — Wolf, Greenfield & Sacks, P.C.

(57) ABSTRACT

The invention relates to macrocyclic peptides and pharmaceutical compositions thereof. The invention further relates to pharmaceutical compositions for modulating opioid receptor activity.

26 Claims, 7 Drawing Sheets

(56) References Cited

OTHER PUBLICATIONS

PCT/US2019/027928, Jun. 21, 2019, Invitation to Pay Additional Fees.
PCT/US2019/027928, Aug. 27, 2019, International Search Report and Written Opinion.
International Search Report and Written Opinion dated Aug. 30, 2018 for PCT/US2018/037822.
International Preliminary Report on Patentability dated Dec. 26, 2019 for PCT/US2018/037822.
International Preliminary Report on Patentability dated Oct. 29, 2020 for PCT/US2019/027928.
Invitation to Pay Additional Fees dated Jun. 21, 2019 for PCT/US2019/27928.
International Search Report and Written Opinion dated Aug. 27, 2019 for PCT/US2019/27928.
[No Author Listed], Amino Acids. Vanderbilt. 2009. Retrieved from https://www.vanderbilt.edu/AnS/Chemistry/Rizzo/Chem220b/aminoacids.pdf.
[No Author Listed], Pubmed Compound Summary for CID 102062033. (3R, 12S)-3-Benzyl-10-methyl-1,4,7,10-tetrazabicyclo[10.3.0]pentadecane-2,5,8,11-tetrone. U.S. National Library of Medicine. Accessed from <https://pubchem.ncbi.nlm.nih.gov/compound/102062033>. Dec. 24, 2015. 9 pages.
[No Author Listed], Pubmed Compound Summary for CID 118881148. (12R)-1,4,7,10-Tetrazabicyclo[10.3.0]pentadecane-2,5,8,11-tetrone. U.S. National Library of Medicine. Accessed from <https://pubchem.ncbi.nlm.nih.gov/compound/118881148>. Apr. 9, 2016. 9 pages.
[No Author Listed], Pubmed Compound Summary for CID 101684828. (3R,6R,12S)-3,6-Bis(sulfanylmethyl)-1,4,7,10-tetrazabicyclo[10.3.0]pentadecane-2,5,8,11-tetrone. U.S. National Library of Medicine. Accessed from <https://pubchem.ncbi.nlm.nih.gov/compound/101684828>. Dec. 18, 2015. 11 pages.
[No Author Listed] Biomolecule: Protein 1. Chempages Netorials. 2021.
Aldrich et al., Substitution of aromatic residues in the macrocyclic opioid peptide [D-Trp]CJ-15,208 alters the opioid activity profile in vivo. Proceedings 35$^{th}$ European Peptide Symposium. 2018;61-63.
Aldrich et al., The Macrocyclic Peptide Natural Product CJ-15,208 Is Orally Active and Prevents Reinstatement of Extinguished Cocaine-Seeking Behavior. Journal of Natural Products. Jan. 2013;76:433-8.
Dolle et al., Nascent structure-activity relationship study of a diastereomeric series of kappa opioid receptor antagonists derived from CJ-15,208. Bioorg Med Chem Lett. Jul. 1, 2009;19(13):3647-50. doi: 10.1016/j.bmcl.2009.04.105. Epub May 3, 2009. PMID: 19464172.
Jois et al., NMR and X-ray crystallographic studies on cyclic tetrapeptide, cyclo (D-Phe-Pro-Sar-Gly). Int J Pept Protein Res. Jul. 1996;48(1):12-20. doi: 10.1111/j.1399-3011.1996.tb01102.x. PMID: 8844259.
Lin et al., On-surface Cyclization of Tetrapeptides using Molecularly Imprinted Polymers as Non-covalent Auxiliaries. Journal of the Chinese Chemical Society. 2009;56(1):127-34.

$ED_{50}$(and 95% C.I.) value @ 20 min = 9.29 (6.91-13.2) nmol, i.c.v.

MACROCYCLIC PEPTIDES AND DERIVATIVES THEREOF WITH OPIOID ACTIVITY

CROSS-REFERENCE TO RELATED APPLICATIONS

This application is a National Stage filing under 35 U.S.C. 371 of International Application No. PCT/US2018/037822, filed Jun. 15, 2018, which claims priority to U.S. Provisional Application No. 62/520,992, filed Jun. 16, 2017, which applications are incorporated herein by reference in their entirety.

STATEMENT OF GOVERNMENT SUPPORT

This invention was made with government support under Grant Nos. DA023924 and DA018832 awarded by the National Institutes of Health; and Grant Nos. W81XWH-15-1-0452 and W81XWH-15-1-0464 awarded by U.S. Army Medical Research and Medical Materiel Command. The government has certain rights in the invention.

BACKGROUND

Opioid receptors belong to the Type A class of G-protein coupled receptors (GPCRs) and bind to opioid ligands. The three major types of opioid receptors are the delta (δ) opioid receptor (DOR), kappa (κ) opioid receptor (KOP), and mu (μ) opioid receptor (MOR). The nociceptin receptor (NOR) was later identified as a fourth major opioid receptor type, as it shares >60% sequence homology with the δ-, κ- and μ-receptors. The delta, kappa, and mu opioid receptors exhibit approximately 50% sequence similarity [Reisine, T. and Bell, G. I. (1993) Molecular biology of opioid receptors Trends Neurosci 16, 506-510]. Opioid receptors fulfill a variety of functions within the cell, including activation of ion channels, inhibition of neurotransmitter release, and inhibition of adenylyl cyclase to decrease intracellular levels of cAMP. The distinct anatomical distributions of each receptor contribute to their mediation of different behaviors [Corbett, A. D., Henderson, G., McKnight, A. T., and Paterson, S. J. (2006) 75 years of opioid research: the exciting but vain quest for the Holy Grail Br J Pharmacol 147, S 153-S 162]. Opioid receptors are widely distributed throughout the body and have distinct endogenous ligands.

Two closely related endogenous opioids were identified as the natural ligands of the opioid receptors. These endogenous opioids are referred to as pentapeptide enkephalins. All opioid peptides contain the sequence of either [Met]-enkephalin (e.g., YGGFM) or [Leu]-enkephalin (e.g., YGGFL). A 31 amino acid fragment of the pituitary hormone β-lipotropin, called β-endorphin, contains the sequence of [Met]-enkephalin at its amino-terminus and was discovered to be a potent opioid agonist. These peptide agonists vary in their affinity for each of the δ-, κ-, and μ-receptors and these peptides do not bind exclusively to one receptor type [Corbett, A. D., Patterson, S. J., and Kosterlitz, H. W. (1993) Selectivity of ligands for opioid receptors In: Handbook Exp Pharmacol 104/1 ed. Herz, A. 645-679 Berlin: Springer-Verlag; Henderson, G. and McKnight, A. T. (1997) The orphan opioid receptor and its endogenous ligand-nociceptin/orphanin FQ Trends Pharmacol Sci 18, 293-300].

The delta (δ) opioid receptor (DOR) has enkephalins as its endogenous ligands. The delta opioid receptor is found in the brain (e.g., in the pontine nuclei, amygdala, olfactory bulbs, and deep cortex) and in peripheral sensory neurons. In humans, the delta opioid receptor is most widely expressed in the basal ganglia and neocortical regions of the brain. Delta opioid receptors are distributed in brain regions associated with processes involved in the perception of pain, sensory information, emotional processing, and impulsivity, among others, indicating that DOR agonists and antagonists could be effective at treating a variety of indications, such as depression and other mood disorders, along with providing analgesic effects [Peppin, J. F. and Raffa, R. B. (2015) Delta opioid agonists: a concise update on potential therapeutic applications J Clin Pharm Ther 40, 155-166]. While the exact role of the DOR in pain modulation is debated, it has been suggested that the DOR modulates the nociception of chronic pain [Berrocoso, E., Sánchez-Blázquez, P., Garzón, J., and Mico, J. A. (2009) Opiates as antidepressants Curr Pharm Des 15, 1612-1622].

The mu (μ) opioid receptor (MOR) binds enkaphalins and beta-endorphin as endogenous ligands with high affinity. The mu opioid receptor is found in the brain (e.g., cortex, thalamus, striosomes, periaqueductal gray, and rostral ventromedial medulla), spinal cord (e.g., substantia gelatinosa), peripheral sensory neurons, and intestinal tract. Morphine is the original MOR agonist. Long-term or high-dose use of opioids can lead to the development of tolerance, including downregulation of MOR gene expression or the upregulation of glutamate pathways in the brain that exert an opioid-opposing effect to reduce the effect of opioids [Ueda, H. and Ueda, M. (2009) Mechanisms underlying morphine analgesic tolerance and dependence Front Biosci 14, 5260-5272].

The kappa (κ) opioid receptor (KOR) binds the opioid peptides, dynorphins, as the primary endogenous ligands. A variety of other natural alkaloids and terpenes can also bind to the kappa opioid receptor. The kappa opioid receptor is found in the brain (e.g., hypothalamus, periaqueductal gray, and claustrum), spinal cord (e.g., substantial gelatinosa), and peripheral sensory neurons. KOR agonists are involved in pain modulation, hallucinogenic or dissociative effects, and chronic stress (e.g., depression, anxiety, anhedonia, and increased drug-seeking behavior). KOR agonists have been investigated for their potential in the treatment of addiction [Hasebe, K., Kawai, K., Suzuki, T., Kawamura, K., Tanaka, T., Narita, M., Nagase, H., and Suzuki, T. (2004) Possible pharmacotherapy of the opioid kappa receptor agonist for drug dependence Ann N Y Acad Sci 1025, 404-413]. However, KOR has also been shown to influence stress-induced relapse to drug seeking behavior, where the longer effects of KOR agonism have been linked to KOR-dependent stress-induced potentiation of reward behavior and reinstatement of drug seeking [Beardsley, P. M., Howard, J. L., Shelton, K. L., and Carroll, F. I. (2005) Differential effects of the novel kappa opioid receptor antagonist, JDTic, on reinstatement of cocaine-seeking induced by footshock stressors vs cocaine primes and its antidepressant-like effects in rats Psychopharmacology (Berl) 183, 118-126; Redila, V. A., and Chavkin, C. (2008) Stress-induced reinstatement of cocaine seeking is mediated by the kappa opioid system Psychopharmacology (Berl) 200, 59-70].

Addiction to drugs, including cocaine, and alcohol continues to be a world-wide issue. Despite sustained efforts to develop methods for prevention and/or treatment of addiction, there is an unmet need for improvement of current therapies directed toward this goal. Many small molecule and natural product derivatives used for the treatment of pain or drug abuse have off-target effects (e.g., non-target receptor binding) leading to undesirable side effects. For example, several non-peptide KOR antagonists (e.g., nor-binaltorphimine, 5-guanidinylnaltrindole, and JDTic) exhibit unusually long duration of antagonism despite having the desired high selectivity for KOR, limiting their clinical development [Metcalf, M. D., and Coop, A. (2005) Kappa opioid antagonists: past successes and future prospects AAPS J 7, E704-722; Horan, P, Taylor, J., Yamamura, H. I., and Porreca, F. (1991) Extremely long-lasting antagonistic actions of nor-binaltorphimine (nor-BNI) in the mouse tail-flick test J Pharmacol Exp Ther 260, 1237-1243; Carroll, I., Thomas, J. B., Dykstra, L. A., Granger, A. L., Allen, R. M., Howard, J. L., Pollard, G. T., Aceto, M. D., and Harris, L. S. (2004) Pharmacological properties of JDTic: a novel kappa-opioid receptor antagonist Eur J Pharmacol 501, 111-119]. There is a continued need to develop therapeutics that selectively target opioid receptors, are orally available, and readily cross the blood-brain barrier to penetrate the central nervous system (CNS). Notably, pretreatment with KOR antagonists can prevent stress-induced reinstatement of cocaine-seeking behavior, as well as decrease compulsive cocaine-intake in the absence of stress [Carey, A. N., Borozny, K., Aldrich, J. V., and McLaughlin, J. P., (2007) Reinstatement of cocaine place-conditioning prevented by the peptide kappa-opioid receptor antagonist, Arodyn Eur J Pharmacol 569, 84-89; Ross, N. C., Reilley, K. J., Murray, T. F., Aldrich, J. V., and McLaughlin, J. P. (2012) Novel opioid cyclic tetrapeptides: Trp isomers of CJ-15,208 exhibit distinct opioid receptor agonism and short-acting κ opioid receptor antagonism Br J Pharmacol 165, 1097-1108; Wee, S. Orio, L., Ghirmai, S., Cashman, J. R., and Koob, G. F. (2009) Inhibition of kappa opioid receptors attenuated increased cocaine intake in rats with extended access to cocaine Psychopharmacology (Berl) 205, 565-575; Wee, S., Vendruscolo, L. F., Misra, K. K., Scholsburg, J. E., and Koob, G. F. (2012) A combination of buprenorphine and naltrexone blocks compulsive cocaine intake in rodents without producing dependence Sci Transl Med 4, 146ra110]. These studies suggest that molecules with KOR activity, both KOR agonists and antagonists, hold promise as medications to prevent addiction relapse and treat other CNS-related disorders (e.g., depression, anxiety, mood disorders, convulsions, and nociception).

The natural product macrocyclic tetrapeptide CJ-15,208 (cyclo [Phe-D-Pro-Phe-Trp]) and its D-Trp isomer have been shown to antagonize KOR in vitro [Ross, N. C., Kulkarni, S. S., McLaughlin, J. P., and Aldrich, J. V. (2010) Synthesis of CJ-15,208, a novel κ-opioid receptor antagonist Tetrahedron Lett 51, 5020-5023; U.S. Pat. No. 8,809,278; WO 2016/007956]. Additionally, both lead peptides demonstrate opioid activity in vivo and have the ability to prevent the reinstatement of previously extinguished cocaine seeking behavior [Aldrich, J. V., Senadheera, S. N., Ross, N. C., Ganno, M. L., Eans, S. O., and McLaughlin, J. P. (2013) The macrocyclic peptide CJ-15,208 is orally active and prevents reinstatement of extinguished cocaine-seeking behavior J Nat Prod 76, 433-438]. Importantly, these macrocyclic peptides are more resistant to protease degradation than typical peptides, yet exhibit a finite (≤1 day) duration of action, and can likely cross the blood-brain barrier after systemic administration [Eans, S. O., Ganno, M. L., Reilley, K. J., Patkar, K. A., Senadheera, S. N., Aldrich, J. V., and McLaughlin, J. P. (2013) The macrocyclic tetrapeptide (D-Trp)CJ15,208 produces short-acting κ opioid receptor antagonism in the CNS after oral administration Br J Pharmacol 169, 426-436]. Herein we describe derivatization of lead macrocyclic tetrapeptides cyclo(Phe-D-Pro-Phe-Trp) and its D-Trp isomer to modify solubility and pharmacokinetic properties without altering their pharmacological activity profile.

BRIEF SUMMARY OF THE INVENTION

The invention is directed toward macrocyclic compounds and methods of synthesis, their mechanism of action, methods of modulating opioid receptor activity, and methods of treating disease and disorders associated with the target of the macrocyclic compounds.

In one aspect, the invention provides a compound of formula (1), a salt, solvate, hydrate or prodrug thereof:

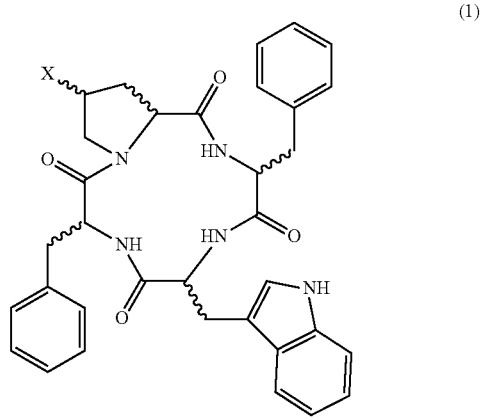

(1)

wherein, each X is independently —OH or —NH$_2$.

In another aspect, the invention provides a compound of formula (2), a salt, solvate, hydrate or prodrug thereof:

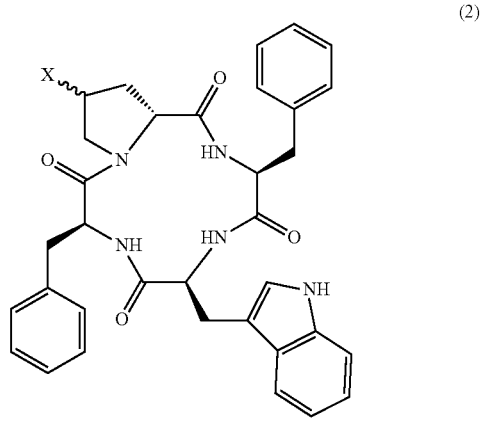

(2)

wherein, each X is independently —OH or —NH$_2$.

In another aspect, the invention provides a compound of formula (3), a salt, solvate, hydrate or prodrug thereof:

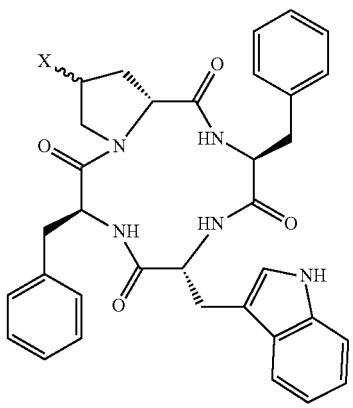

(3)

wherein, each X is independently —OH or —NH$_2$.

In another aspect, the invention provides a compound of formula (1), (2), or (3), or a salt, solvate, hydrate or prodrug thereof:

wherein X is —OH.

In another aspect, the invention provides a compound of formula (1), (2), or (3), or a salt, solvate, hydrate or prodrug thereof:

wherein X is —NH$_2$.

In another aspect, the invention provides a compound of formula (4), a salt, solvate, hydrate or prodrug thereof:

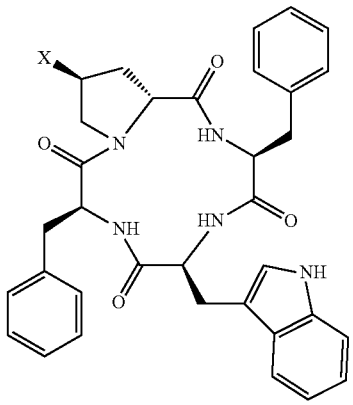

(4)

wherein, each X is independently —OH or —NH$_2$.

In another aspect, the invention provides a compound of formula (5), a salt, solvate, hydrate or prodrug thereof:

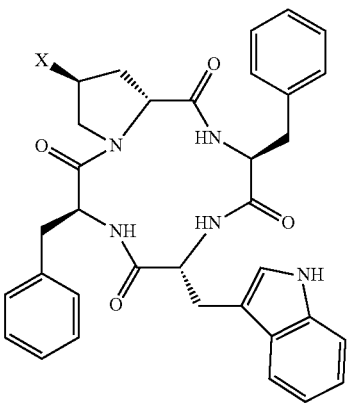

(5)

wherein, each X is independently —OH or —NH$_2$.

In another aspect, the invention provides a compound of formula (6), a salt, solvate, hydrate or prodrug thereof:

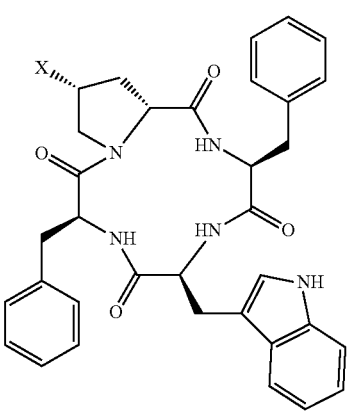

(6)

wherein, each X is independently —OH or —NH$_2$.

In another aspect, the invention provides a compound of formula (7), a salt, solvate, hydrate or prodrug thereof:

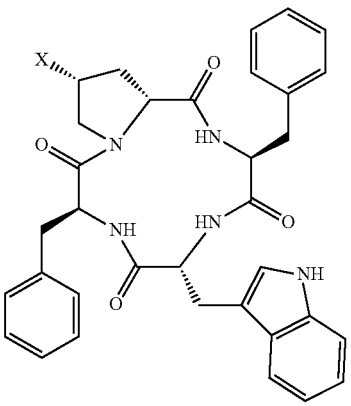

(7)

wherein, each X is independently —OH or —NH$_2$.

In another aspect, the invention provides a compound of formula (4), (5), (6), or (7) or a salt, solvate, hydrate or prodrug thereof:

wherein X is —OH.

In another aspect, the invention provides a compound of formula (4), (5), (6), or (7), or a salt, solvate, hydrate or prodrug thereof:

wherein X is —NH$_2$.

In another aspect, the invention provides a compound of formula (1), wherein the compound is:

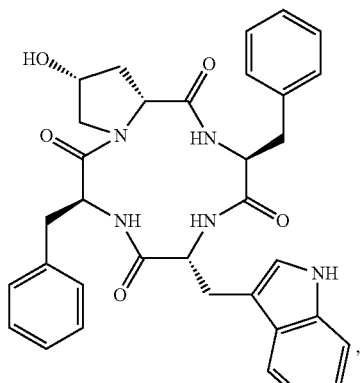

cyclo[Phe-cis-D-Hyp-Phe-D-Trp]

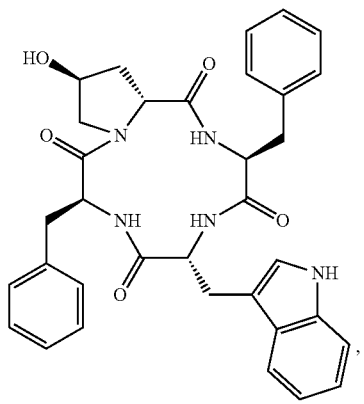

cyclo[Phe-trans-D-Hyp-Phe-D-Trp]

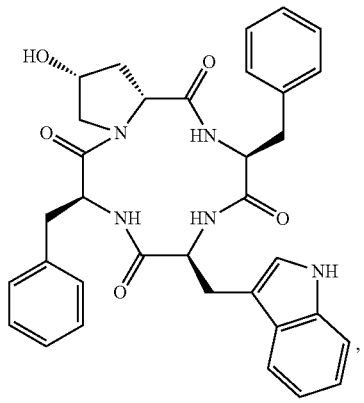

cyclo[Phe-cis-D-Hyp-Phe-Trp]

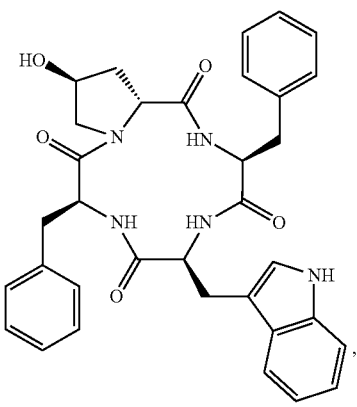

cyclo[Phe-trans-D-Hyp-Phe-Trp]

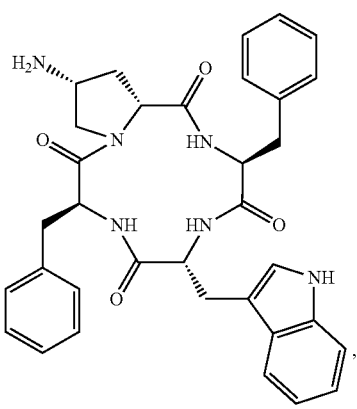

cyclo[Phe-cis-D-Amp-Phe-D-Trp]

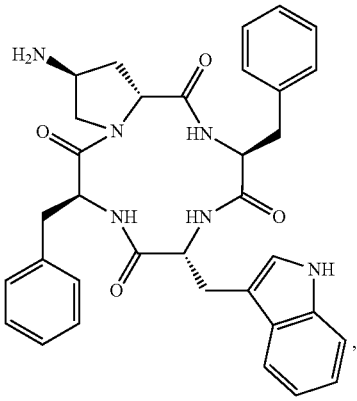

cyclo[Phe-trans-D-Amp-Phe-D-Trp]

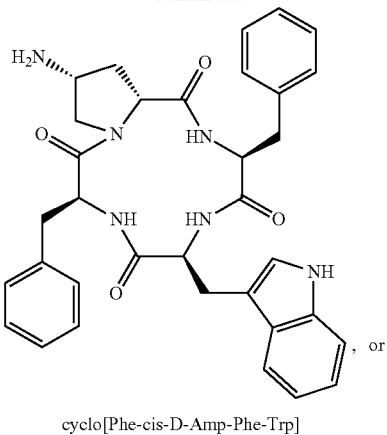

cyclo[Phe-cis-D-Amp-Phe-Trp]

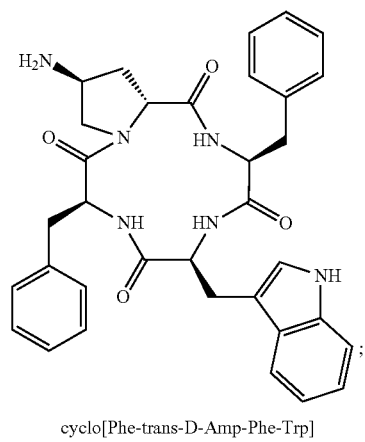

cyclo[Phe-trans-D-Amp-Phe-Trp]

or a salt, solvate, hydrate or prodrug thereof.

In another aspect, the invention provides a compound of formula (8), a salt, solvate, hydrate or prodrug thereof:

(8)

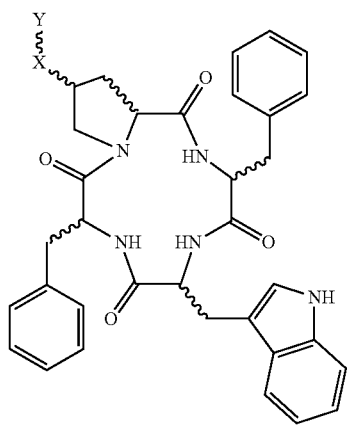

wherein, each X is independently —O or —NH;

each Y is independently —COCH$_3$, —CO(CH$_2$)$_n$R$^1$, —COCH$_2$(OCH$_2$CH$_2$)$_m$R$^1$, or —R$^2$;

each R$^1$ is independently NHR$^2$, N$_3$, or C$_{2-3}$ alkynyl;

each R is independently H or

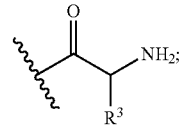

each R$^3$ is independently an amino acid side chain;

each m is independently 0, 1, 2, 3, 4, 5, 6, 7, 8, 9, or 10; and each n is independently 0, 1, 2, 3, 4, 5, 6, 7, 8, 9, or 10.

In another aspect, each R$^3$ is independently optionally substituted alkyl or optionally substituted arylalkyl. In another aspect, each R$^3$ is independently alkyl or arylalkyl. In another aspect, each R$^3$ is independently C$_1$-C$_6$ alkyl or phenyl-C$_1$-C$_6$-alkyl. In another aspect, each R$^3$ is independently methyl, ethyl, n-propyl, isopropyl, n-butyl, sec-butyl, t-butyl, benzyl, phenethyl, α-methylbenzyl, and the like. In another aspect, each R$^3$ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH$_2$)$_n$R$^1$. In another aspect, each Y is independently —R$^2$. In another aspect, each Y is independently —CO(CH$_2$)$_n$R$^1$ and R$^1$ is NHR$^2$. In another aspect, each Y is independently —CO(CH$_2$)$_n$R$^1$, R$^1$ is NHR$^2$, and R$^2$ is H. In another aspect, each Y is independently —CO(CH$_2$)$_n$R$^1$ and n is 1, 2, 3, 4, or 5. In another aspect, each Y is independently —CO(CH$_2$)$_n$R$^1$ and n is 1, 2, or 3. In another aspect, each Y is independently —CO(CH$_2$)$_n$R$^1$, n is 1, 2, 3, 4, or 5, and R$^1$ is NHR$^2$. In another aspect, each Y is independently —CO(CH$_2$)$_n$R$^1$, n is 1, 2, or 3, and R$^1$ is NHR$^2$. In another aspect, each Y is independently —CO(CH$_2$)$_n$R$^1$, n is 1, 2, 3, 4, or 5, R$^1$ is NHR$^2$, and R$^2$ is H. In another aspect, each Y is independently —CO(CH$_2$)$_n$R$^1$, n is 1, 2, or 3, R$^1$ is NHR$^2$, and R$^2$ is H. In another aspect, each X is independently —O, each Y is independently —CO(CH$_2$)$_n$R$^1$ and R$^1$ is NHR$^2$. In another aspect, each X is independently —O, each Y is independently —CO(CH$_2$)$_n$R$^1$, R$^1$ is NHR$^2$, and R$^2$ is H. In another aspect, each X is independently —O, each Y is independently —CO(CH$_2$)$_n$R$^1$ and n is 1, 2, 3, 4, or 5. In another aspect, each X is independently —O, each Y is independently —CO(CH$_2$)$_n$R$^1$ and n is 1, 2, or 3. In another aspect, each X is independently —O, each Y is independently —CO(CH$_2$)$_n$R$^1$, n is 1, 2, 3, 4, or 5, and R$^1$ is NHR$^2$. In another aspect, each X is independently —O, each Y is independently —CO(CH$_2$)$_n$R$^1$, n is 1, 2, or 3, and R$^1$ is NHR$^2$. In another aspect, each X is independently —O, each Y is independently —CO(CH$_2$)$_n$R$^1$, n is 1, 2, 3, 4, or 5, R$^1$ is NHR$^2$, and R$^2$ is H. In another aspect, each X is independently —O, each Y is independently —CO(CH$_2$)$_n$R$^1$, n is 1, 2, or 3, R$^1$ is NHR$^2$, and R$^2$ is H. In another aspect, each Y is independently —R$^2$ and R$^2$ is

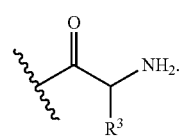

In another aspect, each Y is independently —R², R² is

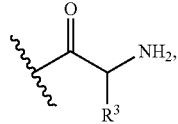

and R³ is optionally substituted alkyl or optionally substituted arylalkyl. In another aspect, each Y is independently —R², R² is

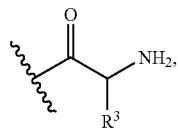

and R³ is alkyl or arylalkyl. In another aspect, each Y is independently —R², R² is

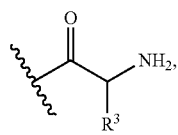

and R³ is $C_1$-$C_6$ alkyl or phenyl-$C_1$-$C_6$-alkyl. In another aspect, each Y is independently —R², R² is

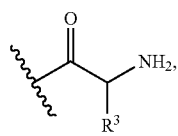

and R³ is methyl, ethyl, n-propyl, isopropyl, n-butyl, sec-butyl, t-butyl, benzyl, phenethyl, or α-methylbenzyl. In another aspect, each Y is independently —R², R² is

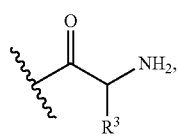

and R³ is isopropyl or benzyl. In another aspect, each X is independently —O, each Y is independently —R² and R² is

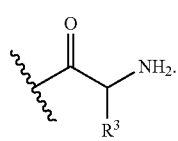

In another aspect, each X is independently —O, each Y is independently —R², R² is

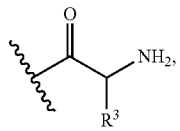

and R³ is optionally substituted alkyl or optionally substituted arylalkyl. In another aspect, each X is independently —O, each Y is independently —R², R² is

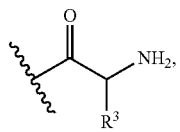

and R³ is alkyl or arylalkyl. In another aspect, each X is independently —O, each Y is independently —R², R² is

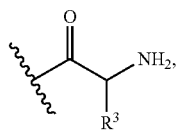

and R³ is $C_1$-$C_6$ alkyl or phenyl-$C_1$-$C_6$-alkyl. In another aspect, each X independently —O, each Y is independently —R², R² is

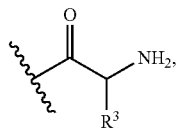

and R³ is methyl, ethyl, n-propyl, isopropyl, n-butyl, sec-butyl, t-butyl, benzyl, phenethyl, or α-methylbenzyl. In another aspect, each X is independently —O, each Y is independently —R², R² is

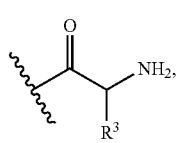

and R³ is isopropyl or benzyl.

In another aspect, the invention provides a compound of formula (9), a salt, solvate, hydrate or prodrug thereof:

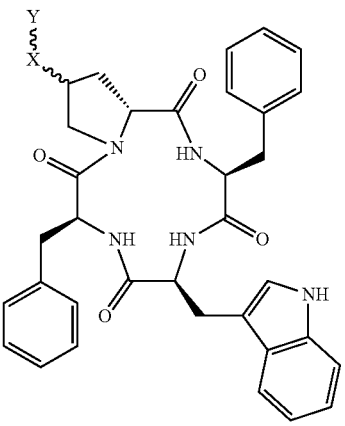
(9)

wherein,
each X is independently —O or —NH;
each Y is independently —COCH$_3$, —CO(CH$_2$)$_n$R$^1$, —COCH$_2$(OCH$_2$CH$_2$)$_m$R$^1$, or —R$^2$;
each R$^1$ is independently NHR$^2$, N$_3$, or C$_{2-3}$ alkynyl;
each R is independently H or

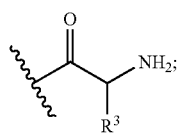

each R$^3$ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each R$^3$ is independently optionally substituted alkyl or optionally substituted arylalkyl. In another aspect, each R$^3$ is independently alkyl or arylalkyl. In another aspect, each R$^3$ is independently C$_1$-C$_6$ alkyl or phenyl-C$_1$-C$_6$-alkyl. In another aspect, each R$^3$ is independently methyl, ethyl, n-propyl, isopropyl, n-butyl, sec-butyl, t-butyl, benzyl, phenethyl, α-methylbenzyl, and the like. In another aspect, each R$^3$ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH$_2$)$_n$R$^1$. In another aspect, each Y is independently —R$^2$. In another aspect, each Y is independently —CO(CH$_2$)$_n$R$^1$ and R$^1$ is NHR$^2$. In another aspect, each Y is independently —CO(CH$_2$)$_n$R$^1$, R$^1$ is NHR$^2$, and R$^2$ is H. In another aspect, each Y is independently —CO(CH$_2$)$_n$R$^1$ and n is 1, 2, 3, 4, or 5. In another aspect, each Y is independently —CO(CH$_2$)$_n$R$^1$ and n is 1, 2, or 3. In another aspect, each Y is independently —CO(CH$_2$)$_n$R$^1$, n is 1, 2, 3, 4, or 5, and R$^1$ is NHR$^2$. In another aspect, each Y is independently —CO(CH$_2$)$_n$R$^1$, n is 1, 2, or 3, and R$^1$ is NHR$^2$. In another aspect, each Y is independently —CO(CH$_2$)$_n$R$^1$, n is 1, 2, 3, 4, or 5, R$^1$ is NHR$^2$, and R$^2$ is H. In another aspect, each Y is independently —CO(CH$_2$)$_n$R$^1$, n is 1, 2, or 3, R$^1$ is NHR$^2$, and R$^2$ is H. In another aspect, each X is independently —O, each Y is independently —CO(CH$_2$)$_n$R$^1$ and R$^1$ is NHR$^2$. In another aspect, each X is independently —O, each Y is independently —CO(CH$_2$)$_n$R$^1$, R$^1$ is NHR$^2$, and R$^2$ is H. In another aspect, each X is independently —O, each Y is independently —CO(CH$_2$)$_n$R$^1$ and n is 1, 2, 3, 4, or 5. In another aspect, each X is independently —O, each Y is independently —CO(CH$_2$)$_n$R$^1$ and n is 1, 2, or 3. In another aspect, each X is independently —O, each Y is independently —CO(CH$_2$)$_n$ R$^1$, n is 1, 2, 3, 4, or 5, and R$^1$ is NHR$^2$. In another aspect, each X is independently —O, each Y is independently —CO(CH$_2$)$_n$R$^1$, n is 1, 2, or 3, and R$^1$ is NHR$^2$. In another aspect, each X is independently —O, each Y is independently —CO(CH$_2$)$_n$R$^1$, n is 1, 2, 3, 4, or 5, R$^1$ is NHR$^2$, and R$^2$ is H. In another aspect, each X is independently —O, each Y is independently —CO(CH$_2$)$_n$R$^1$, n is 1, 2, or 3, R$^1$ is NHR$^2$, and R$^2$ is H. In another aspect, each Y is independently —R$^2$ and R$^2$ is

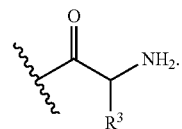

In another aspect, each Y is independently —R$^2$, R$^2$ is

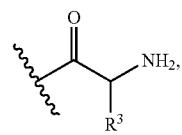

and R$^3$ is optionally substituted alkyl or optionally substituted arylalkyl. In another aspect, each Y is independently —R$^2$, R$^2$ is

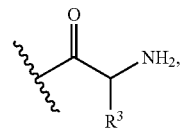

and R$^3$ is alkyl or arylalkyl. In another aspect, each Y is independently —R$^2$, R$^2$ is

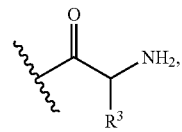

and R$^3$ is C$_1$-C$_6$ alkyl or phenyl-C$_1$-C$_6$-alkyl. In another aspect, each Y is independently —R$^2$, R$^2$ is

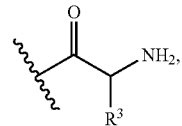

and R$^3$ is methyl, ethyl, n-propyl, isopropyl, n-butyl, sec-butyl, t-butyl, benzyl, phenethyl, or α-methylbenzyl. In another aspect, each Y is independently —R$^2$, R$^2$ is

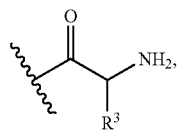

and R[3] is isopropyl or benzyl. In another aspect, each X is independently —O, each Y is independently —R[2] and R[2] is

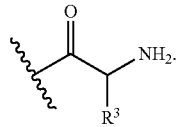

In another aspect, each X is independently —O, each Y is independently —R[2], R[2] is

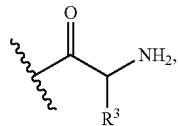

and R[3] is optionally substituted alkyl or optionally substituted arylalkyl. In another aspect, each X is independently —O, each Y is independently —R[2], R[2] is

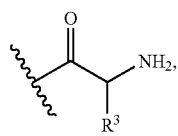

and R[3] is alkyl or arylalkyl. In another aspect, each X is independently —O, each Y is independently —R[2], R[2] is

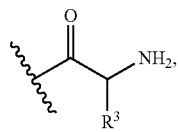

and R[3] is $C_1$-$C_6$ alkyl or phenyl-$C_1$-$C_6$-alkyl. In another aspect, each X independently —O, each Y is independently —R[2], R[2] is

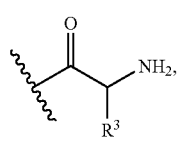

and R[3] is methyl, ethyl, n-propyl, isopropyl, n-butyl, sec-butyl, t-butyl, benzyl, phenethyl, or α-methylbenzyl. In another aspect, each X is independently —O, each Y is independently —R[2], R[2] is and R[3] is isopropyl or benzyl.

In another aspect, the invention provides a compound of formula (10), a salt, solvate, hydrate or prodrug thereof:

(10)

wherein,
each X is independently —O or —NH;
each Y is independently —COCH$_3$, —CO(CH$_2$)$_n$R[1], —COCH$_2$(OCH$_2$CH$_2$)$_m$R[1], or —R[2];
each R[1] is independently NHR[2], N$_3$, or $C_{2-3}$ alkynyl;
each R[2] is independently H or each R[3] is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each R[3] is independently optionally substituted alkyl or optionally substituted arylalkyl. In another aspect, each R[3] is independently alkyl or arylalkyl. In another aspect, each R[3] is independently $C_1$-$C_6$ alkyl or phenyl-$C_1$-$C_6$-alkyl. In another aspect, each R[3] is independently methyl, ethyl, n-propyl, isopropyl, n-butyl, sec-butyl, t-butyl, benzyl, phenethyl, α-methylbenzyl, and the like. In another aspect, each R[3] is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH$_2$)$_n$R[1]. In another aspect, each Y is independently —R[2]. In another aspect, each Y is independently —CO(CH$_2$)$_n$R[1] and R[1] is NHR[2]. In another aspect, each Y is independently —CO(CH$_2$)$_n$R[1], R[1] is NHR[2], and R[2] is H. In another aspect, each Y is independently —CO(CH$_2$)$_n$R[1] and n is 1, 2, 3, 4, or 5. In another aspect, each Y is independently —CO(CH$_2$)$_n$R[1] and n is 1, 2, or 3. In another aspect, each Y is independently —CO (CH$_2$)$_n$R$^1$, n is 1, 2, 3, 4, or 5, and R$^1$ is NHR$^2$. In another aspect, each Y is independently —CO(CH$_2$)$_n$R$^1$, n is 1, 2, or 3, and R$^1$ is NHR$^2$. In another aspect, each Y is independently —CO(CH$_2$)$_n$R$^1$, n is 1, 2, 3, 4, or 5, R$^1$ is NHR$^2$, and R$^2$ is H. In another aspect, each Y is independently —CO(CH$_2$)$_n$R$^1$, n is 1, 2, or 3, R$^1$ is NHR$^2$, and R$^2$ is H. In another aspect, each X is independently —O, each Y is independently —CO(CH$_2$)$_n$R$^1$ and R$^1$ is NHR$^2$. In another aspect, each X is independently —O, each Y is independently —CO(CH$_2$)$_n$R$^1$, R$^1$ is NHR$^2$, and R$^2$ is H. In another aspect, each X is independently —O, each Y is independently —CO(CH$_2$)$_n$R$^1$ and n is 1, 2, 3, 4, or 5. In another aspect, each X is independently —O, each Y is independently —CO(CH$_2$)$_n$R$^1$ and n is 1, 2, or 3. In another aspect, each X is independently —O, each Y is independently —CO(CH$_2$)$_n$R$^1$, n is 1, 2, 3, 4, or 5, and R$^1$ is NHR$^2$. In another aspect, each X is independently —O, each Y is independently —CO(CH$_2$)$_n$R$^1$, n is 1, 2, or 3, and R$^1$ is NHR$^2$. In another aspect, each X is independently —O, each Y is independently —CO(CH$_2$)$_n$R$^1$, n is 1, 2, 3, 4, or 5, R$^1$ is NHR$^2$, and R$^2$ is H. In another aspect, each X is independently —O, each Y is independently —CO(CH$_2$)$_n$R$^1$, n is 1, 2, or 3, R$^1$ is NHR$^2$, and R$^2$ is H. In another aspect, each Y is independently —R$^2$ and R$^2$ is

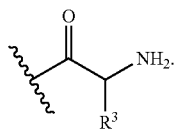

In another aspect, each Y is independently —R$^2$, R$^2$ is

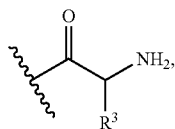

and R$^3$ is optionally substituted alkyl or optionally substituted arylalkyl. In another aspect, each Y is independently —R$^2$, R$^2$ is

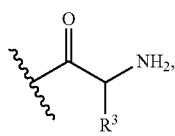

and R$^3$ is alkyl or arylalkyl. In another aspect, each Y is independently —R$^2$, R$^2$ is

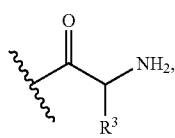

and R$^3$ is C$_1$-C$_6$ alkyl or phenyl-C$_1$-C$_6$-alkyl. In another aspect, each Y is independently —R$^2$, R$^2$ is

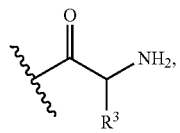

and R$^3$ is methyl, ethyl, n-propyl, isopropyl, n-butyl, sec-butyl, t-butyl, benzyl, phenethyl, or α-methylbenzyl. In another aspect, each Y is independently —R$^2$, R$^2$ is

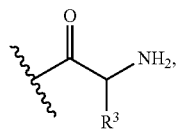

and R$^3$ is isopropyl or benzyl. In another aspect, each X is independently —O, each Y is independently —R$^2$ and R$^2$ is

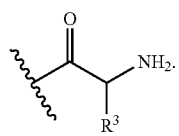

In another aspect, each X is independently —O, each Y is independently —R$^2$, R$^2$ is

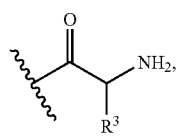

and R$^3$ is optionally substituted alkyl or optionally substituted arylalkyl. In another aspect, each X is independently —O, each Y is independently —R$^2$, R$^2$ is

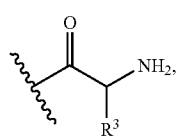

and R$^3$ is alkyl or arylalkyl. In another aspect, each X is independently —O, NH$_2$ each Y is independently —R$^2$, R$^2$ is

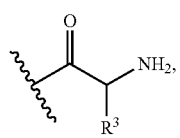

and R$^3$ is C$_1$-C$_6$ alkyl or phenyl-C$_1$-C$_6$-alkyl. In another aspect, each X is independently —O, each Y is independently —R$^2$, R$^2$ is

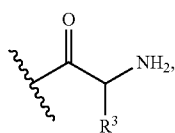

and R³ is methyl, ethyl, n-propyl, isopropyl, n-butyl, sec-butyl, t-butyl, benzyl, phenethyl, or α-methylbenzyl. In another aspect, each X is independently —O, each Y is independently —R², R² is

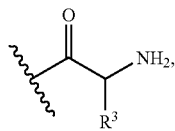

and R³ isopropyl or benzyl.

In another aspect, the invention provides a compound of formula (11), a salt, solvate, hydrate or prodrug thereof:

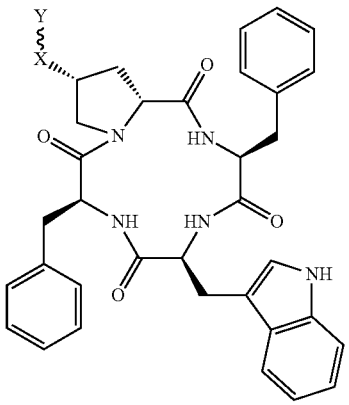

(11)

wherein,
each X is independently —O or —NH;
each Y is independently —COCH₃, —CO(CH₂)ₙR¹, —COCH₂(OCH₂CH₂)ₘR¹, or —R²;
each R¹ is independently NHR², N₃, or C₂₋₃ alkynyl;
each R² is independently H or

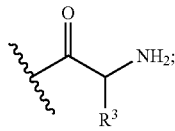

each R³ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each R³ is independently optionally substituted alkyl or optionally substituted arylalkyl. In another aspect, each R³ is independently alkyl or arylalkyl. In another aspect, each R³ is independently C₁-C₆ alkyl or phenyl-C₁-C₆-alkyl. In another aspect, each R³ is independently methyl, ethyl, n-propyl, isopropyl, n-butyl, sec-butyl, t-butyl, benzyl, phenethyl, α-methylbenzyl, and the like. In another aspect, each R³ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH₂)ₙR¹. In another aspect, each Y is independently —R². In another aspect, each Y is independently —CO(CH₂)ₙR¹ and R¹ is NHR². In another aspect, each Y is independently —CO(CH₂)ₙR¹, R¹ is NHR², and R² is H. In another aspect, each Y is independently —CO(CH₂)ₙR¹ and n is 1, 2, 3, 4, or 5. In another aspect, each Y is independently —CO(CH₂)ₙR¹ and n is 1, 2, or 3. In another aspect, each Y is independently —CO(CH₂)ₙR¹, n is 1, 2, 3, 4, or 5, and R¹ is NHR². In another aspect, each Y is independently —CO(CH₂)ₙR¹, n is 1, 2, or 3, and R¹ is NHR². In another aspect, each Y is independently —CO(CH₂)ₙR¹, n is 1, 2, 3, 4, or 5, R¹ is NHR², and R² is H. In another aspect, each Y is independently —CO(CH₂)ₙR¹, n is 1, 2, or 3, R¹ is NHR², and R² is H. In another aspect, each X is independently —O, each Y is independently —CO(CH₂)ₙR¹ and R¹ is NHR². In another aspect, each X is independently —O, each Y is independently —CO(CH₂)ₙR¹, R¹ is NHR², and R² is H. In another aspect, each X is independently —O, each Y is independently —CO(CH₂)ₙR¹ and n is 1, 2, 3, 4, or 5. In another aspect, each X is independently —O, each Y is independently —CO(CH₂)ₙR¹ and n is 1, 2, or 3. In another aspect, each X is independently —O, each Y is independently —CO(CH₂)ₙR¹, n is 1, 2, 3, 4, or 5, and R¹ is NHR². In another aspect, each X is independently —O, each Y is independently —CO(CH₂)ₙR¹, n is 1, 2, or 3, and R¹ is NHR². In another aspect, each X is independently —O, each Y is independently —CO(CH₂)ₙR¹, n is 1, 2, 3, 4, or 5, R¹ is NHR², and R² is H. In another aspect, each X is independently —O, each Y is independently —CO(CH₂)ₙR¹, n is 1, 2, or 3, R¹ is NHR², and R² is H. In another aspect, each Y is independently —R² and R² is

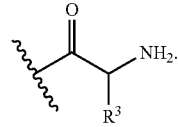

In another aspect, each Y is independently —R², R² is

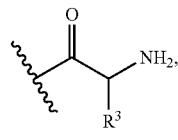

and R³ is optionally substituted alkyl or optionally substituted arylalkyl. In another aspect, each Y is independently —R², R² is

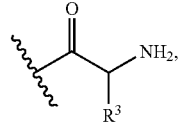

and R³ is alkyl or arylalkyl. In another aspect, each Y is independently —R², R² is

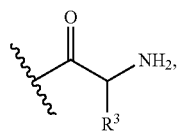

and $R^3$ is $C_1$-$C_6$ alkyl or phenyl-$C_1$-$C_6$-alkyl. In another aspect, each Y is independently —$R^2$, $R^2$ is

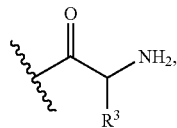

and $R^3$ is methyl, ethyl, n-propyl, isopropyl, n-butyl, sec-butyl, t-butyl, benzyl, phenethyl, or α-methylbenzyl. In another aspect, each Y is independently —$R^2$, $R^2$ is

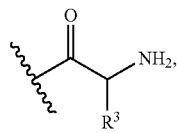

and $R^3$ is isopropyl or benzyl. In another aspect, each X is independently —O, each Y is independently —$R^2$ and $R^2$ is

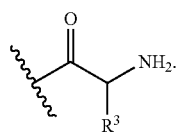

In another aspect, each X is independently —O, each Y is independently —$R^2$, $R^2$ is

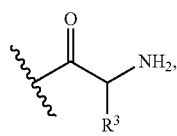

and $R^3$ is optionally substituted alkyl or optionally substituted arylalkyl. In another aspect, each X is independently —O, each Y is independently —$R^2$, $R^2$ is

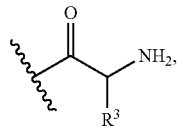

and $R^3$ is alkyl or arylalkyl. In another aspect, each X is independently —O, each Y is independently —$R^2$, $R^2$ is

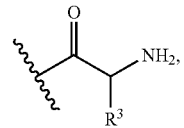

and $R^3$ is $C_1$-$C_6$ alkyl or phenyl-$C_1$-$C_6$-alkyl. In another aspect, each X is independently —O, each Y is independently —$R^2$, $R^2$ is

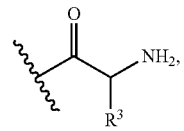

and $R^3$ is methyl, ethyl, n-propyl, isopropyl, n-butyl, sec-butyl, t-butyl, benzyl, phenethyl, or α-methylbenzyl. In another aspect, each X is independently —O, each Y is independently —$R^2$, $R^2$ is

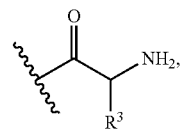

and $R^3$ is isopropyl or benzyl.

In another aspect, the invention provides a compound of formula (12), a salt, solvate, hydrate or prodrug thereof:

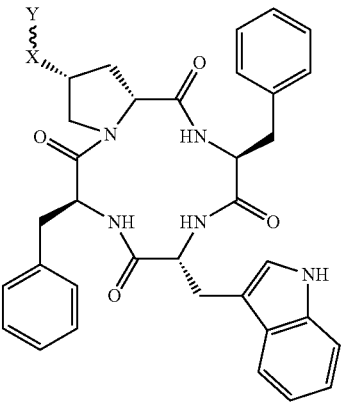

(12)

wherein,
each X is independently —O or —NH;
each Y is independently —$COCH_3$, —$CO(CH_2)_nR^1$, —$COCH_2(OCH_2CH_2)_mR^1$, or —$R^2$;
each $R^1$ is independently $NHR^2$, $N_3$, or $C_{2-3}$ alkynyl;
each R is independently H or

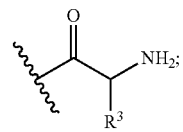

each $R^3$ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each $R^3$ is independently optionally substituted alkyl or optionally substituted arylalkyl. In another aspect, each $R^3$ is independently alkyl or arylalkyl. In another aspect, each $R^3$ is independently $C_1$-$C_6$ alkyl or phenyl-$C_1$-$C_6$-alkyl. In another aspect, each $R^3$ is independently methyl, ethyl, n-propyl, isopropyl, n-butyl, sec-butyl, t-butyl, benzyl, phenethyl, α-methylbenzyl, and the like. In another aspect, each $R^3$ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH$_2$)$_n$R$^1$. In another aspect, each Y is independently —R$^2$. In another aspect, each Y is independently —CO(CH$_2$)$_n$R$^1$ and R$^1$ is NHR$^2$. In another aspect, each Y is independently —CO(CH$_2$)$_n$R$^1$, R$^1$ is NHR$^2$, and R$^2$ is H. In another aspect, each Y is independently —CO(CH$_2$)$_n$R$^1$ and n is 1, 2, 3, 4, or 5. In another aspect, each Y is independently —CO(CH$_2$)$_n$R$^1$ and n is 1, 2, or 3. In another aspect, each Y is independently —CO(CH$_2$)$_n$R$^1$, n is 1, 2, 3, 4, or 5, and R$^1$ is NHR$^2$. In another aspect, each Y is independently —CO(CH$_2$)$_n$R$^1$, n is 1, 2, or 3, and R$^1$ is NHR$^2$. In another aspect, each Y is independently —CO(CH$_2$)$_n$R$^1$, n is 1, 2, 3, 4, or 5, R$^1$ is NHR$^2$, and R$^2$ is H. In another aspect, each Y is independently —CO(CH$_2$)$_n$R$^1$, n is 1, 2, or 3, R$^1$ is NHR$^2$, and R$^2$ is H. In another aspect, each X is independently —O, each Y is independently —CO(CH$_2$)$_n$R$^1$ and R$^1$ is NHR$^2$. In another aspect, each X is independently —O, each Y is independently —CO(CH$_2$)$_n$R$^1$, R$^1$ is NHR$^2$, and R$^2$ is H. In another aspect, each X is independently —O, each Y is independently —CO(CH$_2$)$_n$R$^1$ and n is 1, 2, 3, 4, or 5. In another aspect, each X is independently —O, each Y is independently —CO(CH$_2$)$_n$R$^1$ and n is 1, 2, or 3. In another aspect, each X is independently —O, each Y is independently —CO(CH$_2$)$_n$R$^1$, n is 1, 2, 3, 4, or 5, and R$^1$ is NHR$^2$. In another aspect, each X is independently —O, each Y is independently —CO(CH$_2$)$_n$R$^1$, n is 1, 2, or 3, and R$^1$ is NHR$^2$. In another aspect, each X is independently —O, each Y is independently —CO(CH$_2$)$_n$R$^1$, n is 1, 2, 3, 4, or 5, R$^1$ is NHR$^2$, and R$^2$ is H. In another aspect, each X is independently —O, each Y is independently —CO(CH$_2$)$_n$R$^1$, n is 1, 2, or 3, R$^1$ is NHR$^2$, and R$^2$ is H. In another aspect, each Y is independently —R$^2$ and R$^2$ is

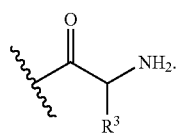

In another aspect, each Y is independently —R$^2$, R$^2$ is

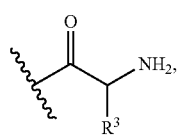

and $R^3$ is optionally substituted alkyl or optionally substituted arylalkyl. In another aspect, each Y is independently —R$^2$, R$^2$ is

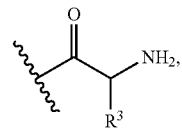

and $R^3$ is alkyl or arylalkyl. In another aspect, each Y is independently —R$^2$, R$^2$ is

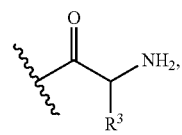

and $R^3$ is $C_1$-$C_6$ alkyl or phenyl-$C_1$-$C_6$-alkyl. In another aspect, each Y is independently —R$^2$, R$^2$ is

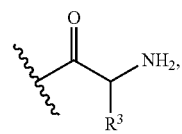

and $R^3$ is methyl, ethyl, n-propyl, isopropyl, n-butyl, sec-butyl, t-butyl, benzyl, phenethyl, or α-methylbenzyl. In another aspect, each Y is independently —R$^2$, R$^2$ is

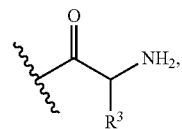

and $R^3$ is isopropyl or benzyl. In another aspect, each X is independently —O, each Y is independently —R$^2$ and R$^2$ is

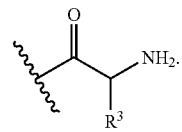

In another aspect, each X is independently —O, each Y is independently —R$^2$, R$^2$ is

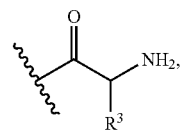

and $R^3$ is optionally substituted alkyl or optionally substituted arylalkyl. In another aspect, each X is independently —O, each Y is independently —R$^2$, R$^2$ is

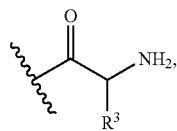

and $R^3$ is alkyl or arylalkyl. In another aspect, each X is independently —O, each Y is independently —$R^2$, $R^2$ is

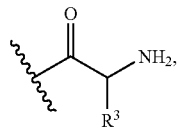

and $R^3$ is $C_1$-$C_6$ alkyl or phenyl-$C_1$-$C_6$-alkyl. In another aspect, each X is independently —O, each Y is independently —$R^2$, $R^2$ is

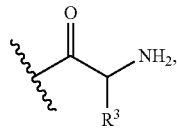

and $R^3$ is methyl, ethyl, n-propyl, isopropyl, n-butyl, sec-butyl, t-butyl, benzyl, phenethyl, or α-methylbenzyl. In another aspect, each X is independently —O, each Y is independently —$R^2$, $R^2$ is

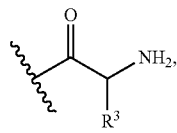

and $R^3$ is isopropyl or benzyl.

In another aspect, the invention provides a compound of formula (13), a salt, solvate, hydrate or prodrug thereof:

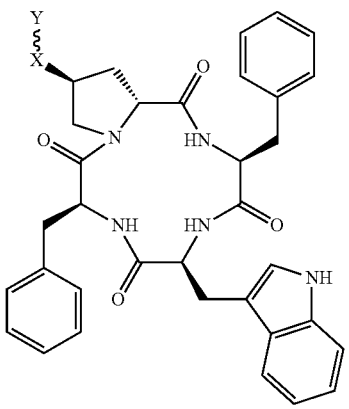

(13)

wherein,
each X is independently —O or —NH;
each Y is independently —$COCH_3$, —$CO(CH_2)_nR^1$, —$COCH_2(OCH_2CH_2)_mR^1$, or —$R^2$;

each $R^1$ is independently $NHR^2$, $N_3$, or $C_{2-3}$ alkynyl;
each R is independently H or

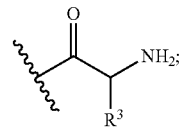

each $R^3$ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each $R^3$ is independently optionally substituted alkyl or optionally substituted arylalkyl. In another aspect, each $R^3$ is independently alkyl or arylalkyl. In another aspect, each $R^3$ is independently $C_1$-$C_6$ alkyl or phenyl-$C_1$-$C_6$-alkyl. In another aspect, each $R^3$ is independently methyl, ethyl, n-propyl, isopropyl, n-butyl, sec-butyl, t-butyl, benzyl, phenethyl, α-methylbenzyl, and the like. In another aspect, each $R^3$ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —$CO(CH_2)_nR^1$. In another aspect, each Y is independently —$R^2$. In another aspect, each Y is independently —$CO(CH_2)_nR^1$ and $R^1$ is $NHR^2$. In another aspect, each Y is independently —$CO(CH_2)_nR^1$, $R^1$ is $NHR^2$, and $R^2$ is H. In another aspect, each Y is independently —$CO(CH_2)_nR^1$ and n is 1, 2, 3, 4, or 5. In another aspect, each Y is independently —$CO(CH_2)_nR^1$ and n is 1, 2, or 3. In another aspect, each Y is independently —$CO(CH_2)_nR^1$, n is 1, 2, 3, 4, or 5, and $R^1$ is $NHR^2$. In another aspect, each Y is independently —$CO(CH_2)_nR^1$, n is 1, 2, or 3, and $R^1$ is $NHR^2$. In another aspect, each Y is independently —$CO(CH_2)_nR^1$, n is 1, 2, 3, 4, or 5, $R^1$ is $NHR^2$, and $R^2$ is H. In another aspect, each Y is independently —$CO(CH_2)_nR^1$, n is 1, 2, or 3, $R^1$ is $NHR^2$, and $R^2$ is H. In another aspect, each X is independently —O, each Y is independently —$CO(CH_2)_nR^1$ and $R^1$ is $NHR^2$. In another aspect, each X is independently —O, each Y is independently —$CO(CH_2)$. $R^1$, $R^1$ is $NHR^2$, and $R^2$ is H. In another aspect, each X is independently —O, each Y is independently —$CO(CH_2)_nR^1$ and n is 1, 2, 3, 4, or 5. In another aspect, each X is independently —O, each Y is independently —$CO(CH_2)_nR^1$ and n is 1, 2, or 3. In another aspect, each X is independently —O, each Y is independently —$CO(CH_2)_nR^1$, n is 1, 2, 3, 4, or 5, and $R^1$ is $NHR^2$. In another aspect, each X is independently —O, each Y is independently —$CO(CH_2)_nR^1$, n is 1, 2, or 3, and $R^1$ is $NHR^2$. In another aspect, each X is independently —O, each Y is independently —$CO(CH_2)_nR^1$, n is 1, 2, 3, 4, or 5, $R^1$ is $NHR^2$, and $R^2$ is H. In another aspect, each X is independently —O, each Y is independently —$CO(CH_2)_nR^1$, n is 1, 2, or 3, $R^1$ is $NHR^2$, and $R^2$ is H. In another aspect, each Y is independently —$R^2$ and $R^2$ is

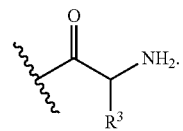

In another aspect, each Y is independently —R², R² is

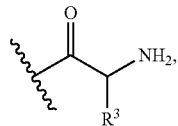

and R³ is optionally substituted alkyl or optionally substituted arylalkyl. In another aspect, each Y is independently —R², R² is

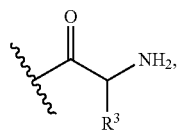

and R³ is alkyl or arylalkyl. In another aspect, each Y is independently —R², R² is

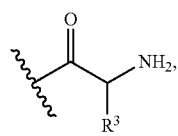

and R³ is $C_1$-$C_6$ alkyl or phenyl-$C_1$-$C_6$-alkyl. In another aspect, each Y is independently —R², R² is

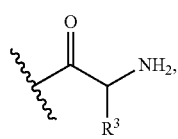

and R³ is methyl, ethyl, n-propyl, isopropyl, n-butyl, sec-butyl, t-butyl, benzyl, phenethyl, or α-methylbenzyl. In another aspect, each Y is independently —R², R² is

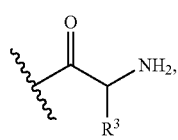

and R³ is isopropyl or benzyl. In another aspect, each X is independently —O, each Y is independently —R² and R² is

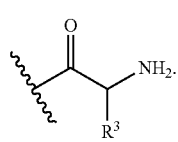

In another aspect, each X is independently —O, each Y is independently —R², R² is

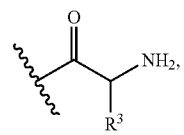

and R³ is optionally substituted alkyl or optionally substituted arylalkyl. In another aspect, each X is independently —O, each Y is independently —R², R² is

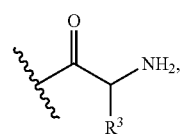

and R³ is alkyl or arylalkyl. In another aspect, each X is independently —O, each Y is independently —R², R² is

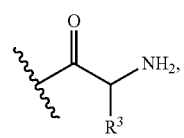

and R³ is $C_1$-$C_6$ alkyl or phenyl-$C_1$-$C_6$-alkyl. In another aspect, each X is independently —O, each Y is independently —R², R² is

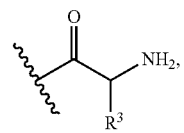

and R³ is methyl, ethyl, n-propyl, isopropyl, n-butyl, sec-butyl, t-butyl, benzyl, phenethyl, or α-methylbenzyl. In another aspect, each X is independently —O, each Y is independently —R², R² is

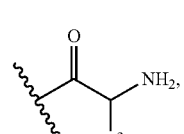

and R³ is isopropyl or benzyl.

In another aspect, the invention provides a compound of formula (14), a salt, solvate, hydrate or prodrug thereof:

(14)

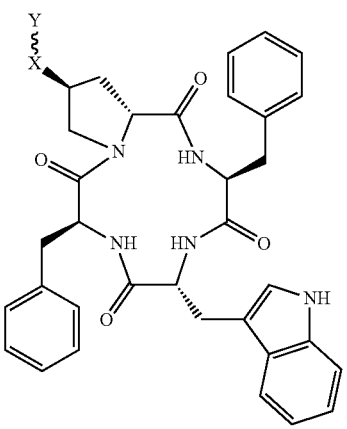

wherein,
each X is independently —O or —NH;
each Y is independently —COCH$_3$, —CO(CH$_2$)$_n$R$^1$, —COCH$_2$(OCH$_2$CH$_2$)$_m$R$^1$, or —R$^2$;
each R$^1$ is independently NHR$^2$, N$_3$, or C$_{2-3}$ alkynyl;
each R$^3$ is independently H or

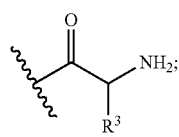

each R$^3$ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

In another aspect, each R$^3$ is independently optionally substituted alkyl or optionally substituted arylalkyl. In another aspect, each R$^3$ is independently alkyl or arylalkyl. In another aspect, each R$^3$ is independently C$_1$-C$_6$ alkyl or phenyl-C$_1$-C$_6$-alkyl. In another aspect, each R$^3$ is independently methyl, ethyl, n-propyl, isopropyl, n-butyl, sec-butyl, t-butyl, benzyl, phenethyl, α-methylbenzyl, and the like. In another aspect, each R$^3$ is independently isopropyl or benzyl. In another aspect, each n is independently 1, 2, 3, 4, or 5. In another aspect, each n is independently 1, 2, or 3. In another aspect, each X is independently —O. In another aspect, each Y is independently —CO(CH$_2$)$_n$R$^1$. In another aspect, each Y is independently —R$^2$. In another aspect, each Y is independently —CO(CH$_2$)$_n$R and R$^1$ is NHR$^2$. In another aspect, each Y is independently —CO(CH$_2$)$_n$R$^1$, R$^1$ is NHR$^2$, and R$^2$ is H. In another aspect, each Y is independently —CO(CH$_2$)$_n$R$^1$ and n is 1, 2, 3, 4, or 5. In another aspect, each Y is independently —CO(CH$_2$)$_n$R$^1$ and n is 1, 2, or 3. In another aspect, each Y is independently —CO(CH$_2$)$_n$R$^1$, n is 1, 2, 3, 4, or 5, and R$^1$ is NHR$^2$. In another aspect, each Y is independently —CO(CH$_2$)$_n$R$^1$, n is 1, 2, or 3, and R$^1$ is NHR$^2$. In another aspect, each Y is independently —CO(CH$_2$)$_n$R$^1$, n is 1, 2, 3, 4, or 5, R$^1$ is NHR$^2$, and R$^2$ is H. In another aspect, each Y is independently —CO(CH$_2$)$_n$R$^1$, n is 1, 2, or 3, R$^1$ is NHR$^2$, and R$^2$ is H. In another aspect, each X is independently —O, each Y is independently —CO(CH$_2$)$_n$R$^1$ and R$^1$ is NHR$^2$. In another aspect, each X is independently —O, each Y is independently —CO(CH$_2$)$_n$R$^1$, R$^1$ is NHR$^2$, and R$^2$ is H. In another aspect, each X is independently —O, each Y is independently —CO(CH$_2$)$_n$R$^1$ and n is 1, 2, 3, 4, or 5. In another aspect, each X is independently —O, each Y is independently —CO(CH$_2$)$_n$R$^1$ and n is 1, 2, or 3. In another aspect, each X is independently —O, each Y is independently —CO(CH$_2$)$_n$R$^1$, n is 1, 2, 3, 4, or 5, and R$^1$ is NHR$^2$. In another aspect, each X is independently —O, each Y is independently —CO(CH$_2$)$_n$R$^1$, n is 1, 2, or 3, and R$^1$ is NHR$^2$. In another aspect, each X is independently —O, each Y is independently —CO(CH$_2$)$_n$R$^1$, n is 1, 2, 3, 4, or 5, R$^1$ is NHR$^2$, and R$^2$ is H. In another aspect, each X is independently —O, each Y is independently —CO(CH$_2$)$_n$R$^1$, n is 1, 2, or 3, R$^1$ is NHR$^2$, and R$^2$ is H. In another aspect, each Y is independently —R$^2$ and R$^2$ is

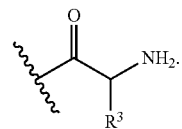

In another aspect, each Y is independently —R$^2$, R$^2$ is

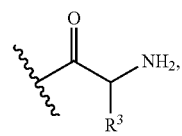

and R$^3$ is optionally substituted alkyl or optionally substituted arylalkyl. In another aspect, each Y is independently —R$^2$, R$^2$ is

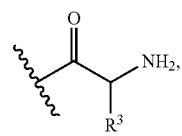

and R$^3$ is alkyl or arylalkyl. In another aspect, each Y is independently —R$^2$, R$^2$ is

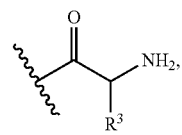

and R$^3$ is C$_1$-C$_6$ alkyl or phenyl-C$_1$-C$_6$-alkyl. In another aspect, each Y is independently —R$^2$, R$^2$ is

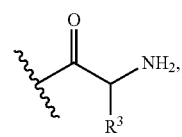

and R$^3$ is methyl, ethyl, n-propyl, isopropyl, n-butyl, sec-butyl, t-butyl, benzyl, phenethyl, or α-methylbenzyl. In another aspect, each Y is independently —R$^2$, R$^2$ is

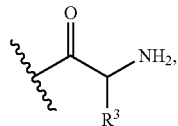

and R³ is isopropyl or benzyl. In another aspect, each X is independently —O, each Y is independently —R² and R² is

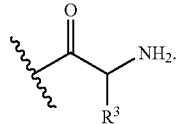

In another aspect, each X is independently —O, each Y is independently —R², R² is

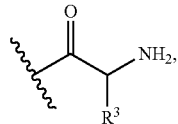

and R³ is optionally substituted alkyl or optionally substituted arylalkyl. In another aspect, each X is independently —O, each Y is independently —R², R² is

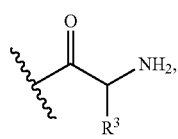

and R³ is alkyl or arylalkyl. In another aspect, each X is independently —O, each Y is independently —R², R² is

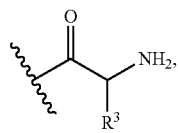

and R³ is $C_1$-$C_6$ alkyl or phenyl-$C_1$-$C_6$-alkyl. In another aspect, each X is independently —O, each Y is independently —R², R² is

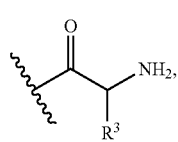

and R³ is methyl, ethyl, n-propyl, isopropyl, n-butyl, sec-butyl, t-butyl, benzyl, phenethyl, or α-methylbenzyl. In another aspect, each X is independently —O, each Y is independently —R, R² is

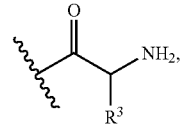

and R³ is isopropyl or benzyl.

In another aspect, the invention provides a compound of formula (8), (9), (10), (11), (12), (13), or (14) or a salt, solvate, hydrate or prodrug thereof:
wherein,
X is —O;
Y is independently —COCH₃, —CO(CH₂)ₙR¹, —COCH₂(OCH₂CH₂)ₘR¹, or —R²;
each R¹ is independently NHR², N₃, or $C_{2-3}$ alkynyl;
each R² is independently H or

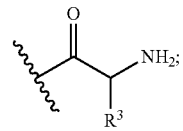

each R³ is independently an amino acid side chain;
each m is independently 0, 1, 2, or 3; and
each n is independently 0, 1, 2, or 3.

In another aspect, the invention provides a compound of formula (8), (9), (10), (11), (12), (13), or (14) or a salt, solvate, hydrate or prodrug thereof:
wherein,
X is —NH;
Y is independently —COCH₃, —CO(CH₂)ₙR¹, —COCH₂(OCH₂CH₂)ₘR¹, or —R²;
each R¹ is independently NHR², N₃, or $C_{2-3}$ alkynyl;
each R² is independently H or

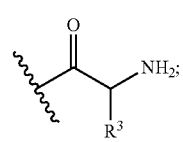

each R³ is independently an amino acid side chain;
each m is independently 0, 1, 2, or 3; and
each n is independently 0, 1, 2, or 3.

In another aspect, the invention provides a compound of formula (8), (9), (10), (11), (12), (13), or (14) or a salt, solvate, hydrate or prodrug thereof:
wherein,
X is —O;
each Y is independently —COCH₃, —CO(CH₂)ₙR¹, —COCH₂(OCH₂CH₂)ₘR¹, or —R²;
each R¹ is independently NHR², N₃, or $C_{2-3}$ alkynyl;
each R¹ is independently H or

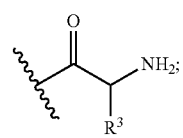

each R³ is independently an amino acid side chain comprising Gly, Ala, Phe, Val, Lys, and Asp;
each m is independently 0, 1, 2, 3, 4, 5, 6, 7, 8, 9, or 10;
each n is independently 0, 1, 2, 3, 4, 5, 6, 7, 8, 9, or 10.

In another aspect, the invention provides a compound of formula (8), (9), (10), (11), (12), (13), or (14) or a salt, solvate, hydrate or prodrug thereof:
wherein,
X is —NH;
each Y is independently —COCH₃, —CO(CH₂)$_n$R¹, —COCH₂(OCH₂CH₂)$_m$R¹, or —R²;
each R¹ is independently NHR², N₃, or C$_{2-3}$ alkynyl;
each R² is independently H or

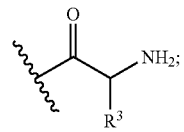

each R³ is independently an amino acid side chain comprising Gly, Ala, Phe, Val, Lys, and Asp;
each m is independently 0, 1, 2, 3, 4, 5, 6, 7, 8, 9, or 10;
each n is independently 0, 1, 2, 3, 4, 5, 6, 7, 8, 9, or 10.

In another aspect, the invention provides a compound of formula (8), (9), (10), (11), (12), (13), or (14) or a salt, solvate, hydrate or prodrug thereof:
wherein,
X is —O;
Y is independently —COCH₃, —CO(CH₂)$_n$R¹, —COCH₂(OCH₂CH₂)$_m$R¹, or —R²;
each R¹ is independently NHR², N₃, or C$_{2-3}$ alkynyl;
each R² is independently H or

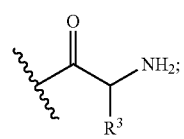

each R³ is independently an amino acid side chain comprising Gly, Ala, Phe, Val, Lys, and Asp;
each m is independently 0, 1, 2, or 3; and
each n is independently 0, 1, 2, or 3.

In another aspect, the invention provides a compound of formula (8), (9), (10), (11), (12), (13), or (14) or a salt, solvate, hydrate or prodrug thereof:
wherein,
X is —NH;
Y is independently —COCH₃, —CO(CH₂)$_n$R¹, —COCH₂(OCH₂CH₂)$_m$R¹, or —R²;
each R¹ is independently NHR², N₃, or C$_{2-3}$ alkynyl;
each R² is independently H or

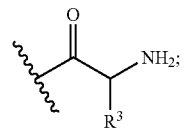

each R³ is independently an amino acid side chain comprising Gly, Ala, Phe, Val, Lys, and Asp;

each m is independently 0, 1, 2, or 3; and
each n is independently 0, 1, 2, or 3.

In another aspect, the invention provides a compound of formula (8), wherein the compound is:

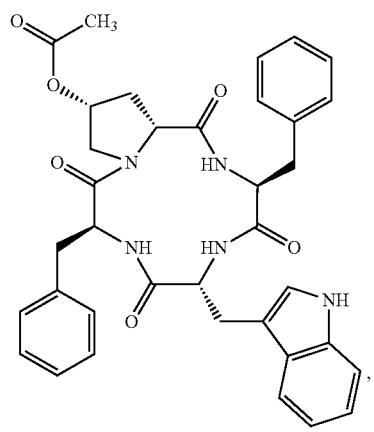

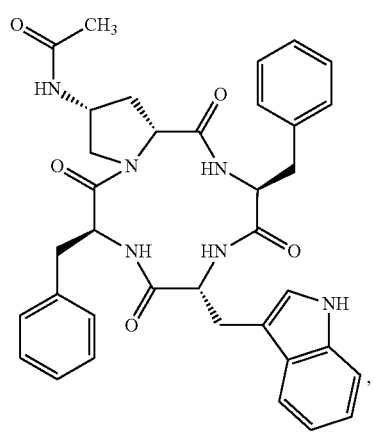

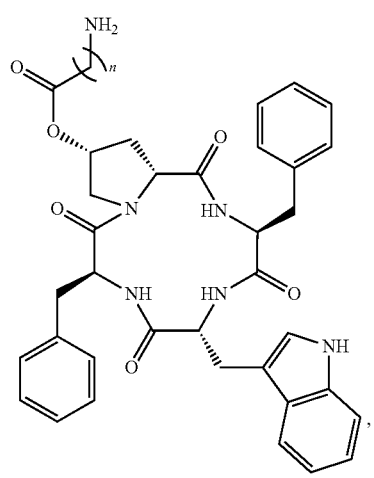

35
-continued
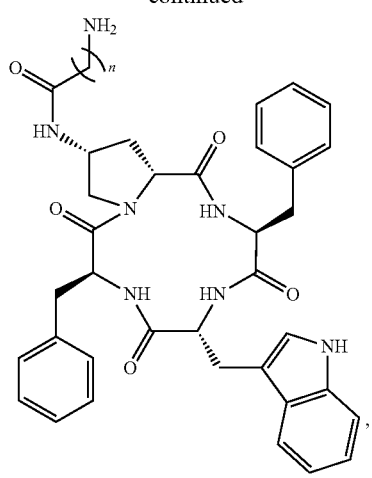
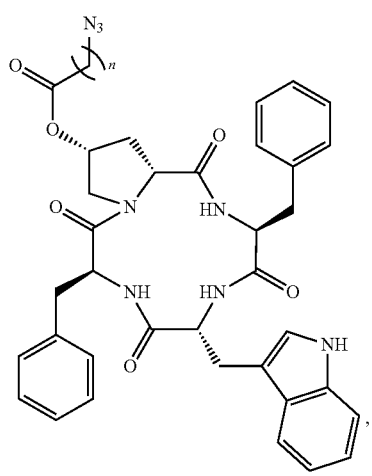
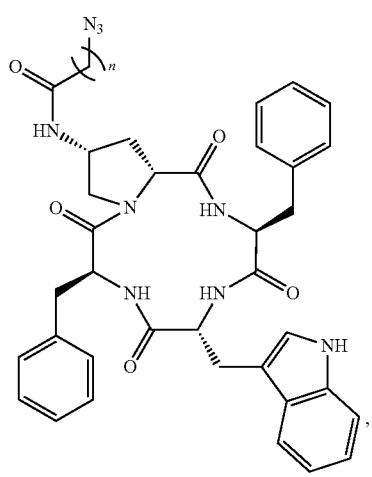
36
-continued
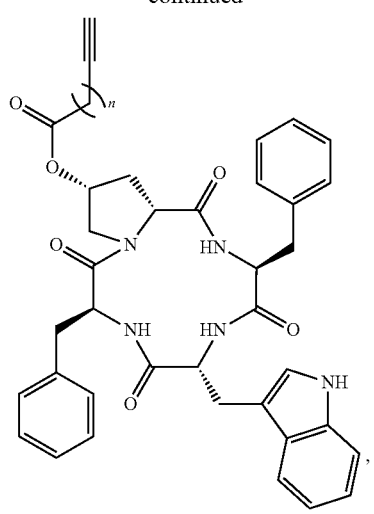
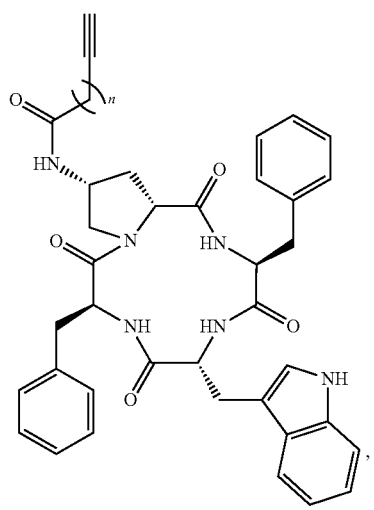
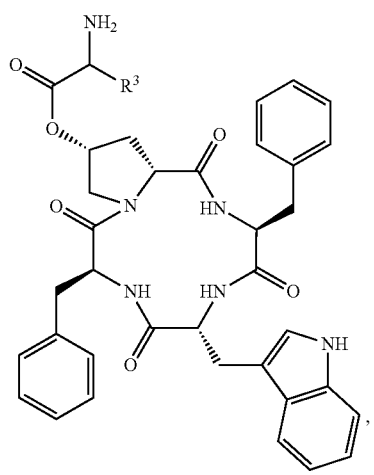

37
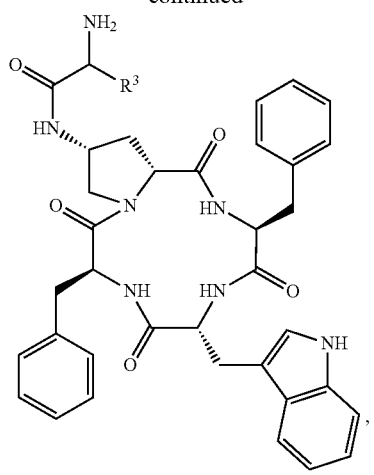
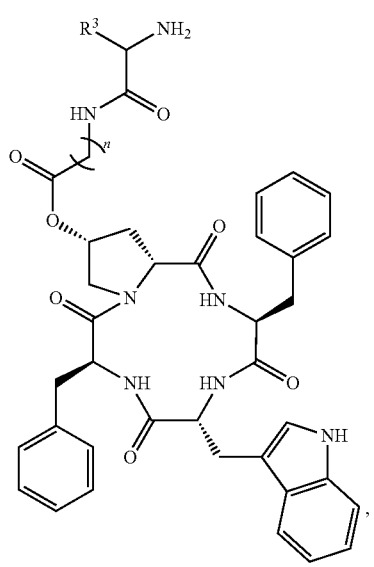
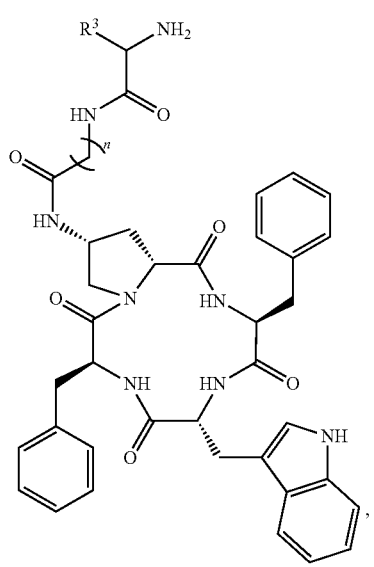
38
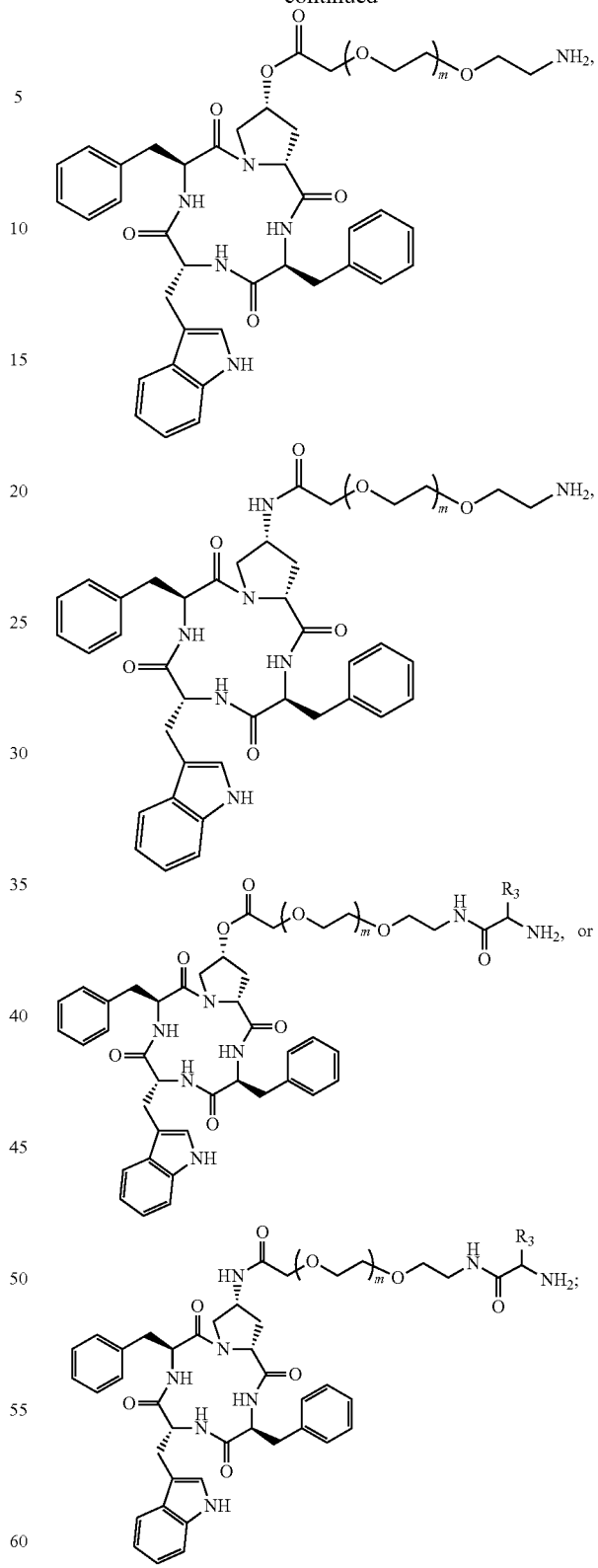
wherein,
each R³ is independently an amino acid side chain;
each m is independently 0, 1, 2, 3, 4, 5, 6, 7, 8, 9, or 10; and each n is independently 0, 1, 2, 3, 4, 5, 6, 7, 8, 9, or 10; or a salt, solvate, hydrate or prodrug thereof.
In another aspect, the invention provides a compound of formula (8), wherein the compound is:
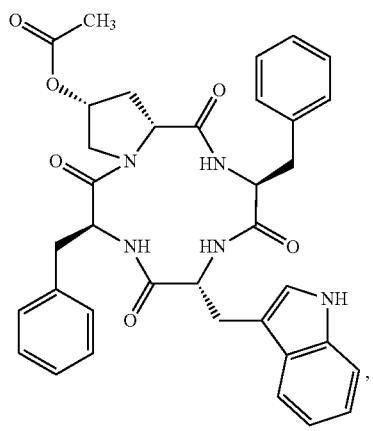
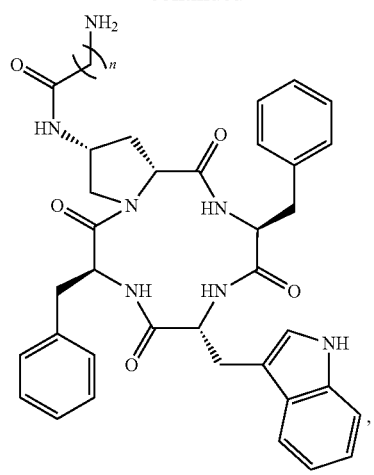
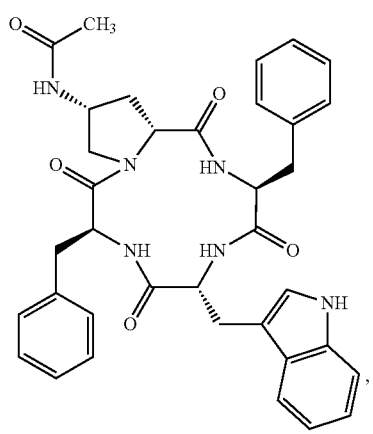
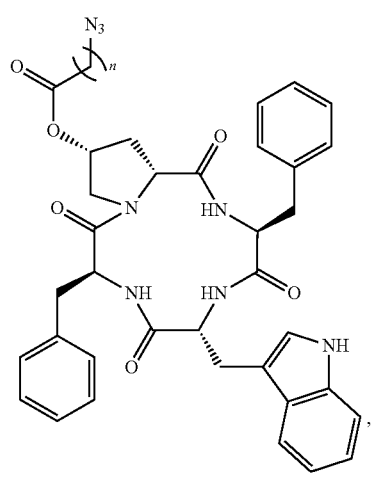
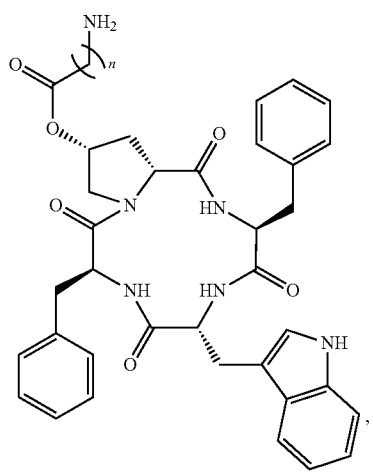
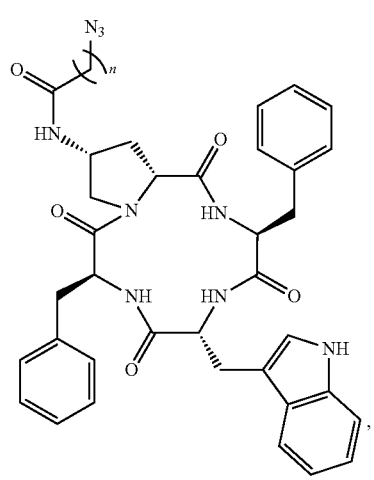

41
-continued
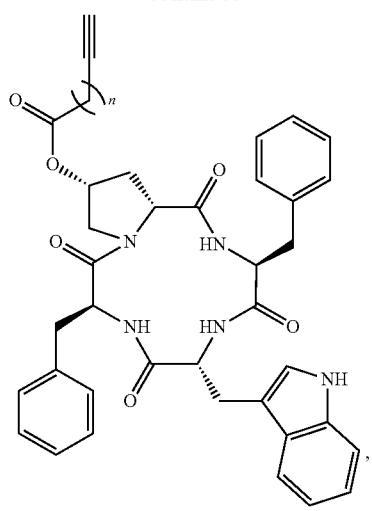
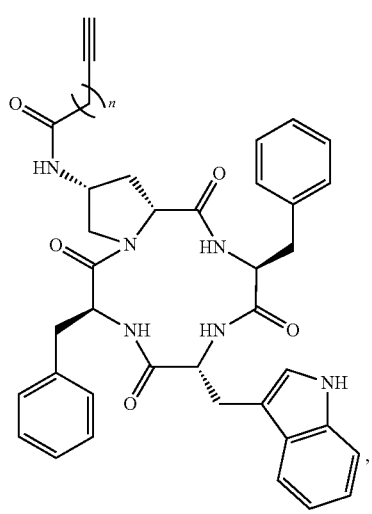
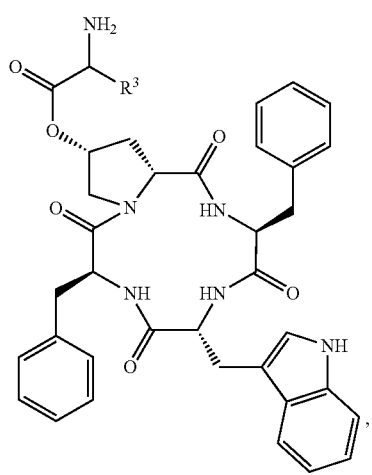
42
-continued
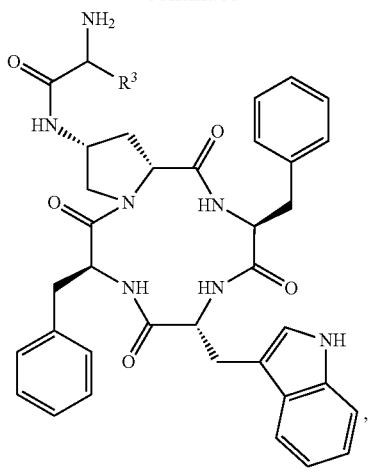
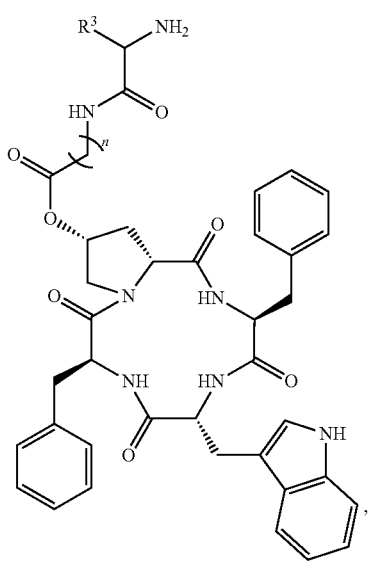
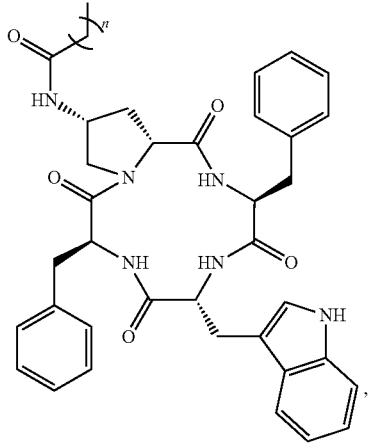

-continued

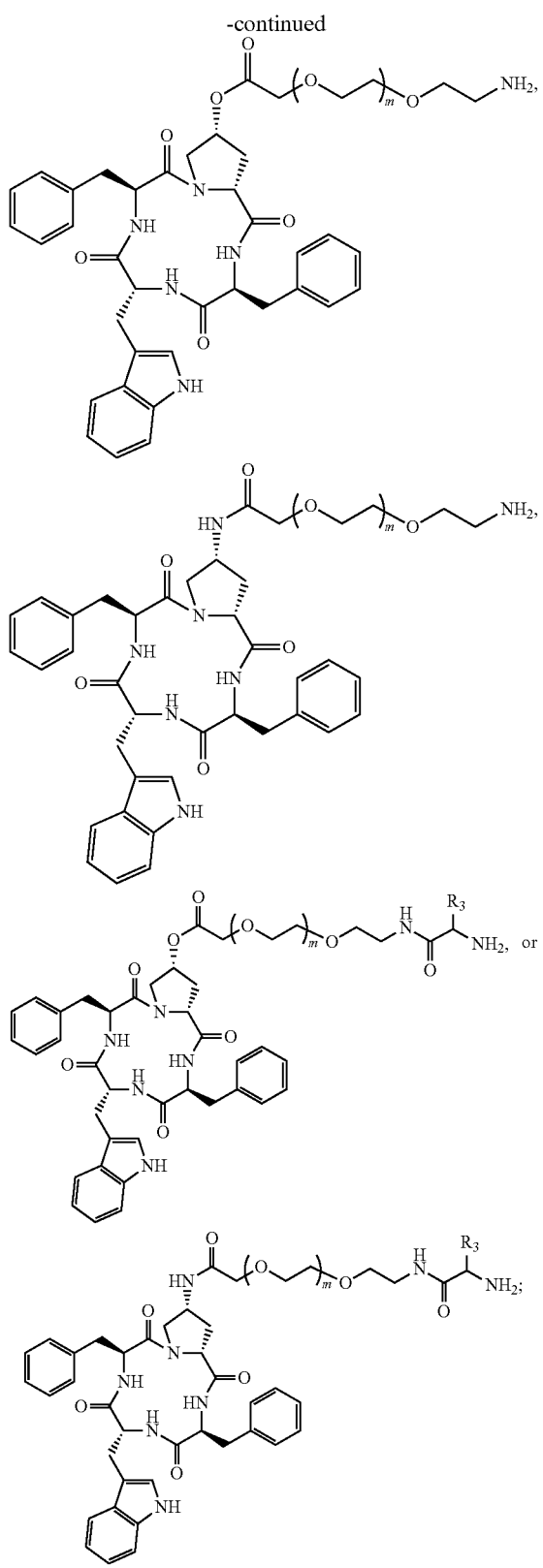

wherein,
each R³ is independently an amino acid side chain comprising Gly, Ala, Phe, Val, Lys, and Asp;
each m is independently 0, 1, 2, 3, 4, 5, 6, 7, 8, 9, or 10; and
each n is independently 0, 1, 2, 3, 4, 5, 6, 7, 8, 9, or 10; or a salt, solvate, hydrate or prodrug thereof.

In another aspect, the invention provides a compound of formula (15), a salt, solvate, hydrate or prodrug thereof:

(15)

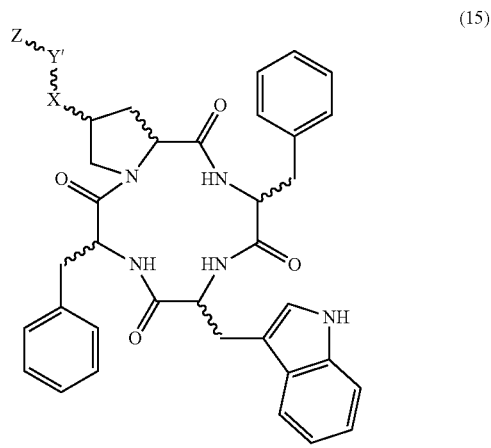

wherein,
each X is independently —O or —NH;
each Y' is independently —CO(CH$_2$)$_n$NHZ or —COCH$_2$(OCH$_2$CH$_2$)$_m$NHZ;
each Z is independently H or

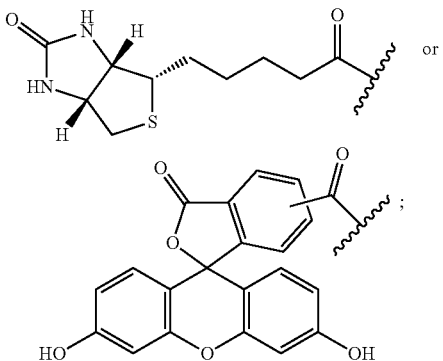

each m is independently 0, 1, 2, 3, 4, 5, 6, 7, 8, 9, or 10; and
each n is independently 0, 1, 2, 3, 4, 5, 6, 7, 8, 9, or 10.

In another aspect, the invention provides a compound of formula (15), or a salt, solvate, hydrate or prodrug thereof: wherein,
X is —O;
each Y' is independently —CO(CH$_2$)$_n$NHZ or —COCH$_2$(OCH$_2$CH$_2$)$_m$NHZ;
each Z is independently

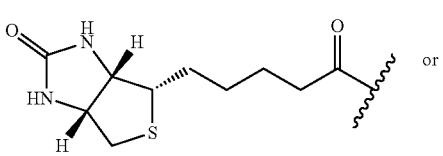

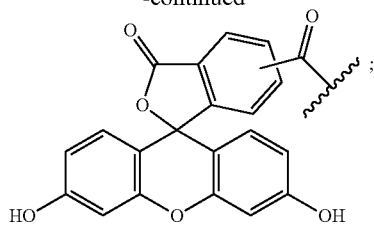

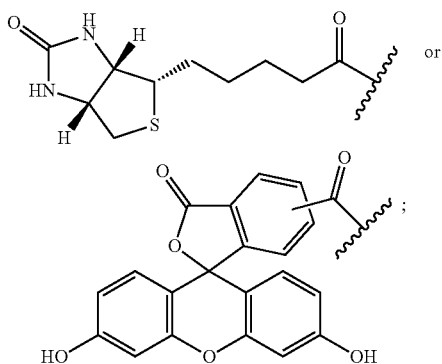

each m is independently 0, 1, 2, or 3; and
each n is independently 0, 1, 2, or 3.

In another aspect, the invention provides a compound of formula (15), or a salt, solvate, hydrate or prodrug thereof: wherein, X is —NH;
each Y' is independently —CO(CH$_2$)$_n$NHZ or —COCH$_2$(OCH$_2$CH$_2$)$_m$NHZ;
each Z is independently each m is independently 0, 1, 2, or 3; and
each n is independently 0, 1, 2, or 3.

In another aspect, the invention provides a compound of formula (15), wherein the compound is:

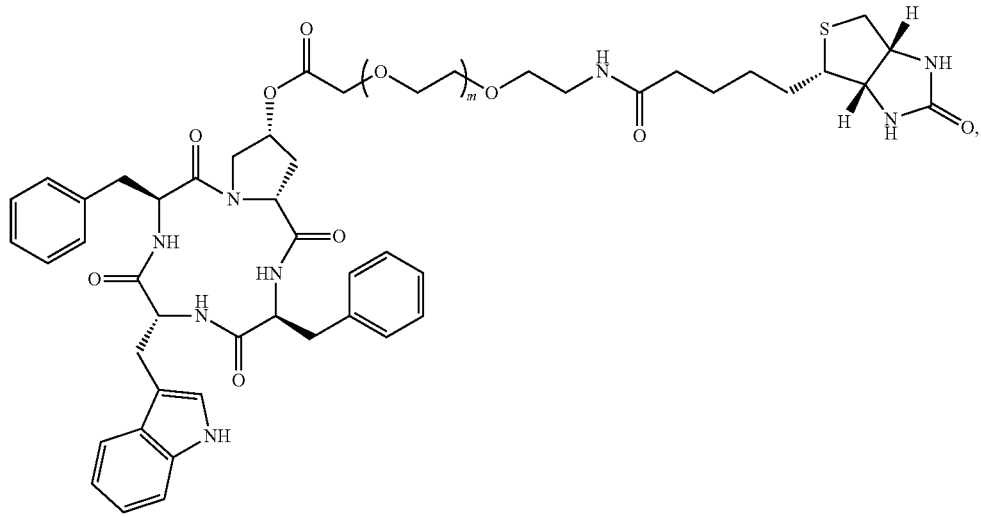

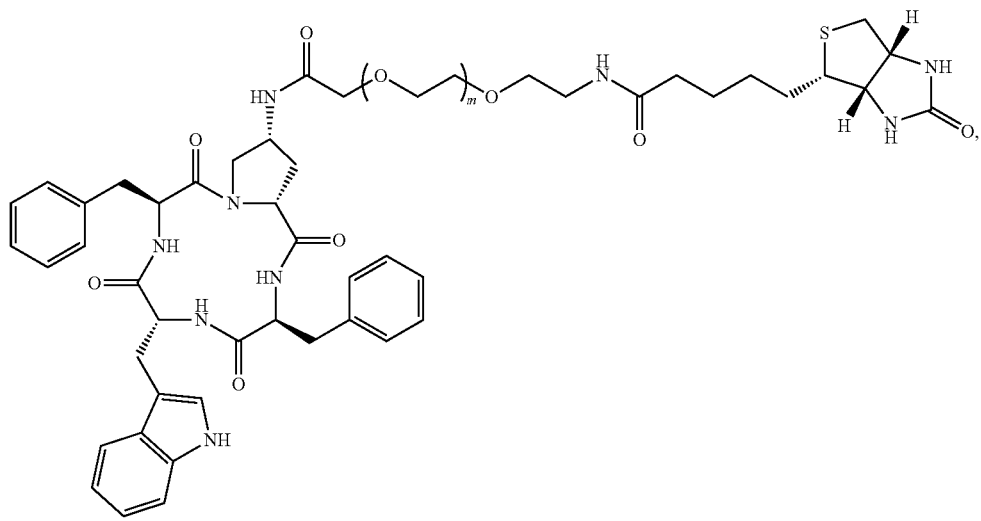

-continued
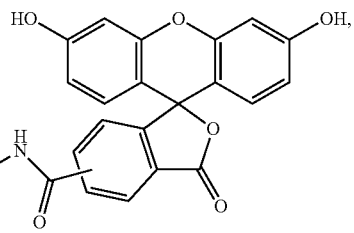
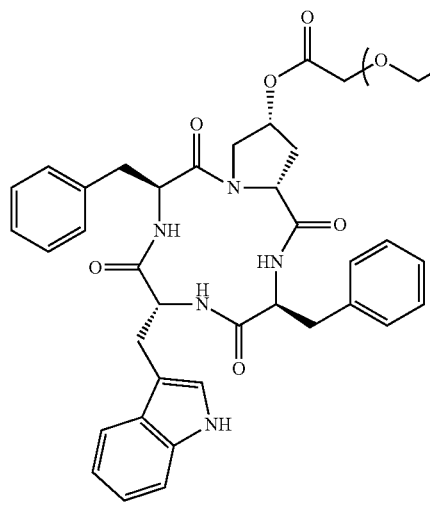
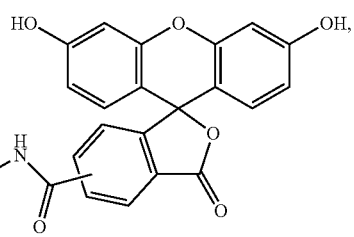
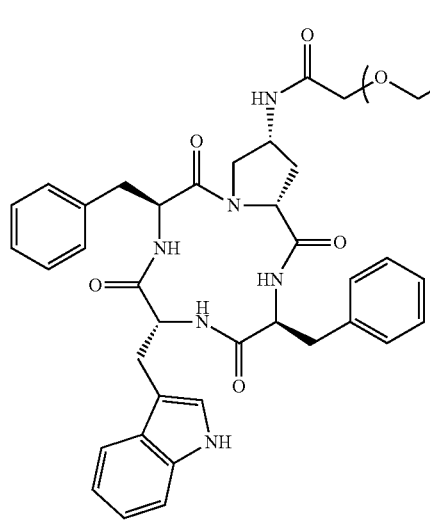
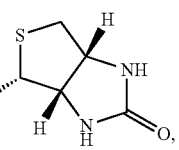
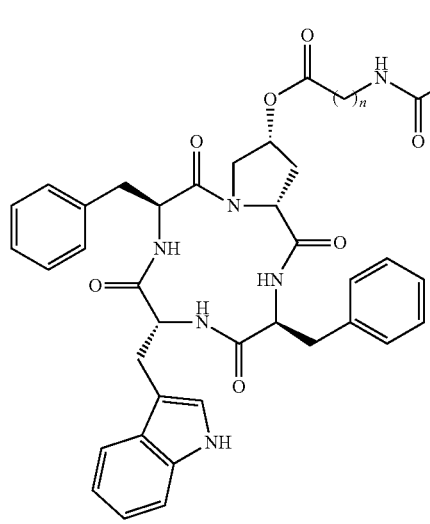

-continued
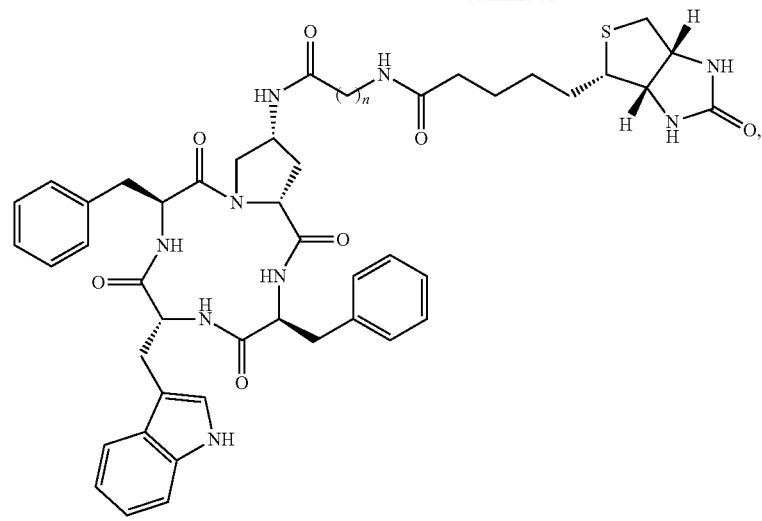
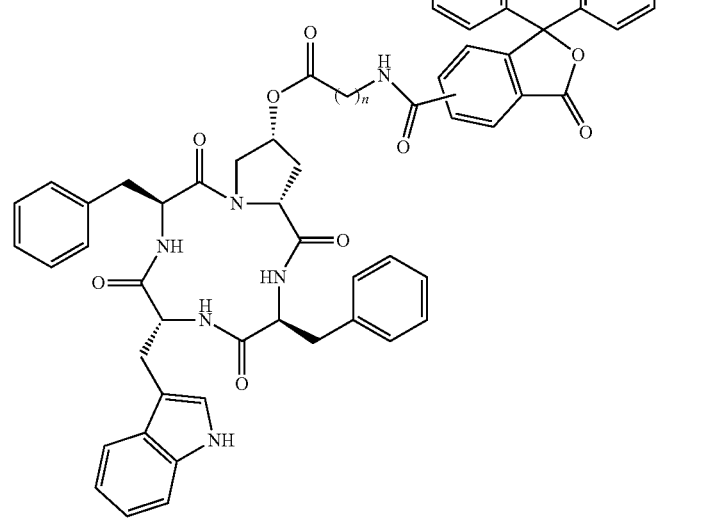
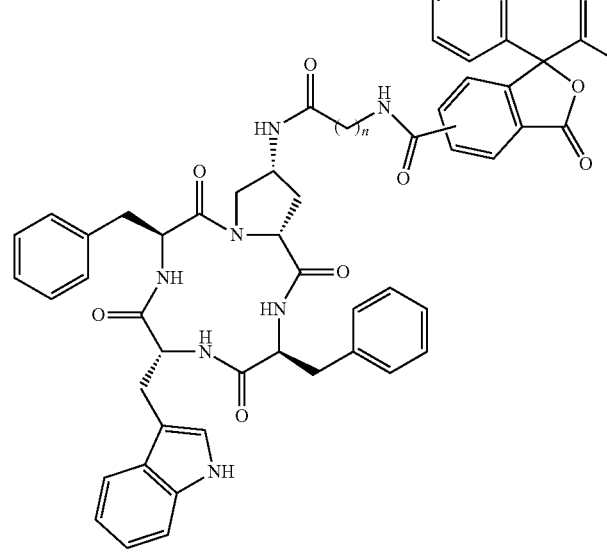

wherein each m is independently 0, 1, 2, 3, 4, 5, 6, 7, 8, 9, or 10; and each n is independently 0, 1, 2, 3, 4, 5, 6, 7, 8, 9, or 10; or a salt, solvate, hydrate or prodrug thereof.

In another aspect, the invention provides a compound of formula (3), wherein the compound is:

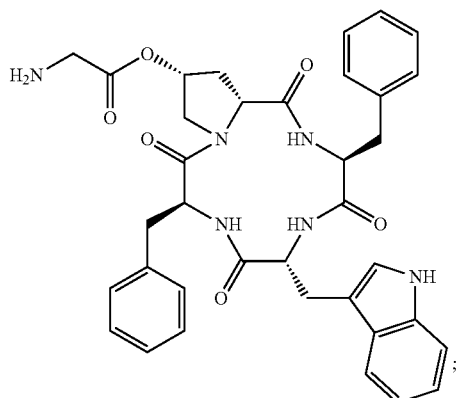

cyclo[Phe-cis-D-Hyp(Gly)²-Phe-D-Trp] (JVA 4102)

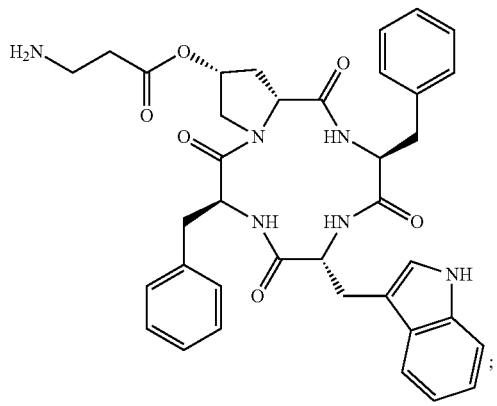

cyclo[Phe-cis-D-Hyp(β-Ala)²-Phe-D-Trp]

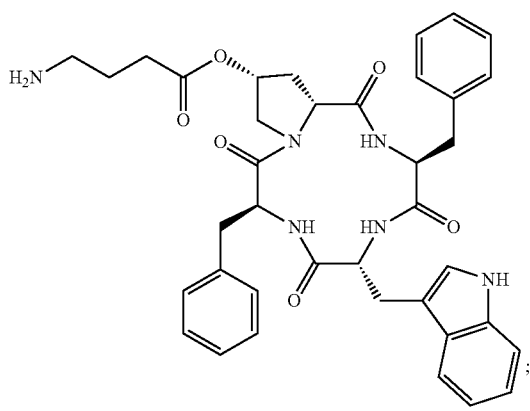

cyclo[Phe-cis-D-Hyp(γ-aminoisobutyric acid)²-Phe-D-Trp]

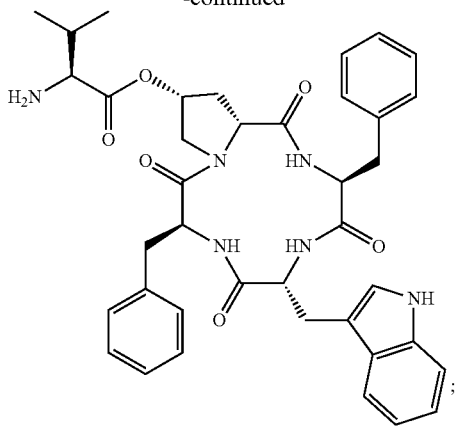

cyclo[Phe-cis-D-Hyp(Val)²-Phe-D-Trp]

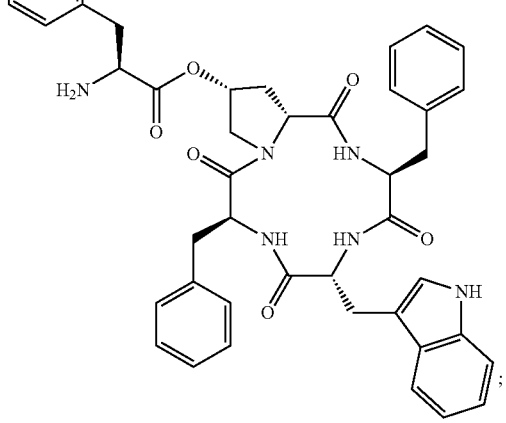

cyclo[Phe-cis-D-Hyp(Phe)²-Phe-D-Trp]

or a salt, solvate, hydrate or prodrug thereof.

In one aspect, the invention herein provides a compound of formula (1), (2), (3), (4), (5), (6), (7), (8), (9), (10), (11), (12), (13), (14), or (15), wherein the compound binds to an opioid receptor.

In another aspect, the invention herein provides a compound of formula (1), (2), (3), (4), (5), (6), (7), (8), (9), (10), (11), (12), (13), (14), or (15), wherein the compound binds to an opioid receptor, wherein the compound is a opioid receptor agonist. In certain embodiments the compound is a kappa opioid receptor agonist, a mu opioid receptor agonist, and a delta receptor agonist. In certain embodiments the compound is a kappa opioid receptor agonist. In certain embodiments the compound is a mu opioid receptor agonist. In certain embodiments the compound is a delta opioid receptor agonist.

In another aspect, the invention herein provides a compound of formula (1), (2), (3), (4), (5), (6), (7), (8), (9), (10), (11), (12), (13), (14), or (15), wherein the compound binds to an opioid receptor, wherein the compound is a opioid receptor antagonist. In certain embodiments the compound is a kappa opioid receptor antagonist, a mu opioid receptor antagonist, and a delta receptor antagonist. In certain embodiments the compound is a kappa opioid receptor antagonist. In certain embodiments the compound is a mu opioid receptor antagonist. In certain embodiments the compound is a delta opioid receptor antagonist.

In another aspect, the invention herein provides a compound of formula (1), (2), (3), (4), (5), (6), (7), (8), (9), (10), (11), (12), (13), (14), or (15), wherein the compound binds to an opioid receptor, wherein the compound is a mixed opioid receptor agonist/antagonist. In certain embodiments the compound is a mixed kappa opioid receptor agonist/antagonist, a mixed mu opioid receptor agonist/antagonist, and mixed a delta receptor agonist/antagonist. In certain embodiments the compound is a mixed kappa opioid receptor agonist/antagonist. In certain embodiments the compound is a mixed mu opioid receptor agonist/antagonist. In certain embodiments the compound is a mixed delta opioid receptor agonist/antagonist.

In one aspect, the invention provides a compound of formula (1), (2), (3), (4), (5), (6), (7), (8), (9), (10), (11), (12), (13), (14), or (15), wherein the compound binds to more than one opioid receptor. In certain embodiments, the compound acts on more than one opioid receptor. In certain embodiments, the compound binds to a first opioid receptor, a second opioid receptor, a third opioid receptor, or any combination thereof. In certain embodiments, the compound binds to a first opioid receptor and a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor. In certain embodiments, the compound binds to a third opioid receptor, wherein the third opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is an agonist of more than one opioid receptor. In certain embodiments, the compound is an agonist of a first opioid receptor, a second opioid receptor, a third opioid receptor, or any combination thereof. In certain embodiments, the compound is an agonist of a first opioid receptor and a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is an antagonist of more than one opioid receptor. In certain embodiments, the compound is an antagonist of a first opioid receptor, a second opioid receptor, a third opioid receptor, or any combination thereof. In certain embodiments, the compound is an antagonist of a first opioid receptor and a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is a mixed agonist/antagonist of more than one opioid receptor. In certain embodiments, the compound is a mixed agonist/antagonist of a first opioid receptor, a second opioid receptor, a third opioid receptor, or any combination thereof. In certain embodiments, the compound is a mixed agonist/antagonist of a first opioid receptor and a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is an agonist and an antagonist of one or more than one opioid receptor. In certain embodiments, the compound is an agonist of a first opioid receptor, a second opioid receptor, a third opioid receptor, or any combination thereof and an antagonist of a first opioid receptor, a second opioid receptor, a third opioid receptor, or any combination thereof. In certain embodiments, the compound is an agonist of a first opioid receptor and an antagonist of a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is an agonist and a mixed agonist/antagonist of one or more than one opioid receptor. In certain embodiments, the compound is an agonist of a first opioid receptor, a second opioid receptor, a third opioid receptor, or any combination thereof and a mixed agonist/antagonist of a first opioid receptor, a second opioid receptor, a third opioid receptor, or any combination thereof. In certain embodiments, the compound is an agonist of a first opioid receptor and a mixed agonist/antagonist of a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a compound of formula (1), (2), (3), (4), (5), (6), (7), (8), (9), (10), (11), (12), (13), (14), or (15), wherein the compound is an antagonist and a mixed agonist/antagonist of one or more than one opioid receptor. In certain embodiments, the compound is an antagonist of a first opioid receptor, a second opioid receptor, a third opioid receptor, or any combination thereof and a mixed agonist/antagonist of a first opioid receptor, a second opioid receptor, a third opioid receptor, or any combination thereof. In certain embodiments, the compound is an antagonist of a first opioid receptor and a mixed agonist/antagonist of a second opioid receptor, wherein the first opioid receptor is kappa opioid receptor, mu opioid receptor, or delta opioid receptor, and wherein the second opioid receptor is kappa opioid receptor, mu opioid receptor, or delta opioid receptor.

In one aspect, the invention provides a method of treating a disease, disorder, or symptom thereof in a subject, comprising administering to said subject a compound of any of the formulae herein.

In another aspect, the invention provides a method of treating a subject with a neurological disorder, psychiatric disorder, painful condition, or opioid receptor mediated disorder, or symptoms thereof, comprising administering to said subject in need thereof, an effective amount of a compound or pharmaceutical composition any of the formulae herein.

In another aspect, the invention provides a method of treating a subject with a neurological disorder or symptoms thereof, comprising administering to said subject in need thereof, an effective amount of a compound or pharmaceutical composition any of the formulae herein. In certain embodiments, the neurological disorder is addiction. In certain embodiments, the addiction is a drug addiction. In certain embodiments, the drug addiction is an opioid addiction. In certain embodiments, the drug addiction is a cocaine addiction. In certain embodiments, the addiction is an alcohol addiction.

In another aspect, the invention provides a method of treating a subject with a painful condition or symptoms thereof, comprising administering to said subject in need thereof, an effective amount of a compound or pharmaceutical composition any of the formulae herein. In certain embodiments, the painful condition is nociceptive pain. In certain embodiments, the painful condition is pain associated with withdrawal symptoms from a drug or alcohol addiction. In certain embodiments, the painful condition is pain associated with withdrawal symptoms from a drug addiction. In certain embodiments, the painful condition is pain associated with withdrawal symptoms from an alcohol addiction. In certain embodiments, the painful condition is pain associated with withdrawal symptoms from a cocaine addiction.

In another aspect, the invention provides a method of treating a subject in need of an analgesic, comprising administering to said subject in need thereof, an effective amount of a compound or pharmaceutical composition any of the formulae herein.

In another aspect, the invention provides a method of treating a subject with opioid receptor mediated disorder or symptoms thereof, comprising administering to said subject in need thereof, an effective amount of a compound or pharmaceutical composition any of the formulae herein. In certain aspects, the disorder is one wherein opioid receptor activity is upregulated (e.g., increased). In aspects, the disorder is one wherein opioid receptor activity is downregulated (e.g., decreased). In certain embodiments, the opioid receptor mediated disorder is stress-induced reinstatement of drug-seeking behavior. In certain embodiments, the opioid receptor mediated disorder is stress-induced reinstatement of drug-seeking behavior, wherein the drug-seeking behavior is cocaine-seeking behavior. In certain embodiments, the opioid receptor mediated disorder is stress-induced reinstatement of cocaine-seeking behavior. In certain embodiments, the opioid receptor mediated disorder is drug-induced reinstatement of drug-seeking behavior. In certain embodiments, the opioid receptor mediated disorder is drug-induced reinstatement of drug-seeking behavior, wherein the drug-seeking behavior is cocaine-seeking behavior. In certain embodiments, the opioid receptor mediated disorder is cocaine-induced reinstatement of cocaine-seeking behavior.

In another aspect, the invention provides a method of treating a subject with a proliferative disease or symptoms thereof, comprising administering to said subject in need thereof, an effective amount of a compound or pharmaceutical composition any of the formulae herein. In certain embodiments, the proliferative disorder is cancer. In certain embodiments, the proliferative disease is cancer, where the cancer harbors a mutation in c-Myc. In certain embodiments, the mutation in c-Myc results in c-Myc overexpression.

In another aspect, the invention provides a method of treating a subject with a psychiatric disorder or symptoms thereof, comprising administering to said subject in need thereof, an effective amount of a compound or pharmaceutical composition any of the formulae herein. In certain embodiments, the psychiatric disorder is a mood disorder. In certain embodiments, the psychiatric disorder is a substance abuse disorder. In certain embodiments, the substance abuse disorder is cocaine abuse disorder.

In one aspect, the invention provides method of treating a disease, disorder, or symptom thereof in a subject, comprising administering to said subject a compound of any of the formulae herein in combination with any other therapeutically effective compound or a pharmaceutical composition thereof.

In one aspect, the invention provides a method for determining the intracellular localization of a compound of any formulae disclosed herein, the method comprising contacting a cell with a compound of formula (15). In certain embodiments, the method for determining the intracellular localization of a compound of any formulae disclosed herein, the method comprising contacting a cell with a compound of formula (15), wherein the compound is:

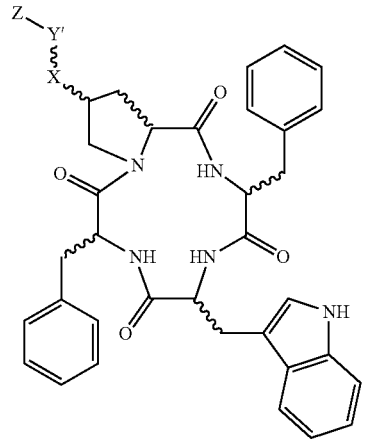

(15)

wherein, each X is independently —O or —NH;

each Y' is independently —CO(CH$_2$)$_n$NHZ or —COCH$_2$(OCH$_2$CH$_2$)$_m$NHZ;

Z is

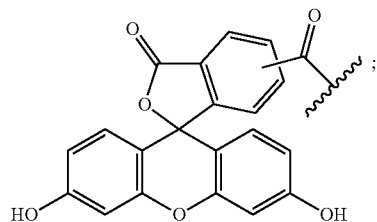

;

each m is independently 0, 1, 2, 3, 4, 5, 6, 7, 8, 9, or 10; and each n is independently 0, 1, 2, 3, 4, 5, 6, 7, 8, 9, or 10; or a salt, solvate, hydrate or prodrug thereof.

In one aspect, the invention provides a method for determining the intracellular localization of a compound of any formulae disclosed herein, the method comprising contacting a cell with a compound of formula (15). In certain embodiments, the method for determining the intracellular localization of a compound of any formulae disclosed herein, the method comprising contacting a cell with a compound of formula (15), wherein the compound is:

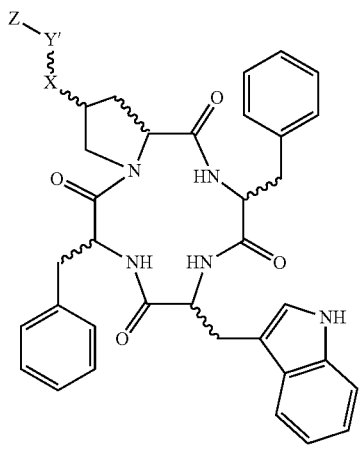

(15)

wherein, each X is independently —O or —NH;

each Y' is independently —CO(CH$_2$)$_n$NHZ or —COCH$_2$(OCH$_2$CH$_2$)$_m$NHZ;

Z is a fluorescent group (e.g.,

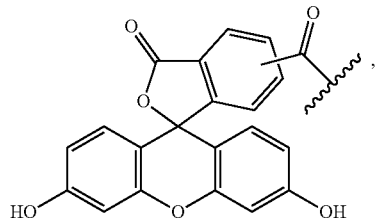

rhodamine or rhodamine derivative (e.g., tetraalkylrhodamines, and rhodamine analogs known in the art, e.g., available from commercial sources, such as Invitrogen);

each m is independently 0, 1, 2, 3, 4, 5, 6, 7, 8, 9, or 10; and each n is independently 0, 1, 2, 3, 4, 5, 6, 7, 8, 9, or 10; or a salt, solvate, hydrate or prodrug thereof.

In one aspect, the invention provides a method for determining the molecular target of a of a compound of any formulae disclosed herein, the method comprising contacting a cell with a compound of formula (15). In certain embodiments, the method for determining the molecular target of a compound of any formulae disclosed herein, the method comprising contacting a cell with a compound of formula (15), wherein the compound is:

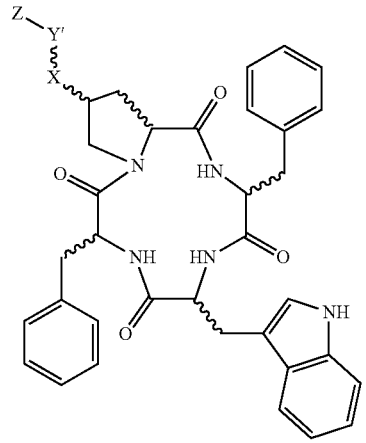

(15)

wherein, each X is independently —O or —NH;

each Y' is independently —CO(CH$_2$)$_n$NHZ or —COCH$_2$(OCH$_2$CH$_2$)$_m$NHZ;

Z is

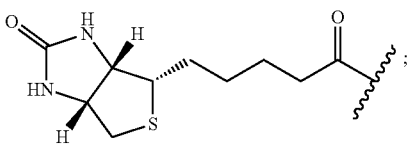 [SMILES: *C(=O)CCCC[C@@H]1SC[C@@H]2NC(=O)N[C@@H]21]

each m is independently 0, 1, 2, 3, 4, 5, 6, 7, 8, 9, or 10; and each n is independently 0, 1, 2, 3, 4, 5, 6, 7, 8, 9, or 10; or a salt, solvate, hydrate or prodrug thereof, wherein the cell is a cancer cell.

In one aspect, the invention provides a method for determining the molecular target of a of a compound of any formulae disclosed herein, the method comprising contacting a cell with a compound of formula (15). In certain embodiments, the method for determining the molecular target of a compound of any formulae disclosed herein, the method comprising contacting a cell with a compound of formula (15), wherein the compound is:

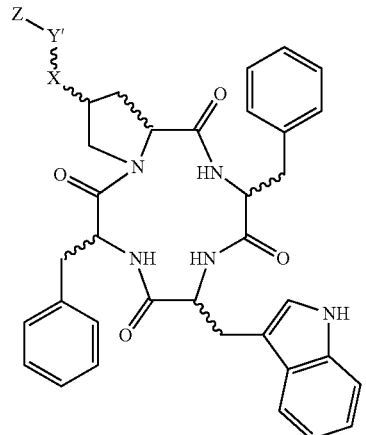

(15)

wherein,
each X is independently —O or —NH;
each Y' is independently —CO(CH$_2$)$_n$NHZ or —COCH$_2$(OCH$_2$CH$_2$)$_m$NHZ;
Z is

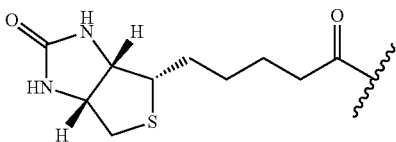 [SMILES: *C(=O)CCCC[C@@H]1SC[C@@H]2NC(=O)N[C@@H]21]

or a biotin derivative (e.g., desthiobiotin);
each m is independently 0, 1, 2, 3, 4, 5, 6, 7, 8, 9, or 10; and
each n is independently 0, 1, 2, 3, 4, 5, 6, 7, 8, 9, or 10;
or a salt, solvate, hydrate or prodrug thereof,
wherein the cell is a cancer cell.

BRIEF DESCRIPTION OF THE DRAWINGS

The present invention is further described below with reference to the following non-limiting examples and with reference to the following figures, in which.

DETAILED DESCRIPTION OF THE INVENTION

I. Definitions

Figure 1:
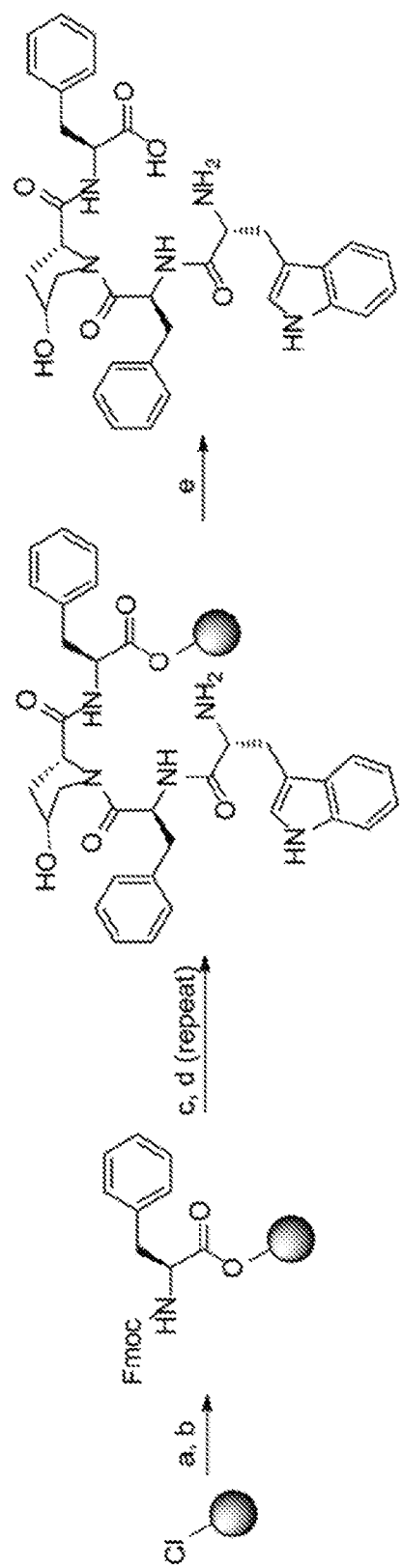
FIG. 1. shows Fmoc Solid-Phase peptide synthesis. The linear peptide was synthesized by Fmoc-based solid-phase peptide synthesis on a 2-chlorotrityl chloride resin. Unprotected Fmoc-cis-D-hydroxyproline was coupled in either the second or third position from the resin. The reagents used were as follows: a) Fmoc-Phe-OH, DIEA, 4:1 DCM/DMF, b) MeOH, DIEA, DCM, c) 20% 4-methylpiperidine, DMF, d) Fmoc-aa-OH, PyBOP, HOBt, DIEA, 1:1 DCM/DMF, and e) 1% TFA, DCM.
Figure 2:
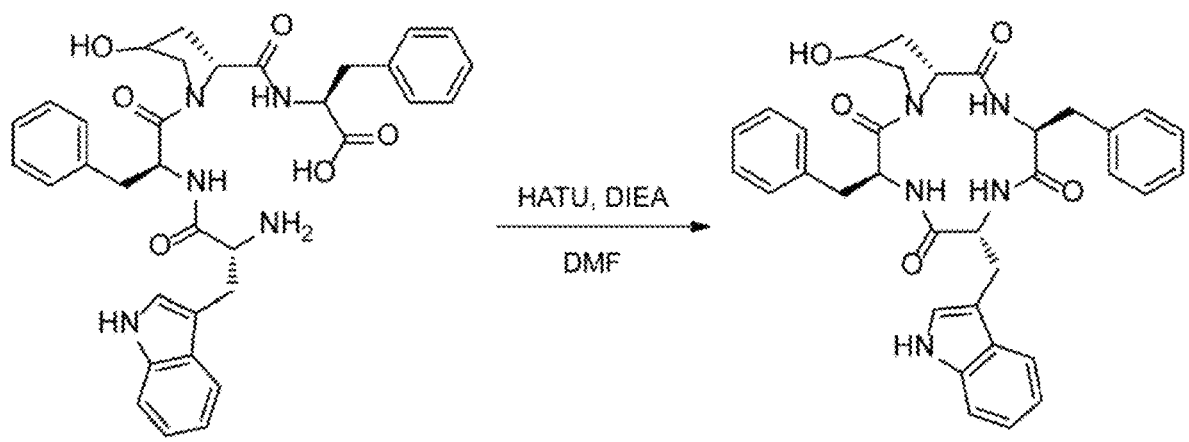
FIG. 2. shows peptide macrocyclization from the linear peptide precursor. The unpurified linear peptide was cyclized in solution at high dilution without side chain protection.

Before further description of the present invention, and in order that the invention may be more readily understood, certain terms are first defined and collected here for convenience.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

The term "isomers" or "stereoisomers" refers to compounds which have identical chemical constitution, but differ with regard to the arrangement of the atoms or groups in space.

The term "enantiomers" refers to two stereoisomers of a compound which are non-superimposable mirror images of one another. An equimolar mixture of two enantiomers is called a "racemic mixture" or a "racemate."

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

With respect to the nomenclature of a chiral center, terms "D" and "L" with respect to configuration are as defined by the IUPAC Recommendations. As to the use of the terms, diastereomer, racemate, epimer and enantiomer will be used in their normal context to describe the stereochemistry of preparations.

In a formula,  is a single bond where the stereochemistry of the moieties immediately attached thereto is not specified but can be any stereochemistry.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

Moreover, the term "alkyl" as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

The term "amino acid side chain" refers to the chemical moiety that is the side chain moiety of an amino acid (i.e., the chemical moiety attached to the alpha-carbon of the amino acid in addition to the —H, —COOH, —$NH_2$ groups). For example, amino acid side chains of the following exemplified amino acids are recited in parentheses thereafter: glycine (H); alanine (methyl); valine (isopropyl); leucine (isobutyl); phenylalanine (benzyl); proline (pyrrolidinyl—including nitrogen atom); serine (hydroxymethyl); cysteine (mercaptomethyl); tyrosine (4-hydroxyphenylmethyl).

The term "haloalkyl" is a substituted alkyl group, wherein one or more of the hydrogen atoms are independently replaced by a halogen, e.g., fluoro, bromo, chloro, or iodo. The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "sulfhydryl" or "thiol" means —SH.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The terms "alkenyl" and "alkynyl" refer to unsaturated aliphatic groups analogous in length and possible substitution to the alkyls described above, but that contain at least one double or triple bond, respectively.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl).

Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein. The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, C$_1$-C$_8$alkyl, C$_2$-C$_8$alkenyl, C$_2$-C$_8$alkynyl, C$_1$-C$_8$alkoxy, C$_2$-C$_5$alkyl ether, C$_3$-C$_8$alkanone, C$_1$-C$_8$alkylthio, amino, mono- or di-(C1-C$_8$alkyl)amino, haloC$_1$-C$_8$alkyl, haloC$_1$-C$_8$alkoxy, C$_1$-C$_8$alkanoyl, C$_2$-C$_8$alkanoyloxy, C$_1$-C$_8$alkoxycarbonyl, —COOH, —CONH$_2$, mono- or di-(C$_1$-C$_8$alkyl)aminocarbonyl, —SO$_2$NH$_2$, and/or mono or di(C$_1$-C$_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, methyl carbamate, ethyl carbamate, 9-fluorenylmethyl carbamate, 2,2,2-trichloroethyl carbamate, 2-trimethylsilylethyl carbamate, 2-phenylethyl carbamate, 1-(1-adamanthyl)-1-methylethyl carbamate, 2-chloroethyl carbamate, 1,1-dimethyl-2-haloethyl carbamate, 2-(2'-pyridyl)ethyl carbamate, 2-(4'-pyridyl)ethyl carbamate, 1-adamanthyl carbamate, 2-adamanthyl carbamate, vinyl carbamate, allyl carbamate, cinnamyl carbamate, 3-(3'-pyridyl)prop-2-enyl carbamate, N-hydroxypiperidinyl carbamate, alkyldithio carbamate, benzyl carbamate, p-methoxybenzyl carbamate, p-nitrobenzyl carbamate, 4-methylsulfinylbenzyl carbamate, diphenylmethyl carbamate, 2-methylthioethyl carbamate, 2-methylsulfonylethyl carbamate, 2-(4-nitrophenyl)ethyl carbamate, 3',5'-dimethoxybenzoin carbamate, acetamide, chloroacetamide, trifluoroacetamide, phenylacetamide, 3-phenylpropanamide, pent-4-enamide, 3-pyridylcarboxamide, benzamide, p-phenylbenzamide, N-phthalimide, N-tetrachlorophthalimide, 4-nitro-N-phthalimide, N-dithiasuccinimide, N-t-butylamine, N-allylamine, N-benzylamine, N-4-methoxybenzylamine, N-2,4-dimethoxybenzylamine, N-(diphenylmethyl)amine, N-5-dibenzosuberylamine, N-triphenylmethylamine, N-9-phenylfluorenylamine, N-1,1-dimethylthiomethyleneamine, N-benzylideneamine, benzenesulfonamide, p-toluenesulfonamide, 2- or 4-nitrobenzenesulfonamide, 2,4-dinitrobenzenesulfonamide, trifluoromethylsulfonamide, phenacylsulfonamide, N,N-dimethylsulfonamide, mesitylenesulfonamide, p-methoxyphenylsulfonamide, t-butoxycarbonyl, 9-fluorenylmethoxycarbonyl, benzyloxycarbonyl, and the like.

The term "thiol protecting group," as used herein, refers to a labile chemical moiety which is known in the art to protect a thiol group against undesired reactions during synthetic procedures. After said synthetic procedure(s) the amino protecting group as described herein may be selectively removed. Thiol protecting groups as known in the are described generally in T. H. Greene and P. G. M. Wuts, Protective Groups in Organic Synthesis, 3rd edition, John Wiley & Sons, New York (1999). Examples of thiol protecting groups include, but are not limited to, alkyl, benzyl, p-methoxybenzyl, p-nitrobenzyl, 2,4,6-trimethylbenzyl, 2,4,6-trimethoxybenzyl, diphenylmethyl, bis(4-methoxyphenyl)phenylmethyl, diphenyl-4-pyridyl, 2,4-dinitrophenyl, trifluoroacetyl, 9-fluorenylmethyl, t-butyl, triphenylmethyl, phenyl, methoxymethyl, benzyloxymethyl, alkylcarbonyl, benzoyl, trifluoroacetyl, t-butoxycarbonyl, 2,2,2-trichloroethoxycarbonyl, benzyloxycarbonyl, alkylaminocarbonyl, and the like.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2 H$_2$O) and hexahydrates (R.6 H$_2$O)).

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included.

The term "biotin" refers to a water soluble B vitamin comprised of a ureido ring fused with a tetrahydrothiophene ring. The term biotin also encompasses vitamin B7, vitamin H, and coenzyme R, nad biopiederm. The IUPAC name for biotin is 5-[(3aS,4S,6aR)-2-oxohexahydro-1H-thieno[3,4-d]imidazol-4-yl]pentanoic acid. Biotin is a coenzyme for carboxylase enzymes, involved in the synthesis of fatty acids, isoleucine, and valine, and in gluconeogenesis. Additionally, biotin is commonly used in a variety of biotechnology applications, including conjugating proteins or peptides for biochemical assays (e.g., biotinylation), assays employing biotin-streptavidin interactions, and assays employing biotin-avidin interactions, cell sorting, and enzyme-linked immunosorbent assays (ELISAs), among others. As used herein, the biotin can be obtained from any source (e.g., naturally derived or synthetically derived). Biotin may be conjugated to any peptide (e.g. macrocyclic peptide) or protein. In certain embodiments, biotin is a compound of formula

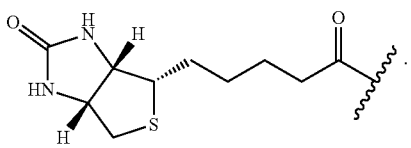 [SMILES: *C(=O)CCCC[C@@H]1SC[C@@H]2NC(=O)N[C@@H]21]

The term "carboxyfluorescein" refers to a molecule comprising fluorescein with an additional carboxyl group. The term carboxyfluorescein also encompasses 6-carboxyfluorescein, 6-FAM, 5-FAM, and 5(6)-carboxyfluorescein. Carboxyfluorescein is a fluorescent dye with an absorption wavelength of 495 nm and an emission wavelength of 517 nm. Carboxyfluorescein can be loaded into cells directly or conjugated to another molecule (e.g., a peptide or macrocyclic peptide) for intracellular delivery. Carboxyfluorescein is commonly employed as a reporter agent or dye to track the localization of a compound or cell (e.g. liposome tracking, tracking of cell division, compound microlocalization within a cell, etc.). In certain embodiments, carboxyfluorescein is a compound of formula

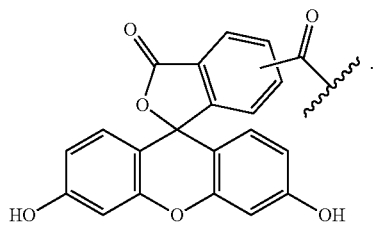

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins. Peptides can be derived naturally or synthetically. Peptides can contain natural and non-natural amino acids, e.g. synthetic amino acids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "receptor" refers to any protein molecule that receives a signal from outside or inside a cell. In general, receptors are membrane bound proteins. A receptor may be a peripheral membrane protein, an integral membrane protein, or any protein that interacts with the cellular membrane. A receptor may be comprised of a single protein or a complex of two or more proteins. Receptors induce a type of cellular response when a chemical signal or molecule binds to the receptor. A receptor may also refer to any drug target, such as an enzyme, transporter, or ion channel that is the target of a drug. In general, any molecule that binds to or interacts with a receptor is referred to as a ligand. Examples of receptors include, but are not limited to, ionotropic receptors, G-protein coupled receptors, receptor tyrosine kinases, and nuclear receptors.

The term "opioid receptor" refers to any inhibitory G protein-coupled receptor with an opioid as a ligand. The opioid receptor may be located presynaptically or postsynaptically. The opioid receptors referred to herein may be any of the major types of opioid receptors, including but not limited to the delta (δ) opioid receptor (DOR, $OP_1$), kappa (κ) opioid receptor (KOR, $OP_2$), mu (μ) opioid receptor (MOR, $OP_3$), nociceptin receptor (NOR, $OP_4$), and zeta (ζ) opioid receptor (ZOR). The term "opioid receptor" further encompasses any homomeric or heteromeric combination of the opioid receptors described above. The opioid receptors described herein include opioid receptors derived from any source or any tissue or cell type.

The term "delta opioid receptor" refers to the delta-1 opioid receptor ($\delta_1$) and delta-2 opioid receptor ($\delta_2$) and any combination or variation thereof. In certain aspects, delta opioid receptors are preferred. A delta opioid receptor can be located anywhere in the body, including the brain (e.g., pontine nucleus, amygdala, olfactory bulbs, and deep cortex). A delta opioid receptor mediates a variety of responses, including analgesia, euphoria, antidepressant effects, convulsant effects, and physical dependence.

The term "kappa opioid receptor" refers to the kappa-1 opioid receptor ($\kappa_1$), kappa-2 opioid receptor ($\kappa_2$), kappa-3 opioid receptor ($\kappa_3$) and any combination or variation thereof. In certain aspects, kappa opioid receptors are preferred. A kappa opioid receptor can be located anywhere in the body, including the brain (e.g., hypothalamus, periaqueductal gray, and claustrum) and spinal cord (e.g., substantia gelatinosa). A kappa opioid receptor mediates a variety of responses, including spinal analgesia, anticonvulsant effects, depression, dissociative effects, hallucinogenic effects, dysphoria, neuroprotection, stress, sedation, miosis, physical dependence, and diuresis.

The term "mu opioid receptor" refers to the mu-1 opioid receptor (i), mu-2 opioid receptor ($\mu_2$), mu-3 opioid receptor ($\mu_3$) and any combination or variation thereof. In certain aspects, mu opioid receptors are preferred. A mu opioid receptor can be located anywhere in the body, including the brain (e.g., laminae III of the cortex, laminae IV of the cortex, thalamus, and periaqueductal gray) and spinal cord (e.g., substantia gelatinosa). A mu opioid receptor mediates a variety of responses, including supraspinal analgesia, physical dependence, respiratory depression, miosis, euphoria, vasodilation, and reduced gastrointestinal motility.

The term "nociceptin opioid receptor" refers to the nociceptin-1 opioid receptor ($ORL_1$) and any combination or variation thereof. A nociceptin opioid receptor can be located anywhere in the body, including brain (e.g., cirtex, amygdala, hippocampus, septal nuclei, habenula, and hypothalamus) and the spinal cord. A nociceptin opioid receptor mediates a variety of responses, including anxiety, depression, appetite, and development of tolerance to mu-opioid agonists.

The term "zeta opioid receptor" refers to any zeta opioid receptor (ZOR) and any combination or variation thereof. A zeta opioid receptor can be located anywhere in the body, including the heart, liver, skeletal muscle, kidney, brain, pancreas, and fetal tissue (e.g., liver and kidney). A zeta opioid receptor mediates a variety of responses, including tissue growth, embryonic development, and regulation of cell proliferation (e.g. cancer cell proliferation).

The term "ligand" refers to any molecule of any composition that interacts with a biomolecule, protein, or receptor. Ligands typically form a complex with a biomolecule, protein, or receptor to serve a biological purpose. Binding of a ligand typically results in a change in conformation of the target biomolecule. A ligand can be a small molecule, a peptide, an ion, a protein, an amino acid, a polymer, a nucleotide, a nucleic acid, DNA, RNA, or any derivatives thereof. The term "ligand" encompasses agonists, partial agonists, mixed agonist-antagonists, antagonists, inverse agonists, and allosteric modulators, among others. In certain embodiments, the ligand is a macrocyclic peptide comprising between 2 to 20 amino acids. In certain embodiments, the ligand is a macrocyclic tetrapeptide (i.e. 4 amino acids). In certain embodiments, the ligand is cyclo(Phe-D-Pro-Phe-L-Trp) or CJ-15,208. In certain embodiments, the ligand is cyclo(Phe-D-Pro-Phe-D-Trp) or [D-Trp]CJ-15,208. In certain embodiments, the ligand is any derivative of cyclo(Phe-D-Pro-Phe-L-Trp) or CJ-15,208. In certain embodiments, the ligand is any derivative of cyclo(Phe-D-Pro-Phe-D-Trp) or [D-Trp]CJ-15,208. In certain embodiments, the ligand is cyclo(Phe-D-Hyd-Phe-L-Trp) or any derivative thereof. In certain embodiments, the ligand is cyclo(Phe-D-Hyd-Phe-D-Trp) or any derivative thereof. In certain embodiments, the ligand is cyclo[Phe-cis-D-Hyp(Gly)$^2$-Phe-D-Trp] (JVA 4102), or any derivative thereof. In certain embodiments, the ligand is cyclo[Phe-cis-D-Hyp(β-Ala)$_2$-Phe-D-Trp], or any derivative thereof. In certain embodiments, the ligand is cyclo[Phe-cis-D-Hyp(γ-aminoisobutyric acid)$_2$-Phe-D-Trp], or any derivative thereof. In certain embodiments, the ligand is cyclo[Phe-cis-D-Hyp(Val)$_2$-Phe-D-Trp], or any derivative thereof. In certain embodiments, the ligand is cyclo[Phe-cis-D-Hyp(Phe)$^2$-Phe-D-Trp], or any derivative thereof. In certain embodiments, the ligand is a compound of formula (1), (2), (3), (4), (5), (6), (7), (8), (9), (10), (11), (12), (13), (14), (15) or any derivative thereof.

The term "agonist" refers to any chemical or molecule that binds either reversibly or irreversible to a receptor and activates said receptor to produce a biological response. An agonist further refers to any chemical or molecule that causes an action or outcome (e.g., within a cell) as a result of binding to or interacting with a receptor. An agonist can be an endogenous agonist that is naturally produced by the body (e.g., a hormone or neurotransmitter) or an exogenous agonist (e.g., a drug). An agonist further encompasses all types of agonists, including superagonists, full agonists, partial agonists, silent agonists, partial inverse agonists, full inverse agonists, co-agonists, and irreversible agonists. In certain embodiments, the agonist is a peptide comprising between 1-20 amino acids. In certain embodiments, the agonist is a macrocyclic peptide comprising between 1-20 amino acids. In certain embodiments, the agonist is a macrocyclic tetrapeptide (i.e. 4 amino acids). In certain embodiments, the agonist is cyclo(Phe-D-Pro-Phe-L-Trp) or CJ-15,208. In certain embodiments, the agonist is cyclo (Phe-D-Pro-Phe-D-Trp) or [D-Trp]CJ-15,208. In certain embodiments, the agonist is any derivative of cyclo(Phe-D-Pro-Phe-L-Trp) or CJ-15,208. In certain embodiments, the agonist is any derivative of cyclo(Phe-D-Pro-Phe-D-Trp) or [D-Trp]CJ-15,208. In certain embodiments, the agonist is cyclo(Phe-D-Hyd-Phe-L-Trp) or any derivative thereof. In certain embodiments, the agonist is cyclo(Phe-D-Hyd-Phe-D-Trp) or any derivative thereof. In certain embodiments, the agonist is cyclo[Phe-cis-D-Hyp(Gly)$^2$-Phe-D-Trp] (JVA 4102), or any derivative thereof. In certain embodiments, the agonist is cyclo[Phe-cis-D-Hyp(β-Ala)$^2$-Phe-D-Trp], or any derivative thereof. In certain embodiments, the agonist is cyclo[Phe-cis-D-Hyp(γ-aminoisobutyric acid)$^2$-Phe-D-Trp], or any derivative thereof. In certain embodiments, the agonist is cyclo[Phe-cis-D-Hyp(Val)$^2$-Phe-D-Trp], or any derivative thereof. In certain embodiments, the agonist is cyclo[Phe-cis-D-Hyp(Phe)$^2$-Phe-D-Trp], or any derivative thereof. In certain embodiments, the agonist is any compound of any formula described herein. In certain embodiments, the agonist is a compound of formula (1), (2), (3), (4), (5), (6), (7), (8), (9), (10), (11), (12), (13), (14), (15) or any derivative thereof.

The term "antagonist" refers to any chemical or molecule that binds either reversibly or irreversible to a receptor and blocks or reduces a biological response from said receptor. An antagonist further refers to any chemical or molecule that blocks or reduces an action or outcome (e.g., within a cell) as a result of binding to or interacting with a receptor. Antagonists may be referred to as blockers (e.g., alpha blockers, beta blockers, calcium channel blockers, etc.). An antagonist is any chemical or molecule that has affinity but no efficacy for a receptor. An antagonist can block the action of an agonist. An antagonist can bind to any location of the receptor (e.g., to an active site, an allosteric site, or any binding site not involved in the regulation of a receptor's activity). An antagonist can be an endogenous agonist that is naturally produced by the body (e.g., a hormone or neurotransmitter) or an exogenous antagonist (e.g., a drug). In certain embodiments, the antagonist is a peptide comprising between 1-20 amino acids. In certain embodiments, the antagonist is a macrocyclic peptide comprising between 1-20 amino acids. In certain embodiments, the antagonist is a macrocyclic tetrapeptide (i.e. 4 amino acids). In certain embodiments, the antagonist is cyclo(Phe-D-Pro-Phe-L-Trp) or CJ-15,208. In certain embodiments, the antagonist is cyclo(Phe-D-Pro-Phe-D-Trp) or [D-Trp]CJ-15,208. In certain embodiments, the antagonist is any derivative of cyclo (Phe-D-Pro-Phe-L-Trp) or CJ-15,208. In certain embodiments, the antagonist is any derivative of cyclo(Phe-D-Pro-Phe-D-Trp) or [D-Trp]CJ-15,208. In certain embodiments, the antagonist is cyclo(Phe-D-Hyd-Phe-L-Trp) or any derivative thereof. In certain embodiments, the antagonist is cyclo(Phe-D-Hyd-Phe-D-Trp) or any derivative thereof. In certain embodiments, the antagonist is cyclo[Phe-cis-D-Hyp (Gly)$^2$-Phe-D-Trp] (JVA 4102), or any derivative thereof. In certain embodiments, the antagonist is cyclo[Phe-cis-D-Hyp (β-Ala)$^2$-Phe-D-Trp], or any derivative thereof. In certain embodiments, the antagonist is cyclo[Phe-cis-D-Hyp(γ-aminoisobutyric acid)$^2$-Phe-D-Trp], or any derivative thereof. In certain embodiments, the antagonist is cyclo[Phe-cis-D-Hyp (Val)$^2$-Phe-D-Trp], or any derivative thereof. In certain embodiments, the antagonist is cyclo[Phe-cis-D-Hyp(Phe)$^2$-Phe-D-Trp], or any derivative thereof. In certain embodiments, the antagonist is any compound of any formula described herein. In certain embodiments, the antagonist is a compound of formula (1), (2), (3), (4), (5), (6), (7), (8), (9), (10), (11), (12), (13), (14), (15) or any derivative thereof.

The term "mixed agonist/antagonist" refers to any chemical or molecule that has the properties and/or functions of both an agonist and an antagonist. A mixed agonist/antagonist can be an endogenous mixed agonist/antagonist that is naturally produced by the body (e.g., a hormone or neurotransmitter) or an exogenous mixed agonist/antagonist (e.g., a drug). In certain embodiments, the mixed agonist/antagonist is a peptide comprising between 1-20 amino acids. In certain embodiments, the mixed agonist/antagonist is a macrocyclic peptide comprising between 1-20 amino acids. In certain embodiments, the mixed agonist/antagonist is a macrocyclic tetrapeptide (i.e. 4 amino acids). In certain embodiments, the mixed agonist/antagonist is cyclo(Phe-D-Pro-Phe-L-Trp) or CJ-15,208. In certain embodiments, the mixed agonist/antagonist is cyclo(Phe-D-Pro-Phe-D-Trp) or [D-Trp]CJ-15,208. In certain embodiments, the mixed agonist/antagonist is any derivative of cyclo(Phe-D-Pro-Phe-L-Trp) or CJ-15,208. In certain embodiments, the mixed agonist/antagonist is any derivative of cyclo(Phe-D-Pro-Phe-D-Trp) or [D-Trp]CJ-15,208. In certain embodiments, the mixed agonist/antagonist is cyclo(Phe-D-Hyd-Phe-L-Trp) or any derivative thereof. In certain embodiments, the mixed agonist/antagonist is cyclo(Phe-D-Hyd-Phe-D-Trp) or any derivative thereof. In certain embodiments, the mixed agonist/antagonist is cyclo[Phe-cis-D-Hyp(Gly)$^2$-Phe-D-Trp] (JVA 4102), or any derivative thereof. In certain embodiments, the mixed agonist/antagonist is cyclo[Phe-cis-D-Hyp(1-Ala)$_2$-Phe-D-Trp], or any derivative thereof. In certain embodiments, the mixed agonist/antagonist is cyclo [Phe-cis-D-Hyp(γ-aminoisobutyric acid)$_2$-Phe-D-Trp], or any derivative thereof. In certain embodiments, the mixed agonist/antagonist is cyclo[Phe-cis-D-Hyp(Val)$_2$-Phe-D-Trp], or any derivative thereof. In certain embodiments, the mixed agonist/antagonist is cyclo [Phe-cis-D-Hyp(Phe)$^2$-Phe-D-Trp], or any derivative thereof. In certain embodiments, the mixed agonist/antagonist is any compound of any formula described herein. In certain embodiments, the mixed agonist/antagonist is a compound of formula (1), (2), (3), (4), (5), (6), (7), (8), (9), (10), (11), (12), (13), (14), (15) or any derivative thereof.

The terms "condition," "disease," and "disorder" are used interchangeably.

The terms "agent" and "compound" are used interchangeably.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route.

For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a prodrug form which is converted into its active metabolite, or more active metabolite in vivo.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In one embodiment, a suitable biological composition or biological sample is a cell. In one embodiment, a suitable biological composition or biological sample is a mammalian cell. In one embodiment, a suitable biological composition or biological sample is a cancer cell.

The term "effective amount" includes an amount effective, at dosages and for periods of time necessary, to achieve the desired result, e.g., sufficient to treat a opioid receptor mediated disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

The language "improved biological properties" refers to any activity inherent in a compound of the invention that enhances its effectiveness in vivo. In certain embodiments, this term refers to any qualitative or quantitative improved therapeutic property of a compound of the invention, such as reduced toxicity.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The language "reduced toxicity" is intended to include a reduction in any undesired side effect elicited by a compound of the invention when administered in vivo.

The term "subject" includes organisms which are capable of suffering from a disease defined here or who could otherwise benefit from the administration of a compound of the invention, such as human and non-human animals. Preferred humans include human patients with a cell proliferative disorder, neurological disorder, psychiatric disorder, cancer, opioid receptor mediated disorder, addiction or associated state, as described herein. The term "non-human animals" of the invention includes all vertebrates, e.g., mammals; e.g., rodents; e.g., mice; and non-mammals, such as non-human primates; e.g., sheep, dog, cow, chickens, amphibians, reptiles, etc.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention refers to an amount of an agent which is effective, upon single or multiple dose administration to the patient, in mediating the symptoms of an opioid receptor mediated disorder, or in prolonging the survivability of the patient with such a opioid receptor mediated disorder beyond that expected in the absence of such treatment. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for binding an opioid receptor and acting as an antagonist against said opioid receptor. In certain embodiments, a therapeutically effective amount is an amount sufficient for binding to a kappa opioid receptor (KOR), a delta opioid receptor (DOR), a mu opioid receptor (MOR), or any combination thereof and acting as an antagonist against said kappa opioid receptor (KOR), delta opioid receptor (DOR), mu opioid receptor (MOR), or any combination thereof. In certain embodiments, a therapeutically effective amount is an amount sufficient for binding to a kappa opioid receptor (KOR) and acting as an antagonist against said kappa opioid receptor (KOR). In certain embodiments, a therapeutically effective amount is an amount sufficient for binding to a mu opioid receptor (MOR) and acting as an antagonist against said mu opioid receptor (MOR). In certain embodiments, a therapeutically effective amount is an amount sufficient for binding to a delta opioid receptor (DOR) and acting as an antagonist against said delta opioid receptor (DOR). In certain embodiments, a therapeutically effective amount is an amount sufficient for binding to a kappa opioid receptor (KOR) and acting as an antagonist against said kappa opioid receptor (KOR) is preferred. In certain embodiments, a therapeutically effective amount is an amount sufficient for binding an opioid receptor and acting as an agonist against said opioid receptor. In certain embodiments, a therapeutically effective amount is an amount sufficient for binding to a kappa opioid receptor (KOR), a delta opioid receptor (DOR), a mu opioid receptor (MOR), or any combination thereof and acting as an agonist against said kappa opioid receptor (KOR), delta opioid receptor (DOR), mu opioid receptor (MOR), or any combination thereof. In certain embodiments, a therapeutically effective amount is an amount sufficient for binding to a kappa opioid receptor (KOR) and acting as an agonist against said kappa opioid receptor (KOR). In certain embodiments, a therapeutically effective amount is an amount sufficient for binding to a mu opioid receptor (MOR) and acting as an agonist against said mu opioid receptor (MOR). In certain embodiments, a therapeutically effective amount is an amount sufficient for binding to a delta opioid receptor (DOR) and acting as an agonist against said delta opioid receptor (DOR). In certain embodiments, a therapeutically effective amount is an amount sufficient for binding to a kappa opioid receptor (KOR) and acting as an agonist against said kappa opioid receptor (KOR) is preferred. In certain embodiments, a therapeutically effective amount is an amount sufficient for binding an opioid receptor and acting as a mixed agonist/antagonist against said opioid receptor. In certain embodiments, a therapeutically effective amount is an amount sufficient for binding to a kappa opioid receptor (KOR), a delta opioid receptor (DOR), a mu opioid receptor (MOR), or any combination thereof and acting as a mixed agonist/antagonist against said kappa opioid receptor (KOR), delta opioid receptor (DOR), mu opioid receptor (MOR), or any combination thereof. In certain embodiments, a therapeutically effective amount is an amount sufficient for binding to a kappa opioid receptor (KOR) and acting as a mixed agonist/antagonist against said kappa opioid receptor (KOR). In certain embodiments, a therapeutically effective amount is an amount sufficient for binding to a mu opioid receptor (MOR) and acting as a mixed agonist/antagonist against said mu opioid receptor (MOR). In certain embodiments, a therapeutically effective amount is an amount sufficient for binding to a delta opioid receptor (DOR) and acting as a mixed agonist/antagonist against said delta opioid receptor (DOR). In certain embodiments, a therapeutically effective amount is an amount sufficient for binding to a kappa opioid receptor (KOR) and acting as a mixed agonist/antagonist against said kappa opioid receptor (KOR) is preferred. In certain embodiments, a therapeutically effective amount is an amount sufficient for treating or alleviating pain or suffering in an subject with a disease (e.g., AIDS, cancer, lung disease, heart disease, brain disease, mood disorders, and diseases or disorders involving the central nervous system). In certain embodiments, a therapeutically effective amount is an amount sufficient for treating a drug or alcohol addiction. In certain embodiments, a therapeutically effective amount is an amount sufficient for treating drug or alcohol abuse. In certain embodiments, a therapeutically effective amount is an amount sufficient for treating cocaine addiction. In certain embodiments, a therapeutically effective amount that is an amount sufficient for treating cocaine addiction is preferred. In certain embodiments, a therapeutically effective amount is an amount sufficient for treating a stress-induced disorder. In certain embodiments, a therapeutically effective amount is an amount sufficient for treating chronic relapsing disorder. In certain embodiments, a therapeutically effective amount is an amount sufficient for treating or reducing drug-seeking behavior. In certain embodiments, a therapeutically effective amount is an amount sufficient for treating or reducing stress-induced drug-seeking behavior. In certain embodiments, a therapeutically effective amount is an amount sufficient for treating stress-induced reinstatement of cocaine-seeking behavior. In certain embodiments, a therapeutically effective amount that is an amount sufficient for treating cocaine addiction is preferred. In certain embodiments, a therapeutically effective amount that is an amount sufficient for treating or reducing drug-seeking behavior is preferred. In certain embodiments, a therapeutically effective amount that is an amount sufficient for treating stress-induced reinstatement of cocaine-seeking behavior is preferred. In certain embodiments, a therapeutically effective amount is an amount sufficient for treating a drug or alcohol addiction as a result of increased opioid receptor activity. In certain embodiments, a therapeutically effective amount is an amount sufficient for treating a drug or alcohol addiction as a result of increased opioid receptor activity. In certain embodiments, a therapeutically effective amount is an amount sufficient for treating a drug or alcohol addiction as a result of reduced opioid receptor activity. In certain embodiments, a therapeutically effective amount is an amount sufficient for treating stress-induced reinstatement of cocaine-seeking behavior as a result of increased opioid receptor activity. Preferably, a therapeutically effective amount is an amount sufficient for treating stress-induced reinstatement of cocaine-seeking behavior as a result of increased kappa opioid receptor (KOR) activity. In certain embodiments, a therapeutically effective amount is an amount sufficient for treating drug-primed reinstatement of drug-seeking behavior as a result of decreased opioid receptor activity. In certain embodiments, a therapeutically effective amount is an amount sufficient for treating cocaine-primed reinstatement of cocaine-seeking behavior as a result of decreased opioid receptor activity. Preferably, a therapeutically effective amount is an amount sufficient for treating cocaine-primed reinstatement of cocaine-seeking behavior as a result of reduced kappa opioid receptor (KOR) activity.

The language "stress-induced reinstatement of cocaine-seeking behavior" refers to cocaine-seeking behavior that is promoted by stress. In general, stress increases the endogenous levels of dynophroin (Dyn). Dyn is the endogenous ligand of the kappa opioid receptor (KOR).

The language "drug-induced reinstatement of drug-seeking behavior" refers to drug-seeking behavior that is promoted by exposure to a small dose of the drug.

The language "cocaine-induced reinstatement of cocaine-seeking behavior" refers to cocaine-seeking behavior that is promoted by exposure to a small dose of cocaine.

The language "opioid receptor mediated disorder" refers to any disease or disorder caused by upregulation (e.g., increased function) or downregulation (e.g., decreased function) of opioid receptor function. An opioid receptor mediated disorder includes neurological disorders, painful conditions, cancer, and psychiatric disorders. An opioid receptor mediated disorder includes stress-induced reinstatement of drug-seeking behavior and drug-induced reinstatement of drug-seeking behavior. In certain embodiments, the stress-induced reinstatement of drug-seeking behavior is stress-induced reinstatement of cocaine-seeking behavior. In certain embodiments, the drug-induced reinstatement of drug-seeking behavior is cocaine-induced reinstatement of cocaine-seeking behavior. In certain embodiments, drug-induced reinstatement of drug-seeking behavior that is cocaine-induced reinstatement of cocaine-seeking behavior is preferred. In certain embodiments, stress-induced reinstatement of drug-seeking behavior that is stress-induced reinstatement of cocaine-seeking behavior is preferred.

The term "reinstatement" and "relapse" can be used interchangeably (e.g., are synonyms).

The language "opioid activity" refers to any activity that is associated with an opioid receptor. Opioid activity may refer to a molecule acting as an agonist, an antagonist, or mixed agonist/antagonist.

The language "acting as an antagonist" refers to any molecule, ligand, or compound that performs the function of an "antagonist," as defined above.

The language "acting as an agonist" refers to any molecule, ligand, or compound that performs the function of an "agonist," as defined above.

The language "acting as a mixed agonist/antagonist" refers to any molecule, ligand, or compound that performs the function of a "mixed agonist/antagonist," as defined above.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases. In certain embodiments, a proliferative disease that is cancer is preferred.

In certain embodiments, the proliferative disease is characterized by an overexpression of Myc. The overexpression of Myc is further characterized by a higher than normal expression level (e.g., basal expression level) of Myc. In certain embodiments, the proliferative disease is characterized by an overexpression of c-Myc. In certain embodiments, a proliferative disease characterized by an overexpression of c-Myc is preferred.

The term "angiogenesis" refers to the physiological process through which new blood vessels form from preexisting vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "premalignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue. In certain embodiments, a tumor that overexpressed c-Myc is preferred.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemial-lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the cancer is characterized by an overexpression of Myc. The overexpression of Myc is further characterized by a higher than normal expression level (e.g., basal expression level) of Myc. In certain embodiments, the cancer is characterized by an overexpression of c-Myc. In certain embodiments, a cancer characterized by an overexpression of c-Myc is preferred.

The term "Myc" refers to the protein encoded by the MYC gene. The transcription factor Myc is a multifunctional nuclear phosphoprotein that plays a role in cell cycle progression, apoptosis, and cellular transformation processes. Myc is a member of the Myc family of proteins. The Myc family of proteins (e.g., transcription factors) also includes c-Myc, n-Myc and 1-Myc. Myc interacts with DNA using its basic helix-loop-helix (bHLH) domain and interacts with its binding partner Max using its leucine-zipper motif. A mutated version of Myc is found in a variety of cancers. In general, a mutation in Myc causes constitutive (e.g. persistent) expression (e.g., overexpression) of Myc, leading to the unregulated expression of many genes (e.g., those involved in cell cycle proliferation). Myc mutations are found in multiple types of cancers, including cervical, colon, breast, stomach, and lung carcinomas and Burkitt lymphoma. In certain embodiments, Myc that is c-Myc is preferred.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome;

Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome. In certain embodiments, a neurological disease that is addiction is preferred.

A "painful condition" includes, but is not limited to, neuropathic pain (e.g., peripheral neuropathic pain), central pain, deafferentation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition. In certain embodiments, a painful condition that is nociceptive pain is preferred. In certain embodiments, a painful condition that is pain associated with withdrawal symptoms from drug addiction is preferred. In certain embodiments, the condition is associated with withdrawal symptoms from drug addiction.

In certain embodiments, the painful condition is nociceptive pain. The term "nociceptive pain" refers to pain resulting from stimulation of nociceptive receptors. Nociceptive pain also includes pain resulting from the alteration of nociception as a result of alteration of opioid receptor function.

In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., post-herpetic neuralgia, trigeminal neuralgia); pain resulting from physical trauma (e.g., amputation; surgery, invasive medical procedures, toxins, burns, infection), pain resulting from cancer or chemotherapy (e.g., chemotherapy-induced pain such as chemotherapy-induced peripheral neuropathy), and pain resulting from an inflammatory condition (e.g., a chronic inflammatory condition).

Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia). [00449] In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder.

The term "addiction" refers to a disease of the mind characterized by compulsive engagement in rewarding or addictive stimuli. An addiction often involved addictive stimuli that are reinforcing (e.g., increase the likelihood that a person will seek repeated exposure to the agent causing the stimulus) and intrinsically rewarding (e.g., they are perceived by a person as being inherently desirable, positive, and pleasurable). The addiction may arise through transcriptional or epigenetic mechanisms and generally develops over time as a result of persistent exposure to addictive stimulus or stimuli. Cognitive control, particularly inhibitory control over behavior, is impaired in a person suffering from addiction. Additionally, stimulus-driven behavioral responses (i.e., stimulus control) that are associated with a particular rewarding stimulus tend to dominate the behavior of a person suffering from addiction. The term addiction encompasses addiction to drugs (e.g., cocaine, morphine, opioids, and the like), alcohol, gambling, etc. In certain embodiments, an addiction that is a drug addiction is preferred. In certain embodiments, an addiction that is a cocaine addiction is preferred.

The term "psychiatric disorder" refers to a disease of the mind and includes diseases and disorders listed in the Diagnostic and Statistical Manual of Mental Disorders-Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The present disclosure provides pharmaceutical compositions comprising a compound of formula (1), (2), (3), (4), (5), (6), (7), (8), (9), (10), (11), (12), (13), (14), (15) or any derivative thereof, or a pharmaceutically acceptable salt thereof, and optionally a pharmaceutically acceptable excipient. In certain embodiments, the pharmaceutical composition described herein comprises a compound of formula (1), (2), (3), (4), (5), (6), (7), (8), (9), (10), (11), (12), (13), (14), (15) or any derivative thereof, or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is an amount effective for treating a proliferative disease in a subject in need thereof. In certain embodiments, the effective amount is an amount effective for treating a neurological disease in a subject in need thereof. In certain embodiments, the effective amount is an amount effective for treating a opioid receptor mediated disorder in a subject in need thereof. In certain embodiments, the effective amount is an amount effective for treating an addiction in a subject in need thereof. In certain embodiments, the effective amount is an amount effective for treating a mood disorder in a subject in need thereof.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

II. Compounds of the Invention

Compounds delineated herein include salts, hydrates, solvates and prodrugs thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jihnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. For example, compounds of formulae herein can be made using methodology known in the art, including Eans, S. O., Ganno, M. L., Reilley, K. J., Patkar, K. A., Senadheera, S. N., Aldrich, J. V., and McLaughlin, J. P. (2013) The macrocyclic tetrapeptide (D-Trp)CJ15,208 produces short-acting κ opioid receptor antagonism in the CNS after oral administration Br J Pharmacol 169, 426-436; and Ross, N. C., Kulkarni, S. S., McLaughlin, J. P., and Aldrich, J. V. (2010) Synthesis of CJ-15,208, a novel K-opioid receptor antagonist Tetrahedron Lett 51, 5020-5023.

The compounds of the formulae herein can be synthesized using methodology similar to that shown in the following schemes.

Scheme I illustrates the synthesis of the macrocyclic peptide cyclo(Phe-cis-D-Hyp-Phe-D-Trp) (G) from the linear peptide F by Fmoc-based solid phase peptide synthesis (SPPS) on 2-chlorotrityl resin. The 2-chlorotrityl resin was loaded with 4 equivalents of Fmoc-protected phenylalanine (Fmoc-Phe-OH) using 8 equivalents N,N-diisopropylethylamine (DIEA) over 6 hours to give A. Fmoc quantitation was performed to determine loading efficiency. The remainder of the linear peptide was synthesized according to standard coupling and deprotection protocols. Deprotection of the terminal amino acid is carried out in the presence of a mild base, e.g., 20% 4-methylpiperidine, and 1-hydroxybenzotriazole (HOBt), benzotriazol-1-yl-oxy-tris(pyrrolidino)phosphonium hexafluorophosphate (PyBOP), and DIEA and coupled to activated Fmoc-protected D-hydroxyproline (Fmoc-D-Hyp-OH) to yield B. Deprotection of the terminal amino acid is carried out in the presence of a mild base, e.g., 20% 4-methylpiperidine, and 1-hydroxybenzotriazole (HOBt), benzotriazol-1-yl-oxy-tris(pyrrolidino)phosphonium hexafluorophosphate (PyBOP), and DIEA and coupled to activated Fmoc-protected phenylalanine (Fmoc-Phe-OH) to yield C. Deprotection of the terminal amino acid is carried out in the presence of a mild base, e.g., 20% 4-methylpiperidine, and 1-hydroxybenzotriazole (HOBt), benzotriazol-1-yl-oxy-tris(pyrrolidino)phosphonium hexafluorophosphate (PyBOP), and DIEA and coupled to activated Fmoc-protected tryptophan (Fmoc-Trp-OH) to yield D. At this step, D- or L-Trp can be incorporated depending on the desired stereochemistry of the final product. A final deprotection step is carried out in the presence of a mild base, e.g., 20% 4-methylpiperidine, and 1-hydroxybenzotriazole (HOBt), benzotriazol-1-yl-oxy-tris(pyrrolidino)phosphonium hexafluorophosphate (PyBOP), and DIEA to yield E with a free amino-terminus. At any step in the reaction, the D- or L-isomer of the amino acid can be added, depending on the desired stereochemistry of the final product. Cleavage of the linear peptide from the 2-chlorotrityl resin is achieved under acidic conditions in the presence of 1% trifluoroacetic acid (TFA) and solvent is removed to yield the free linear peptide F. The linear peptide F was lyophilized prior to cyclization. The linear peptide F was characterized by mass spectrometry and HPLC (5-50% acetonitrile/water+0.1% TFA over 45 min). HPLC retention time was 28.6 min (214 nm), M+1=612.3 m/z (expected=612.3 m/z). Cyclization of the linear peptide to yield the macrocyclic tetrapeptide G was carried out as follows. The linear peptide precursor (25 mM, 0.5 equiv) in DMF was added dropwise at a rate of 1 mL/h to a solution of 1.5 equivalents of 0.9 mM O-(7-azabenzotriazol-1-yl)-N,N,N',N'-tetramethyluronium hexafluorophosphate (HATU) and 8 equivalents of DIEA (8 equiv) in DMF. Following addition of the peptide, HATU (1.5 equiv) was added directly to the solution. Additional linear peptide (25 mM, 0.5 equiv) in DMF was added dropwise at a rate of 1 mL/h. The reaction was then allowed to stir for 12 h. The temperature was increased to 38° C. and allowed to stir for an additional 24 h. Solvents were evaporated and resulting residue was dissolved in toluene and evaporated three times. The residue was then dissolved in ethyl acetate and washed three times each with 1 N citric acid, saturated sodium bicarbonate, and brine. The organics were dried over magnesium sulfate and solvent evaporated. The resulting product was purified by normal phase flash chromatography (0-100% ethylacetate/hexane) and lyophilized. The macrocyclic tetrapeptide G (also referred to as JVA 4101) was characterized by mass spectrometry and HPLC (Method A: 15-55% acetonitrile/water+0.1% TFA over 40 min, 214 nm; Method B: 30-70% methanol/water+0.1% TFA over 40 min, 230 nm). HPLC retention time was 23.6 min (Method A) and 25.7 min (Method B); M+1=594.5 m/z (expected=594.3 m/z), M+Na=616.5 m/z (expected=616.3 m/z). Side chain protection did not appear to be necessary for cyclization, however Fmoc-protected amino acids with side chain protecting groups could also be substituted for any of the amino acids in the synthesis of G. Unprotected 4-hydroxy-cis-D-proline (Fmoc-cis-D-Hyp) can be coupled at either the second or the third position from the resin. Alternatively, 4-hydroxy-trans-D-proline (Fmoc-trans-D-Hyp) can be incorporated at the second or third position from the resin. The overall yield of the reaction is improved when coupling D-Hyp at the third position on the resin. Cyclization conditions have been optimized to minimize the formation of the cyclic dimer and maximize the yield of the macrocyclic tetrapeptide and previously published [Kulkarni, S. S., Ross, N. C., McLaughlin, J. P., and Aldrich, J. V. (2009) Synthesis of cyclic tetrapeptide CJ 15,208: a novel kappa opioid receptor antagonist Adv Exp Med Biol 611, 269-270; Ross, N. C., Kulkarni, S. S., McLaughlin, J. P., and Aldrich, J. V. (2010) Synthesis of CJ-15,208, a novel k-opioid receptor antagonist Tetrahedron Lett 51, 5020-5023; Aldrich, J. V., Senadheera, S. N., Ross, N. C., Ganno, M. L., Eans, S. O., and McLaughlin, J. P. (2013) The macrocyclic peptide CJ-15,208 is orally active and prevents reinstatement of extinguished cocaine-seeking behavior J Nat Prod 76, 433-438; Senadheera, S. N., Kulkarni, S. S., McLaughlin, J. P., and Aldrich, J. V. (2011) Improved synthesis of CJ-15,208 isomers and their pharmacological activity at opioid receptors In Peptides: Building Bridges. Proceedings of the 22nd American Peptide Symposium, Lebl, M., Ed. American Peptide Society: San Diego, Calif., pp 346-347]. The macrocyclic tetrapeptides can be further purified by normal phase flash column chromatography as previously described by published procedures [Senadheera, S. N., Kulkarni, S. S., McLaughlin, J. P., and Aldrich, J. V. (2011) Improved synthesis of CJ-15,208 isomers and their pharmacological activity at opioid receptors In Peptides: Building Bridges. Proceedings of the 22nd American Peptide Symposium, Lebl, M., Ed. American Peptide Society: San Diego, Calif., pp 346-347]. Routine preparation of 500-600 mg of analogs can be achieved with this methodology, and the synthesis and purification can be scaled up if necessary.

Scheme I

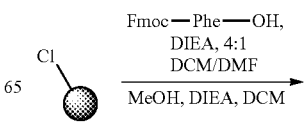

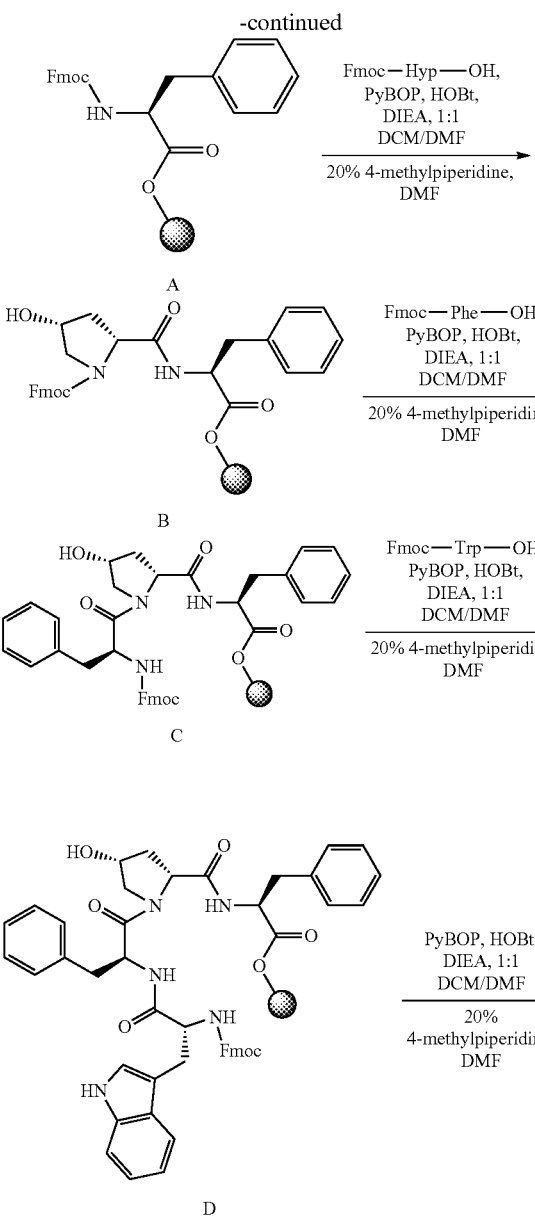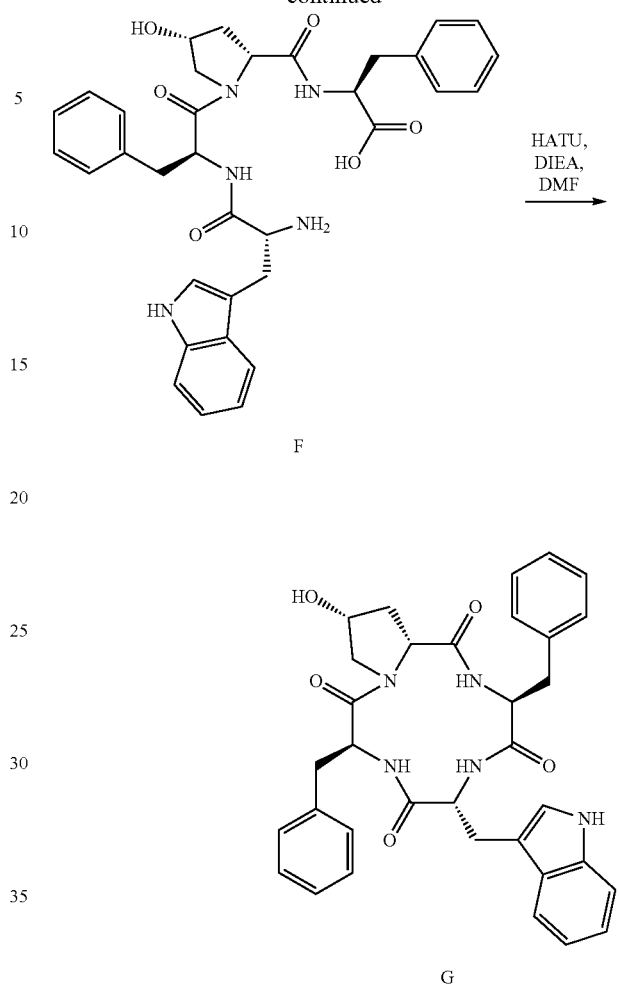
The macrocyclic tetrapeptide cyclo(Phe-cis-D-Hyp-Phe-D-Trp) (G) can be readily converted to the cyclo(Phe-trans-D-Hyp-Phe-D-Trp) isomer (H) as shown in Scheme II. A skilled artisan will recognize the potential for this Mitsunobu reaction to convert (G) to (H).
Scheme II
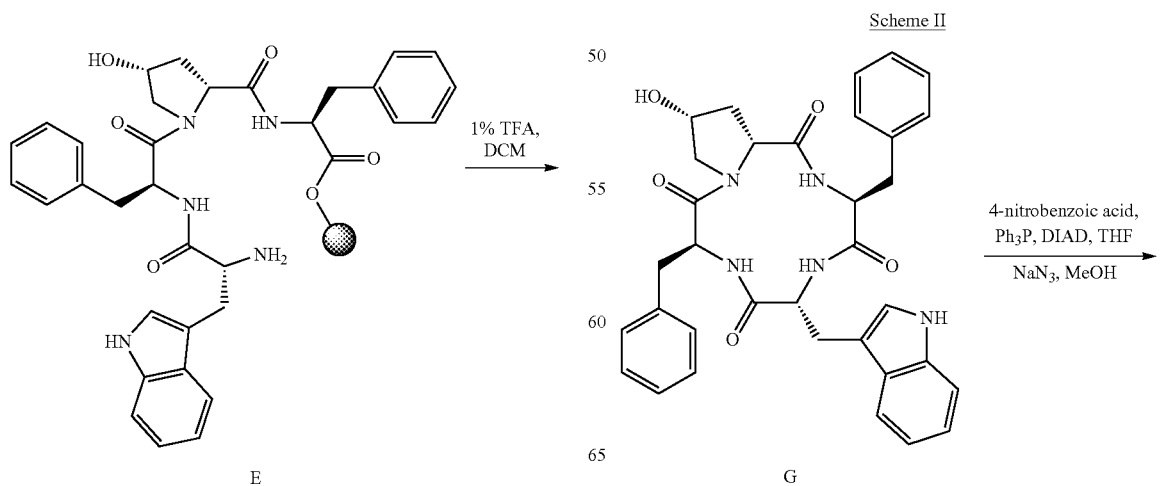

105
-continued

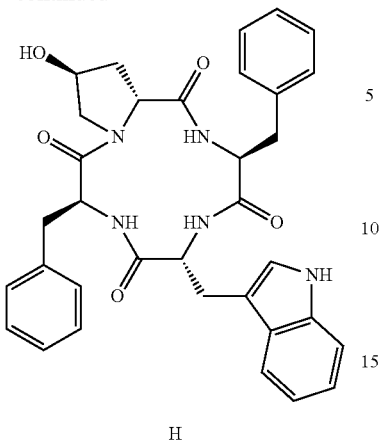

H

106
-continued

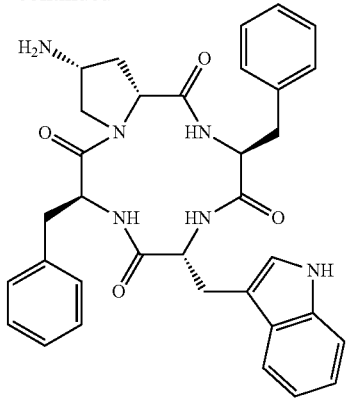

J

The macrocyclic tetrapeptide cyclo(Phe-cis-D-Hyp-Phe-D-Trp) (G) can be readily converted to the 4-aminoproline (Amp) derivative cyclo(Phe-cis-D-Amp-Phe-D-Trp) (J) as shown in Scheme III. A skilled artisan will recognize the potential for a Mitsunobu reaction to convert (G) to (I). A reductive amination reaction can then be carried out in the presence of triphenylphosphine or hydrogen and an appropriate catalyst, for example palladium, nickel, or the like. A skilled artisan will recognize the appropriate catalyst and reaction conditions for the conversion of (I) to (J).

The macrocyclic tetrapeptide cyclo(Phe-cis-D-Hyp-Phe-D-Trp) (G) can be readily converted to the trans isomer cyclo(Phe-trans-D-Amp-Phe-D-Trp) of the 4-aminoproline (Amp) derivative (L) as shown in Scheme IV. A skilled artisan will recognize the potential for a Mitsunobu reaction to convert (G) to (K). A reductive amination reaction can then be carried out in the presence of triphenylphosphine or hydrogen and an appropriate catalyst, for example palladium, nickel, or the like. A skilled artisan will recognize the appropriate catalyst and reaction conditions for the conversion of (K) to (L).

Scheme III

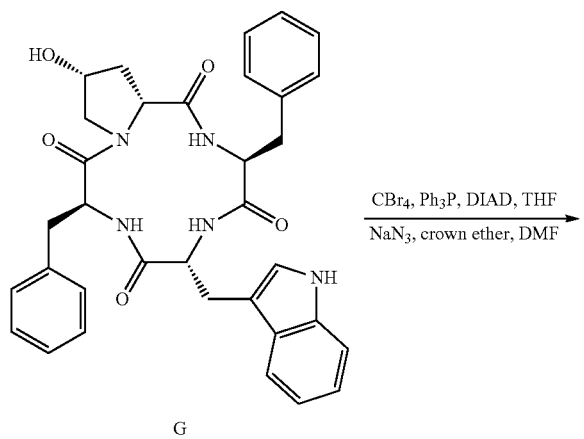

G

CBr₄, Ph₃P, DIAD, THF
—————————————→
NaN₃, crown ether, DMF

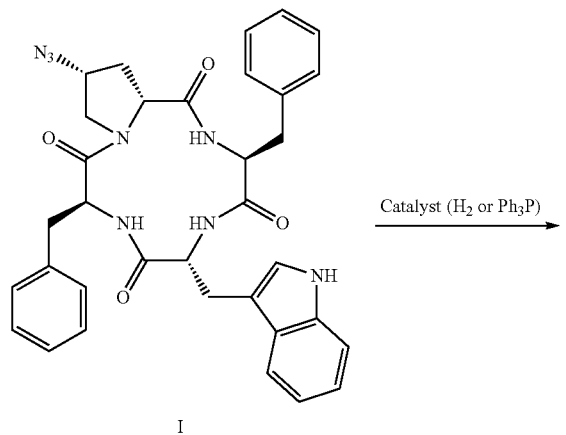

I

Catalyst (H₂ or Ph₃P)
—————————————→

Scheme IV

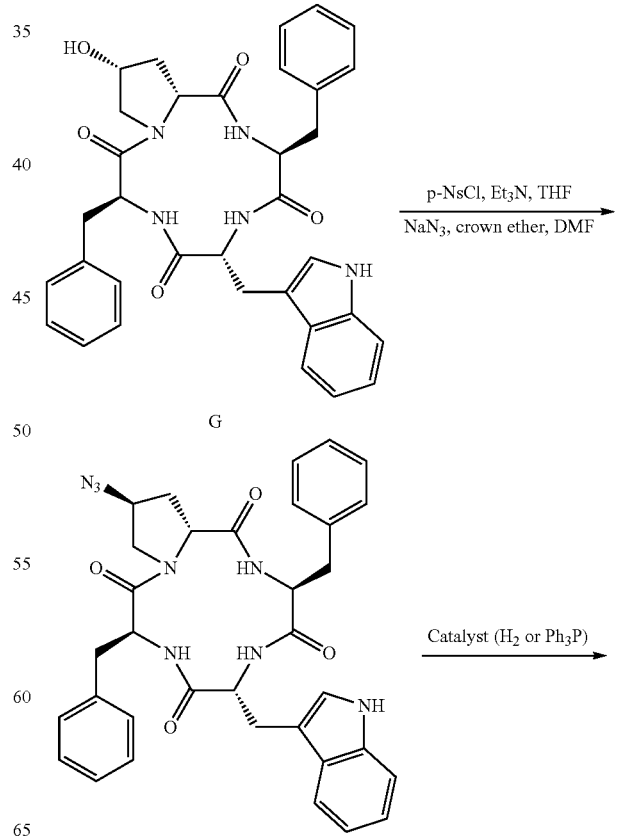

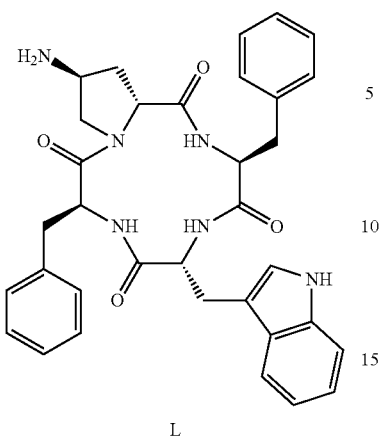

107

L

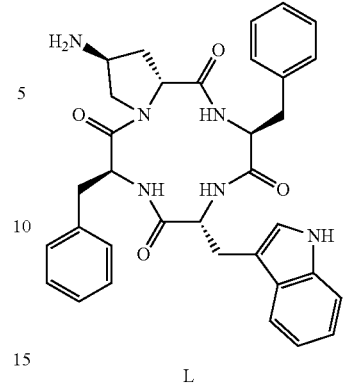

108

L

Derivatization of macrocyclic tetrapeptide cyclo(Phe-cis-D-Hyp-Phe-D-Trp) (G) or the corresponding 4-amino-D-hydroxyproline derivative to add linkers of varying lengths and compositions can be achieved through the general reaction Scheme V. The carboxylic acid moiety of the linker is coupled to the 4-hydroxy or 4-amino group on the proline of (G) or (L) to yield compound (M) or (O).

Scheme V

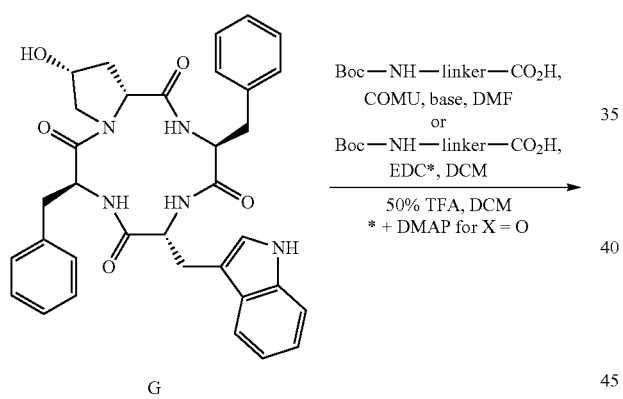

G

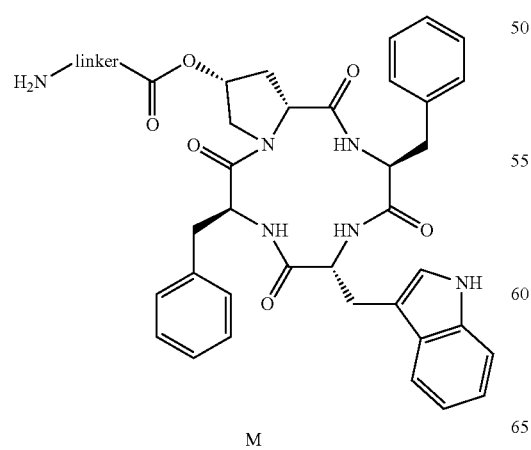

M

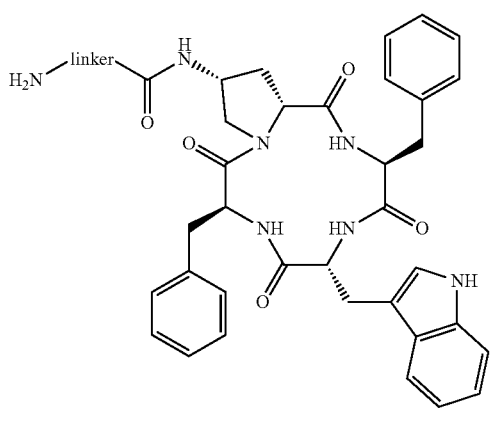

O

The following compounds can be prepared using a similar method as delineated in general reaction Scheme V:

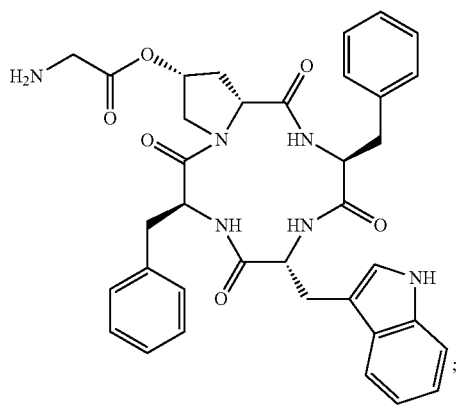

cyclo[Phe-cis-D-Hyp(Gly)²-Phe-D-Trp] (JVA 4102)

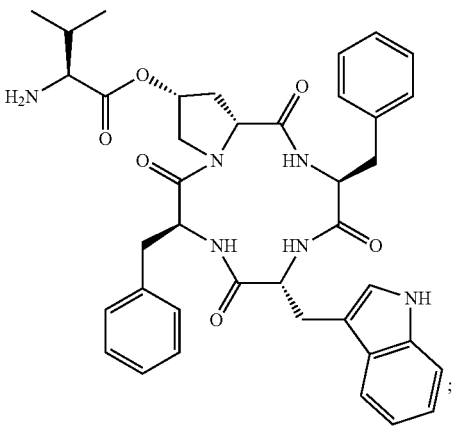

cyclo[Phe-cis-D-Hyp(Val)²-Phe-D-Trp]

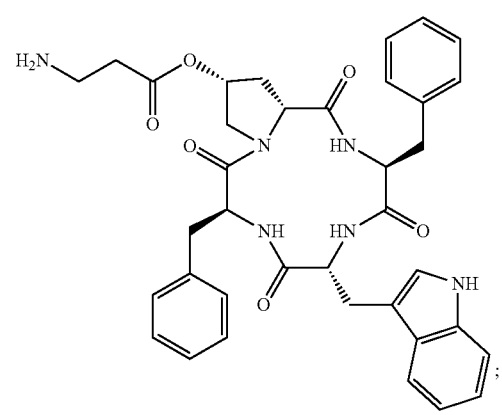

cyclo[Phe-cis-D-Hyp(β-Ala)²-Phe-D-Trp]

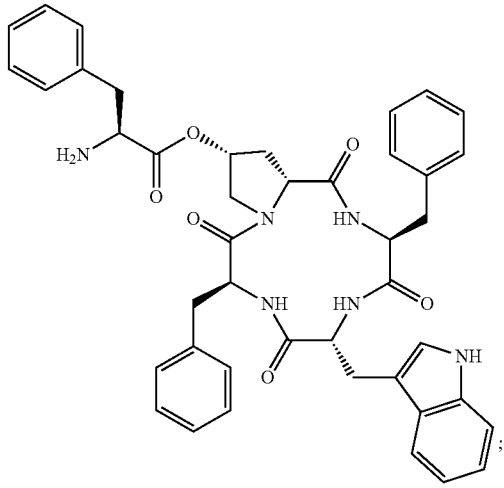

cyclo[Phe-cis-D-Hyp(Phe)²-Phe-D-Trp]

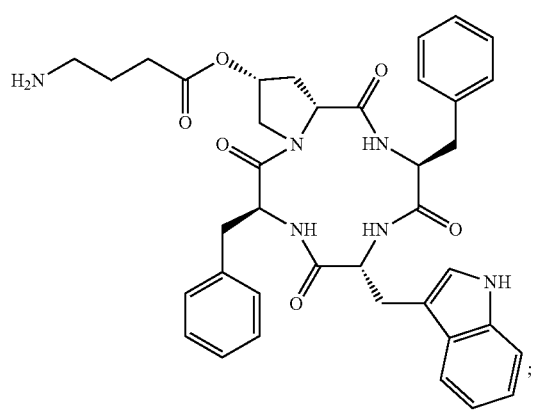

cyclo[Phe-cis-D-Hyp(γ-aminoisobutyric acid)²-Phe-D-Trp]

Any amino acid (denoted R for any amino acid side chain based on the amino acid) can be coupled to the macrocyclic tetrapeptide cyclo(Phe-cis-D-Hyp-Phe-D-Trp) (G) or the corresponding 4-amino-D-hydroxyproline derivative (L) using the general reaction scheme shown in Scheme VI. The amino acid may be protected or deprotected. The amino acid may be coupled directly to the 4-hydroxyl (M) or 4-amino group (O) of D-proline or to any linker of any length or composition, for example (M). The amino acid is coupled to a linker to form (N) and (P).

Scheme VI
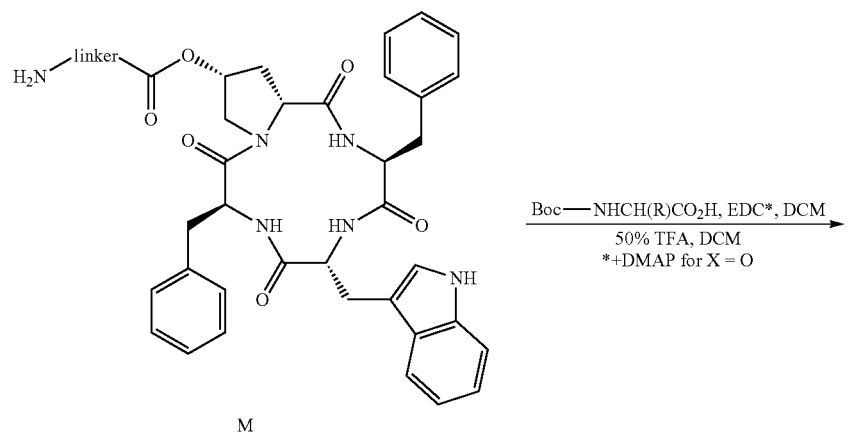
M
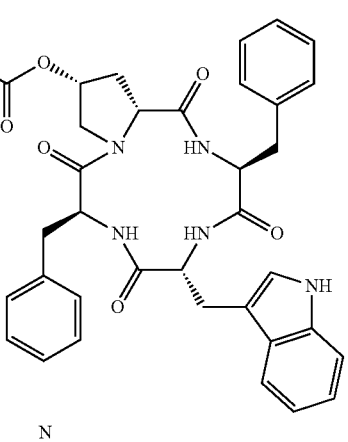
N
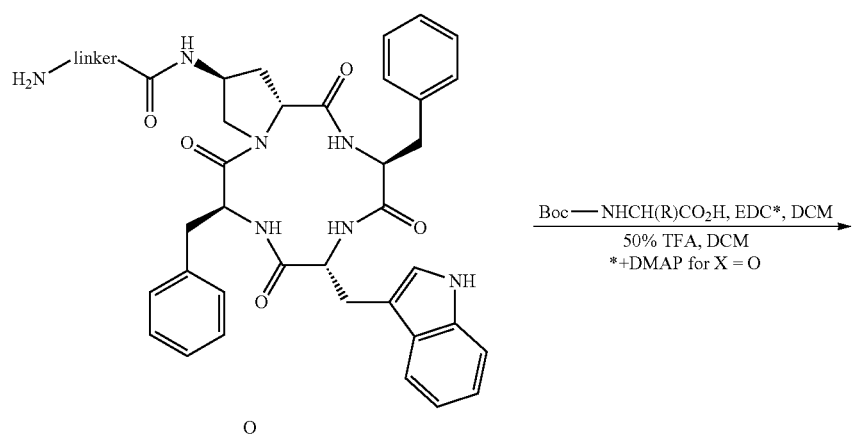
O

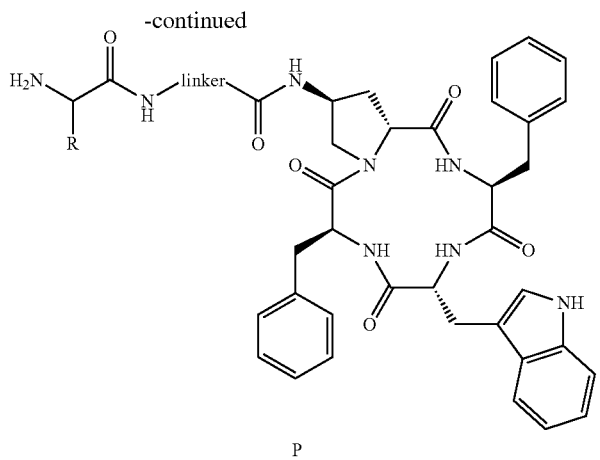

P

The compounds of the formulae herein can be tested for opioid receptor activity using any methodology known in the art, including but not limited to the in vitro and in vivo assays illustrated by the Examples below.

III. Uses of the Compounds of the Invention

The compounds of the invention can interact with opioid receptors. The lead compound cyclo(Phe-D-Pro-Phe-Trp) and its D-Trp derivative show selective activity against the kappa opioid receptor (KOR) over mu opioid receptors (MOR) and delta opioid receptors (DOR). Both of these macrocyclic peptides antagonize KOR in vitro. Unexpectedly, while the D-Trp isomer of cyclo(Phe-D-Pro-Phe-Trp) exhibited KOR antagonism, the L-Trp isomer of cyclo(Phe-D-Pro-Phe-Trp) was found to have mild agonist (antinociceptive) activity in vivo [Ross, N. C., Reilley, K. J., Murray, T. F., Aldrich, J. V., and McLaughlin, J. P. (2012) Novel opioid cyclic tetrapeptides: Trp isomers of CJ-15,208 exhibit distinct opioid receptor agonism and short-acting kappa opioid receptor antagonism Br J Pharmacol 165, 1097-1108]. However, these macrocyclic tetrapeptides have low solubility. Thus, the compounds of the invention improve solubility and enhance pharmacokinetic properties without sacrificing the pharmacological activity profile.

Thus, in one embodiment, the invention provides a compound that is an opioid receptor agonist, an opioid receptor antagonist, or a mixed opioid receptor agonist/antagonist. In certain embodiments, the invention provides a compound that is an opioid receptor agonist. In certain embodiments, the invention provides a compound that is an opioid receptor antagonist. In certain embodiments, the invention provides a compound that is a mixed opioid receptor agonist/antagonist.

In certain embodiments, the compound of the invention binds to more than one type of opioid receptor. In certain embodiments, the compound of the invention binds to one or more than one type of opioid receptor and can act as both an agonist and antagonist. For example, a compound is a kappa opioid receptor, mu opioid receptor, or delta opioid receptor agonist and a kappa opioid receptor, mu opioid receptor, or a delta opioid receptor antagonist, or any combination thereof. In certain embodiments, the compound is an opioid receptor agonist and an opioid receptor antagonist. In certain embodiments, the compound is a kappa opioid receptor agonist and a kappa opioid receptor antagonist. In certain embodiments, the compound is a mu opioid receptor agonist and a mu opioid receptor antagonist. In certain embodiments, the compound is a delta opioid receptor agonist and a delta opioid receptor antagonist. In certain embodiments, the compound is a kappa opioid receptor agonist and a mu opioid receptor antagonist. In certain embodiments, the compound is a kappa opioid receptor agonist and a delta opioid receptor antagonist. In certain embodiments, the compound is a mu opioid receptor agonist and a kappa opioid receptor antagonist. In certain embodiments, the compound is a mu opioid receptor agonist and a delta opioid receptor antagonist. In certain embodiments, the compound is a delta opioid receptor agonist and a kappa opioid receptor antagonist. In certain embodiments, the compound is a delta opioid receptor agonist and a mu opioid receptor antagonist.

A further aspect presents a method of treating a subject with a neurological disease, including administering to the subject a therapeutically effective amount of a compound of the invention (e.g., a compound of any formula herein or otherwise described herein). An addiction includes drug (e.g., cocaine) and alcohol addiction. In certain embodiments, the subject is a mammal, e.g. a human. In certain embodiments, the invention provides method of treating a subject with a neurological disease, including administering to the subject a therapeutically effective amount of a compound of the invention (e.g., a compound of any formula herein or otherwise described herein). In certain embodiments, the invention provides method of treating a subject with a neurological disease, including administering to the subject a therapeutically effective amount of a compound of the invention (e.g., a compound of any formula herein or otherwise described herein), wherein the neurological disease is addiction.

A further aspect presents a method of treating a subject with an addiction, including administering to the subject a therapeutically effective amount of a compound of the invention (e.g., a compound of any formula herein or otherwise described herein). An addiction includes drug (e.g., cocaine) and alcohol addiction. In certain embodiments, the subject is a mammal, e.g. a human. In certain embodiments, the invention provides a method of treating a subject with an addiction, including administering to the subject a therapeutically effective amount of a compound of the invention (e.g., a compound of any formula herein or otherwise described herein). In certain embodiments, the invention provides a method of treating a subject with an addiction, including administering to the subject a therapeutically effective amount of a compound of the invention (e.g., a compound of any formula herein or otherwise described herein), wherein the addiction is a drug addiction. In certain embodiments, the invention provides a method of treating a subject with an addiction, including administering to the subject a therapeutically effective amount of a compound of the invention (e.g., a compound of any formula herein or otherwise described herein), wherein the addiction is a cocaine addiction. In certain embodiments, the invention provides a method of treating a subject with an addiction, including administering to the subject a therapeutically effective amount of a compound of the invention (e.g., a compound of any formula herein or otherwise described herein), wherein the addiction is an alcohol addiction.

A further aspect presents a method of treating a subject with a psychiatric disorder, including administering to the subject a therapeutically effective amount of a compound of the invention (e.g., a compound of any formula herein or otherwise described herein). A psychiatric disorder includes, for example, anxiety disorders, mood disorders, personality disorders, psychotic disorders, and substance-related disorders, among others. In certain embodiments, the invention provides a method of treating a subject with a psychiatric disorder, including administering to the subject a therapeutically effective amount of a compound of the invention (e.g., a compound of any formula herein or otherwise described herein). In certain embodiments, the invention provides a method of treating a subject with a psychiatric disorder, including administering to the subject a therapeutically effective amount of a compound of the invention (e.g., a compound of any formula herein or otherwise described herein), wherein the psychiatric disorder is an anxiety disorder. In certain embodiments, the invention provides a method of treating a subject with a psychiatric disorder, including administering to the subject a therapeutically effective amount of a compound of the invention (e.g., a compound of any formula herein or otherwise described herein), wherein the psychiatric disorder is a substance-related disorder. In certain embodiments, the invention provides a method of treating a subject with a psychiatric disorder, including administering to the subject a therapeutically effective amount of a compound of the invention (e.g., a compound of any formula herein or otherwise described herein), wherein the psychiatric disorder is a substance-related disorder, wherein the substance-related disorder is a cocaine dependence. In certain embodiments, the invention provides a method of treating a subject with a psychiatric disorder, including administering to the subject a therapeutically effective amount of a compound of the invention (e.g., a compound of any formula herein or otherwise described herein), wherein the psychiatric disorder is a substance-related disorder, wherein the substance-related disorder is an opioid dependence. In certain embodiments, the invention provides a method of treating a subject with a psychiatric disorder, including administering to the subject a therapeutically effective amount of a compound of the invention (e.g., a compound of any formula herein or otherwise described herein), wherein the psychiatric disorder is a mood disorder.

A further aspect presents a method of treating a subject with a painful condition, including administering to the subject a therapeutically effective amount of a compound of the invention (e.g., a compound of any formula herein or otherwise described herein). In certain embodiments, the invention provides a method of treating a subject with a painful condition, including administering to the subject a therapeutically effective amount of a compound of the invention (e.g., a compound of any formula herein or otherwise described herein). In certain embodiments, the invention provides a method of treating a subject with a painful condition, including administering to the subject a therapeutically effective amount of a compound of the invention (e.g., a compound of any formula herein or otherwise described herein), wherein the painful condition is nociceptive pain. In certain embodiments, the invention provides a method of treating a subject with a painful condition, including administering to the subject a therapeutically effective amount of a compound of the invention (e.g., a compound of any formula herein or otherwise described herein), wherein the painful condition is pain associated with withdrawal symptoms from drug addiction.

A further aspect presents a method of treating a subject with a condition, including administering to the subject a therapeutically effective amount of a compound of the invention (e.g., a compound of any formula herein or otherwise described herein). In certain embodiments, the invention provides a method of treating a subject with a condition, including administering to the subject a therapeutically effective amount of a compound of the invention (e.g., a compound of any formula herein or otherwise described herein). In certain embodiments, the invention provides a method of treating a subject with a condition, including administering to the subject a therapeutically effective amount of a compound of the invention (e.g., a compound of any formula herein or otherwise described herein), wherein the condition is nociceptive pain. In certain embodiments, the invention provides a method of treating a subject with a condition, including administering to the subject a therapeutically effective amount of a compound of the invention (e.g., a compound of any formula herein or otherwise described herein), wherein the condition is associated with withdrawal symptoms from drug addiction.

A further aspect presents a method of administering a therapeutically effective amount of a compound of the invention to a subject in need of an analgesic. A subject in need of analgesic further encompasses any disease or disorder that results in pain in the subject.

A further aspect presents a method of treating a subject suffering from an opioid receptor mediated disorder, including administering to the subject a therapeutically effective amount of a compound of the invention (e.g., a compound of any formula herein or otherwise described herein). An opioid receptor mediated disorder includes stress-induced reinstatement of drug-seeking behavior, stress-induced reinstatement of cocaine-seeking behavior, drug-induced reinstatement of drug-seeking behavior, and cocaine-induced reinstatement of cocaine-seeking behavior. In certain embodiments, the invention provides a method of treating a subject with an opioid receptor mediated disorder, including administering to the subject a therapeutically effective amount of a compound of the invention (e.g., a compound of any formula herein or otherwise described herein). In certain embodiments, the subject is a mammal, e.g. a human. In certain embodiments, the invention provides a method of treating a subject with an opioid receptor mediated disorder, including administering to the subject a therapeutically effective amount of a compound of the invention (e.g., a compound of any formula herein or otherwise described herein), wherein the opioid mediated receptor disorder is stress-induced reinstatement of drug-seeking behavior. In certain embodiments, the invention provides a method of treating a subject with an opioid receptor mediated disorder, including administering to the subject a therapeutically effective amount of a compound of the invention (e.g., a compound of any formula herein or otherwise described herein), wherein the opioid mediated receptor disorder is drug-induced reinstatement of drug-seeking behavior. In certain embodiments, the invention provides a method of treating a subject with an opioid receptor mediated disorder, including administering to the subject a therapeutically effective amount of a compound of the invention (e.g., a compound of any formula herein or otherwise described herein), wherein the opioid mediated receptor disorder is stress-induced reinstatement of drug-seeking behavior, wherein the stress-induced reinstatement of drug-seeking behavior is stress-induced reinstatement of cocaine-seeking behavior. In certain embodiments, the invention provides a method of treating a subject with an opioid receptor mediated disorder, including administering to the subject a therapeutically effective amount of a compound of the invention (e.g., a compound of any formula herein or otherwise described herein), wherein the opioid mediated receptor disorder is drug-induced reinstatement of drug-seeking behavior, wherein the drug-induced reinstatement of drug-seeking behavior is cocaine-induced reinstatement of cocaine-seeking behavior.

A further aspect presents a method of treating a subject for cancer, including administering to the subject an effective amount of a compound of the invention (e.g., a compound of any formula herein or otherwise described herein) to thereby treat the subject suffering from cancer. In certain embodiments, the cancer harbors a c-Myc mutation. In certain embodiments, the c-Myc mutation results in the overexpression of c-Myc.

In certain embodiments, the methods of the invention include administering to a subject a therapeutically effective amount of a compound of the invention in combination with another pharmaceutically active compound. Examples of pharmaceutically active compounds include compounds known to treat opioid receptor mediated disorders, e.g., morphine, hydrocodone, oxycodone, fentanyl, hydromorphone, meperidine, methadone, naloxone, naltrexone, acetaminophen, NSAIDs (e.g., ibuprofen), naproxen, codeine, loperamide, naloxegol, nalmefene, diprenorphine, nalorphine, nalorphine dinicotinate, levallorphan, samidorphan, nalodeine, alvimopan, methylnaltrexone, 6β-naltrexol, axelopran, benevopran, methylsamidorphan, naldemedine, buprenorphine, dezocine, butorphanol, levorphanol, nalbuphine, pentazocine, phenazocine, and other agents cited herein. Other pharmaceutically active compounds that may be used can be found in Harrison's Principles of Internal Medicine, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired.

Compounds determined to be effective for the prevention or treatment of opioid receptor mediated disorders in animals, e.g., dogs, chickens, primates, and rodents, may also be useful in treatment of opioid receptor mediated disorders in humans. Those skilled in the art of treating opioid receptor mediated disorders in humans will know, based upon the data obtained in animal studies, the dosage and route of administration of the compound to humans. In general, the dosage and route of administration in humans is expected to be similar to that in animals.

The identification of those patients who are in need of treatment for opioid receptor mediated disorders is well within the ability and knowledge of one skilled in the art. Certain methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a opioid receptor mediated disorder by methods well known in the art (e.g., antinociceptive testing and diuresis testing) and then administering a therapeutically effective amount of an inhibitor of cell proliferation (e.g., a compound of any formula herein or otherwise described herein) according to the invention to the subject. After an appropriate period of time after the administration of the compound (e.g., 1 day, 1 week, 2 weeks, one month, six months), the extent of the opioid receptor mediated disorder is determined again. The modulation (e.g., decrease or increase) of the activity of the opioid receptor of the opioid receptor mediated disorder indicates efficacy of the treatment. The extent of modulation of the activity of the opioid receptor of the opioid receptor mediated disorder may be determined periodically throughout treatment. For example, the extent of modulation of the activity of the opioid receptor of the opioid receptor mediated disorder may be checked every few hours, days or weeks to assess the further efficacy of the treatment. When the compound is an antagonist, a decrease of the activity of the opioid receptor of the opioid receptor mediated disorder indicates that the treatment is efficacious. When the compound is an agonist, an increase of the activity of the opioid receptor of the opioid receptor mediated disorder indicates that the treatment is efficacious. The method described may be used to screen or select patients that may benefit from treatment with an agonist or antagonist or mixed agonist/antagonist of an opioid receptor.

Yet another aspect presents a method to identify a compound that is an opioid receptor agonist by measuring the compound's ability to activate KOR, MOR, and/or DOR. The method may include any method for measuring opioid receptor activity known in the art, such as the ones identified in the Examples. Once potential agonists are identified, the compounds may be screened using in vivo assays, such as the 55° C. warm water tail withdrawal assay or any of ones identified below in the Examples. Compounds identified that affect KOR, MOR, and/or DOR activity could be activators of KOR, MOR, and/or DOR and could be useful therapeutic agents.

Yet another aspect presents a method to identify a compound that is an opioid receptor antagonist by measuring the compound's ability to inhibit or reduce the activity of KOR, MOR, and/or DOR or block the activation of KOR, MOR, and/or DOR. The method may include any method for measuring opioid receptor activity known in the art, such as the ones identified in the Examples. Once potential antagonists are identified, the compounds may be screened using in vivo assays, such as the 55° C. warm water tail withdrawal assay or any of ones identified below in the Examples.

Compounds identified that affect KOR, MOR, and/or DOR activity could be inhibitors of KOR, MOR, and/or DOR and could be useful therapeutic agents.

In another aspect, a compound of the invention is packaged in a therapeutically effective amount with a pharmaceutically acceptable carrier or diluent. The composition may be formulated for treating a subject suffering from or susceptible to an opioid receptor mediated disorder, and packaged with instructions to treat a subject suffering from or susceptible to an opioid receptor mediated disorder.

Yet another aspect presents a method to determine the intracellular localization of a compound of any formulae herein, a method comprising contacting a cell with a macrocyclic peptide conjugated to carboxyfluorescein and determining the intracellular localization of the macrocyclic peptide conjugated to carboxyfluorescein. For example, the dye carboxyfluourescein can be attached to a macrocyclic peptide using a linker of appropriate length and composition. A cell can be contacted with a carboxyfluorescein-labeled macrocyclic peptide derivative, and the intracellular localization of said macrocyclic peptide can be determined through methods known in the art [Holm., T., Johansson, H., Lundberg, P., Pooga, M., Lindgren, M., and Langel, O. (2006) Studying the uptake of cell-penetrating peptides Nature Protocols 1, 1001-1005].

Yet another aspect presents a method to determine the intracellular localization of a compound of any formulae herein, a method comprising contacting a cell with a macrocyclic peptide conjugated to carboxyfluorescein or other fluorescent moiety and determining the intracellular localization of the macrocyclic peptide conjugated to carboxyfluorescein. For example, the dye carboxyfluourescein can be attached to a macrocyclic peptide using a linker of appropriate length and composition. A cell can be contacted with a carboxyfluorescein-labeled macrocyclic peptide derivative, and the intracellular localization of said macrocyclic peptide can be determined through methods known in the art [Holm., T., Johansson, H., Lundberg, P., Pooga, M., Lindgren, M., and Langel, O. (2006) Studying the uptake of cell-penetrating peptides Nature Protocols 1, 1001-1005].

Yet another aspect presents a method to determine the molecular target of the compound of any formulae herein, a method comprising contacting a cell with a macrocyclic peptide conjugated to biotin and determining the target of the compound. The cell can be obtained from any source (e.g., mice, rat, human). In certain embodiments, the cell is a cancer cell. For example, pull down assays involving biotin are common methods known in the art [Schulze, W. X. and Mann, M. (2004) A novel proteomic screen for peptide protein interactions J Biol Chem 279, 10756-10764].

IV. Pharmaceutical Compositions

The invention also provides a pharmaceutical composition, comprising an effective amount of a compound of the invention (e.g., a compound that is an opioid receptor agonist, a compound that is an opioid receptor antagonist, a compound that is a mixed opioid receptor agonist/antagonist, or a compound of any formula herein or otherwise described herein) and a pharmaceutically acceptable carrier. In a further embodiment, the effective amount is effective to treat a neurological disorder, psychiatric disorder, painful condition, opioid receptor mediated disorder, or a proliferative disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

Pharmaceutical compositions of the invention suitable for parenteral administration comprise one or more compound of the invention(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized. The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles,"

In: Goodman and Gilman's The Pharmaceutical Basis of Therapeutics, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

EXAMPLES

The invention is further illustrated by the following examples which are intended to illustrate but not limit the scope of the invention.

The compounds of the invention can be evaluated for their opioid activity in vitro and in vivo through a variety of assays known in the field. The following examples provide exemplary protocols for evaluating the opioid activity of the compounds of the invention.

Example 1: Radioligand Binding Assay

Compounds of the invention can be evaluated for opioid receptor affinities at KOR, MOR, and DOR in radioligand binding assays using well established procedures [Arttamangkul, S., Ishmael, J. E., Murray, T. F., Grandy, D. K., DeLander, G. E., Kieffer, B. L., and Aldrich, J. V. (1997) Synthesis and opioid activity of conformationally constrained Dynorphin A analogues J Med Chem 40, 1211-1218]. Briefly, opioid binding studies can be conducted on membranes derived from CHO cells stably expressing cloned (e.g., from rat) KOR, MOR, and DOR. Multiple (e.g., 12) different concentrations ranging from 0.1 nM to 10 μM of the compound are incubated with isolated membrane protein for approximately 90 mins in 50 mM Tris (pH 7.4) at 22° C. using [$^3$H]-diprenorphine ($K_d$=0.45 nM), [$^3$H]-DAMGO ([D-Ala$^2$, NMePhe$^4$, glyol]enkephalin, $K_d$ 0.49 nM) and [$^3$H]-DPDPE (cyclo[D-Pen$^2$, D-Pen]enkephalin, $K_d$ 1.76 nM) as the radioligands for κ, μ and δ opioid receptors, respectively. A radioligand binding assay can also be performed to determine if there is a significant interaction between compounds of the invention and non-opioid receptors. Non-specific binding can be determined in the presence of 10 mM unlabelled dynorphin A-(1-13) amide (Dyn A-(1-13) amide), DAMGO and DPDPE for κ, μ and δ opioid receptors, respectively. Reactions are terminated by rapid filtration over Whatman GF/B fibre filters using a Brandel M24-R cell harvester and the filters counted in 4 mL of Cytocint (ICN Radiochemicals, Irvine, Calif., USA) using a Beckman LS6800 scintillation counter (Beckman Instruments, Fullerton, Calif., USA).

Generally, three to five independent experiments are conducted for the compound of the invention according to the protocol described above. $IC_{50}$ values can be determined by non-linear regression analysis to fit a logistic equation to the competition data using standard statistical software (e.g., GraphPad Prism, GraphPad Software, La Jolla, Calif., USA). The $K_1$ values of unlabeled compounds of the invention can be calculated from the Cheng and Prusoff equation $K_i=IC_{50}/(1+S)$, where S=(concentration of radioligand)/($K_d$ of radioligand) [Cheng, Y. C. and Prusoff, W. H. (1973) Relationship between the inhibition constant ($K_i$) and the concentration of inhibitor which causes 50 percent inhibition ($IC_{50}$) of an enzyme reaction Biochem Pharmacol 22, 3099-3108], using $K_d$ values of [$^3$H]-diprenorphine, [$^3$H]-DAMGO and [$^3$H]-DPDPE as listed above.

Example 2: GTPγ$^{35}$S Assay

Compounds of the invention can be evaluated for their efficacy and agonist/antagonist potency using a GTPγ$^{35}$S assay according to previously published methods [Ross, N. C., Reilley, K. J., Murray, T. F., Aldrich, J. V., and McLaughlin, J. P. (2011) Novel opioid cyclic tetrapeptides: Trp isomers of CJ-15,208 exhibit distinct opioid receptor agonism and short-acting kappa opioid receptor antagonism Br J Pharmacol 165, 1097-1108]. Briefly, the binding of the GTP analogue [$^{35}$S]-GTPγS to membranes is assayed following published methods [Siebanallar, J. F. and Murray, T. F. (1999) Hydrostatic pressure alters the time course of GTP (S) binding to G proteins in brain membranes from two congeneric marine fishes Biol Bull 197, 388-394]. The assay mixture contains 50 mM HEPES (pH 7.4), 1 mM EDTA, 5 mM magnesium acetate, 1 mM GDP, 1 mM dithiothreitol (DTT), 100 mM NaCl, 1 mg BSA mL$^{-1}$ and approximately 100,000 dpm [$^{35}$S]-GTPγS (0.1 to 0.2 nM). Approximately 10 μg of κ or μ opioid receptor-expressing CHO cell membrane protein are used per tube. Following a 90 min incubation at 22° C., the assay is terminated by filtration under vacuum on a Brandel (Gaithersburg, Md., USA) model M-48R cell harvester using Schleicher and Schuell Inc. (Keene, N.H., USA) number 32 glass fibre filters. The filters are rinsed with four 4 mL washes of ice-cold 50 mM Tris-HCl (pH 7.4) containing 5 mM MgCl at 5° C. to remove unbound [$^{35}$S]-GTPγS. Filter disks are then placed into counting vials to which 8 mL of Biocount scintillation fluid (Research Products International Corp., Mount Prospect, Ill., USA) is added. Filter-bound radioactivity is determined by liquid scintillation spectrometry (Beckman Instruments) following overnight extraction at room temperature. Specific binding is defined as total binding minus that occurring in the presence of 3 μM unlabelled GTPγS. Non-specific binding is approximately 1% of the total binding at 0.1 nM [$^{35}$S]-GTPγS. A GTPγ$^{35}$S assay can also be performed to characterize the function of compounds of the invention on non-opioid receptors.

Generally, three to five independent studies are conducted for the compound of the invention according to the method described above. The $K_B$ values for the inhibition of opioid agonist-induced stimulation of [$^{35}$S]-GTPγS binding by the compound of the invention can be calculated by Schild analysis using the equation: log (DR-1)=log [I]−log $K_B$, where [I] is the concentration of compound of the invention, $K_B$ is the equilibrium dissociation constant of the compound of the invention and DR is the dose-ratio shift produced by the compound of the invention [Arunlakshana, O. and Schild, H. O. (1959) Some quantitative uses of drug antagonists Br J Pharmacol Chemother 14, 48-58].

Example 3: High-Throughput FLIPR Membrane Potential Assay

Compounds of the invention can be assessed for their opioid agonism and antagonism potential in a high throughput format (FLIPR II) using the FLIPR Membrane Potential (FMP Blue) assay to measure opioid agonist-induced hyperpolarization according to previously published protocols [Whiteaker, K. L., Gopalakrishnan, S. M., Groebe, D., Shieh, C. C., Warrior, U., Burns, D. J., Coghlan, M. J., Scott, V. E., and Gopalakrishnan, M. (2001) Validation of FLIPR membrane potential dye for high throughput screening of potassium channel modulators J Biomol Screen 6, 305-312; George, J., Baden, D. G., Gerwick, W. H., and Murray, T. F. (2012) Bidirectional influence of sodium channel activation on NMDA receptor-dependent cerebrocortical neuron structural plasticity. Proc Natl Acad Sci USA 109, 19840-19845]. The assay has been optimized the FMP Blue assay to detect opioid receptor mediated hyperpolarization of CHO cells. This assay can quantify either positive or negative (inverse agonist) efficacy in an assay dependent on opioid receptor regulation of a $K^+$ conductance, and these data can be compared to the results of the GTPγ$^{35}$S assay.

Example 4: Release of Dyn a from Cortical Neurons

The release of Dyn A from cortical neurons or a model cell line induced by the compounds of the invention under both control and depolarizing (25 mM $K^+$) conditions can be determined, using procedures previously described [Josefsen, K., Buschard, K., Sorensen, L. R., Wollike, M., Ekman, R., and Birkenbach, M. (1998) Glucose stimulation of pancreatic beta-cell lines induces expression and secretion of dynorphin Endocrinology 39, 4329-4336; Yakovleva, T., Bazov, I., Cebers, G., Marinova, Z., Hara, Y., Ahmed, A., Vlaskovska, M., Johansson, B., Hochgeschwender, U., Singh, I. N., Bruce-Keller, A. J., Hurd, Y. L., Kaneko, T., Terenius, L., Ekstrom, T. J., Hauser, K. F., Pickel, V. M., and Bakalkin, G. (2006) Prodynorphin storage and processing in axon terminals and dendrites FASEB J 20, 2124-2126]. Dyn A can be quantified using a radio- or fluorescent enzyme-linked immunoassay (Phoenix Pharmaceuticals).

Example 5: Plasma Protein Binding

The compounds of the invention can be tested for plasma protein binding. Following incubation for 30 min at 4° C., samples will be filtered through 5000 molecular weight filters (Millipore) to separate free from protein-bound compound, and the concentration of free compound in the filtrate determined by LC-MS/MS.

Example 6: Efflux Protein Interaction and Caco-2 Monolayer Assay

The ability of the compounds of the invention to penetrate Caco-2 monolayers can be assessed according to standard procedures [Liederer, B. M., Fuchs, T., Vander Velde, D., Siahaan, T. J., and Borchardt, R. T. (2006) Effects of amino acid chirality and the chemical linker on the cell permeation characteristics of cyclic prodrugs of opioid peptides J Med Chem 49, 1261-1270]. The permeability of the compounds of the invention in the presence of efflux protein inhibitors (the P-glycoprotein inhibitor GF120918 and the MRP inhibitor MK 571, Tocris) can be assessed to determine the involvement of these transporters. The ability of the compounds of the invention to inhibit intracellular accumulation of the fluorescent P-glycoprotein (MDR1) substrate rhodamine can be determined as previously published [Zhu, H. J., Wang, J. S., Markowitz, J. S., Donovan, J. L., Gibson, B. B., and DeVane, C. L. (2007) Risperidone and paliperidone inhibit p-glycoprotein activity in vitro Neuropsychopharmacology 32, 757-764]. Additionally, the accumulation studies can be done with a different fluorescent substrate (e.g. the multi-transporter substrate 2',7'-bis(2-carboxyethyl)-5(6)-carboxyfluorescein acetoxy ester (BCECF-AM) and its metabolite the free acid) if inhibitor studies suggest another efflux protein is involved (e.g. MRP2) [Collington, G. K., Hunter, J., Allen, C. N., Simmons, N. L., and Hirst, B. H. (1992) Polarized efflux of 2',7'-bis(2-carboxyethyl)-5(6)-carboxyfluorescein from cultured epithelial cell monolayers Biochem Pharmacol 44, 417-424; Bachmeier, C. J., Trickler, W. J., and Miller, D. W. (2004) Drug efflux transport properties of 2',7'-bis(2-carboxyethyl)-5(6)-carboxyfluorescein acetoxymethyl ester (BCECF-AM) and its fluorescent free acid, BCECF J Pharm Sci 93, 932-942].

Example 7: In Vitro Metabolism and Stability Studies

The in vitro stability of the compounds of the invention in mouse hepatic microsomes can be examined. Following incubation with the compound for various times at 37° C., the proteins are precipitated with MeCN, and the samples are centrifuged and analyzed by LC-MS/MS. The apparent $t_{1/2}$ can be calculated for disappearance of the compound from the microsomes. In cases where appreciable metabolism appears to be occurring, metabolites can be characterized by LC-MS. The stability of selected compounds of the invention can also be analyzed in mouse brain homogenate using similar procedures.

Example 8: In Vivo Pharmacokinetic Analysis Using LC-MS/MS

The compounds of the invention can be administered to rats and mice in different dosages. Blood samples (0.25 mL)

obtained from rats or mice at various time points and the amount of compound in the plasma can be determined by LC-MS/MS. These studies provide basic PK parameters (AUC, Cmax, $t_{1/2}$) and the PK data can be analyzed using WinNonlin software. The blood samples can also be monitored for the presence of any metabolites identified in the in vitro analysis in hepatic microsomes described above. The PK parameters of selected compounds of the invention can also be obtained using LC-MS/MS following subcutaneous administration to assess oral bioavailability.

Example 9: Intracerebroventricular (i.c.v.) Administration Technique

The intracerebroventricular (i.c.v.) injections of the compounds of the invention are made directly into the lateral ventricle (e.g. of a mouse) according to the modified method as published [Haley, T. J. and McCormick, W. G. (1957) Pharmacological effects produced by intracerebral injections of drugs in the conscious mouse Br J Pharmacol Chemother 12, 12-15]. Briefly, the volume of injections is 5 µL. The mouse is lightly anaesthetized with isoflurane, an incision made in the scalp, and the injection made 2 mm lateral and 2 mm caudal to bregma at a depth of 3 mm using a 10 µL Hamilton syringe.

Example 10: 55° C. Warm-Water Tail-Withdrawal Assay

Antioceptive testing in the presence of compounds of the invention can be conducted in vivo using a 55° C. warm-water tail-withdrawal assay as published [McLaughlin, J. P., Hill, K. P. Jiang, Q., Sebastian, A., Archer, S., and Bidlack, J. M. (1999) Nitrocinnamoyl and chlorocinnamoyl derivatives of dihydrocodeinone: in vitro and in vivo characterization of mu-selective agonist and antagonist activity J Pharmacol Exp Ther 289, 304-311]. Generally, the mice used for this assay are C57Bl/6 mice. Briefly, warm (55° C.) water in a 2 L heated water bath is used as the thermal nociceptive stimulus, with the latency of the mouse to withdraw its tail from the water taken as the endpoint. After determination of baseline tail-withdrawal latencies, mice are administered a graded dose of a compound of the invention i.c.v.; where the compounds of the invention are administered in 50% dimethyl sulphoxide (DMSO) in sterile saline (0.9%). To determine agonist activity, the tail-withdrawal latency is determined repeatedly every 10 min following administration of a compound of the invention for 1 h or until latency returns to baseline values. To determine antagonist activity, mice are pretreated with the compound of the invention 80 min before administration of the opioid receptor-preferring agonist morphine (10 mg-kg$^{-1}$, i.p.), K opioid receptor-selective agonist U50,488 (10 mg-kg$^{-1}$, i.p.) or δ opioid receptor-selective agonist SNC-80 (100 nmol, i.c.v.). Antinociception produced by these established agonists is then measured 40 min after their administration. To determine the duration of κ opioid receptor antagonist activity, additional mice can be pretreated for 7.3, 17.3, 23.3 or 47.3 h before the administration of U50,488 as described previously.

To determine the opioid receptor selectivity of the agonist activity of the compound of the invention, mice can be pretreated with a single dose of (β-FNA (5 mg-kg$^{-1}$, s.c.) or nor-BNI (10 mg-kg$^{-1}$, i.p.) 23.3 h in advance of administration of the compound of the invention (10 nmol, i.c.v). Additional mice are pretreated 30 min prior to the administration of the compound of the invention with the opioid receptor non-selective antagonist naloxone (10 mg-kg$^{-1}$, s.c.), opioid receptor-selective antagonist CTAP (1 nmol, i.c.v.), κ opioid receptor-selective antagonist zyklophin (3 mg-kg$^{-1}$, s.c.) or δ opioid receptor-selective antagonist naltrindole (20 mg-kg$^{-1}$, i.p.), with antinociceptive testing 40 min later. Reference agonists and antagonists are administered using sterile saline (0.9%) as the vehicle, except for SNC-80 which is dissolved in 35% DMSO in sterile saline (0.9%). A cut-off time of 15 s can be used in this study; if the mouse fails to display a tail-withdrawal response during that time, the tail is removed from the water and the animal is assigned a maximal antinociceptive score of 100%.

To determine the opioid receptor selectivity of the agonist activity of the compound of the invention, mu opioid receptor knock-out mice and kappa opioid receptor knock-out mice are treated with the compound, with antinociceptive testing 40 min later. Additional mice are pretreated 30 min prior to the administration of the compound of the invention with the opioid receptor non-selective antagonist naloxone (10 mg-kg$^{-1}$, s.c.) or the δ opioid receptor-selective antagonist naltrindole (20 mg-kg$^{-1}$, i.p.), with antinociceptive testing 40 min later. Reference agonists and antagonists are administered using sterile saline (0.9%) as the vehicle, except for SNC-80 which is dissolved in 35% DMSO in sterile saline (0.9%). A cut-off time of 15 s can be used in this study; if the mouse fails to display a tail-withdrawal response during that time, the tail is removed from the water and the animal is assigned a maximal antinociceptive score of 100%.

At each time point, antinociception can be calculated according to the following formula:

% antinociception=100×(test latency−control latency)/(15−control latency)

Figure 3:
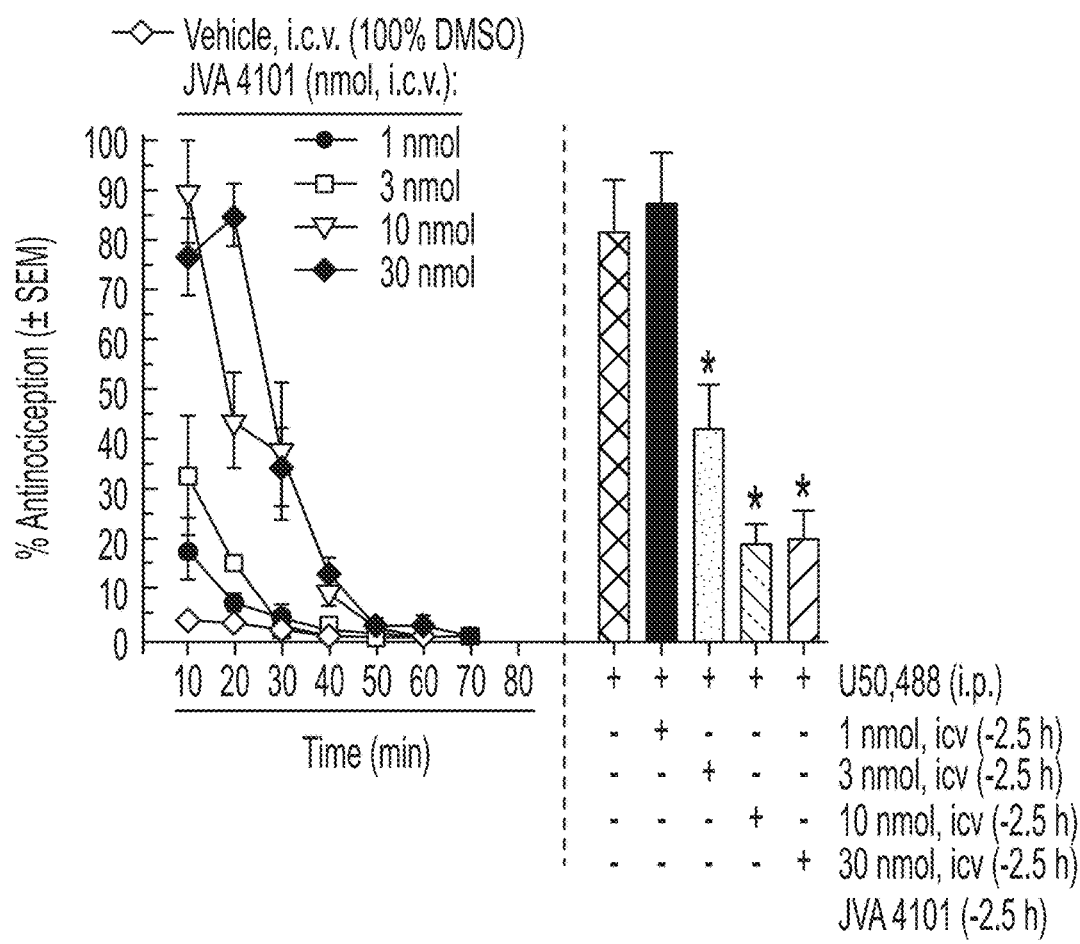
FIG. 3. shows in vivo agonist and antagonist activity. To evaluate the in vivo activity of the hydroxyproline derivative, mice received peptide by intracerebroventricular administration. Antinociception was measured over a time course of 70 minutes in the 55° C. warm water tail withdrawal test. To measure KOR antagonist activity, the mice were treated with peptide about 2.5 hours prior to receiving the KOR specific agonist, U50,488. The ED50 at 20 minutes was approximately 9 nmol after i.c.v. administration. Antagonist activity was observed at a dose of 3 nmol, with maximal antagonist activity achieved by 10 nmol.
Figure 5:
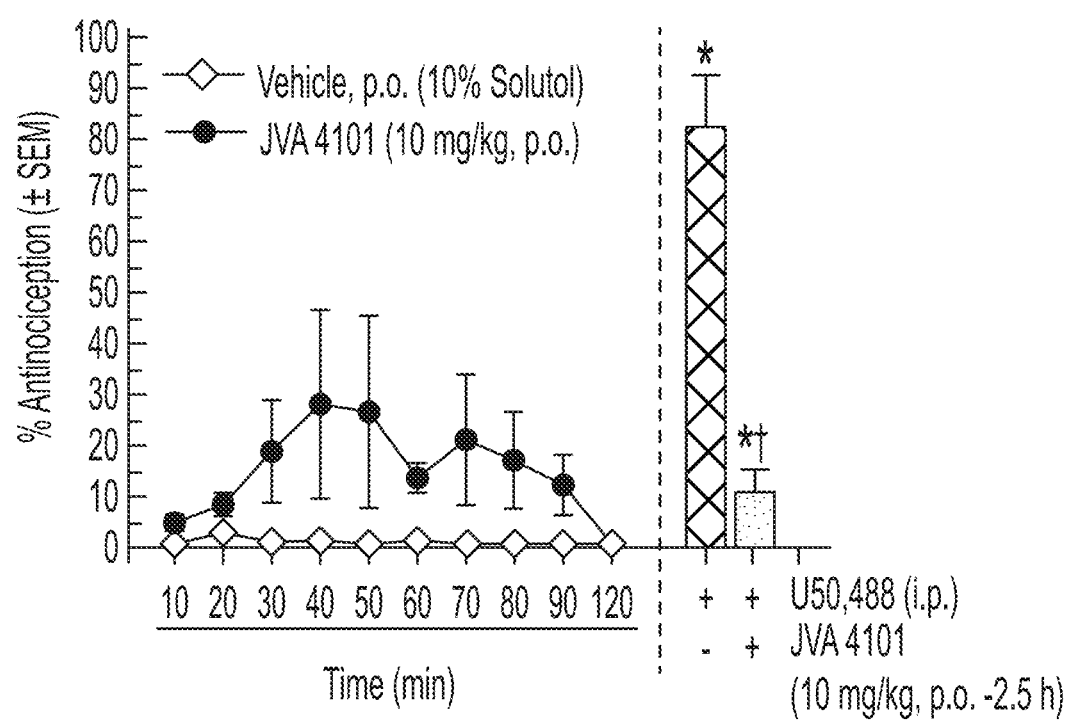
FIG. 5. shows oral agonist and antagonist activity. The hydroxyproline derivative was orally administered to mice at a dose of 10 mg/kg. Antinociception was measured in the 55° C. warm water tail withdrawal test over a time course of 120 minutes. KOR antagonist activity was measured after treatment with peptide for 2.5 hours followed by U50,488 administration. The hydroxyproline derivative demonstrated some agonist activity after oral administration. KOR antagonist activity was observed after oral administration, indicating blood brain barrier permeability.
Figure 6:
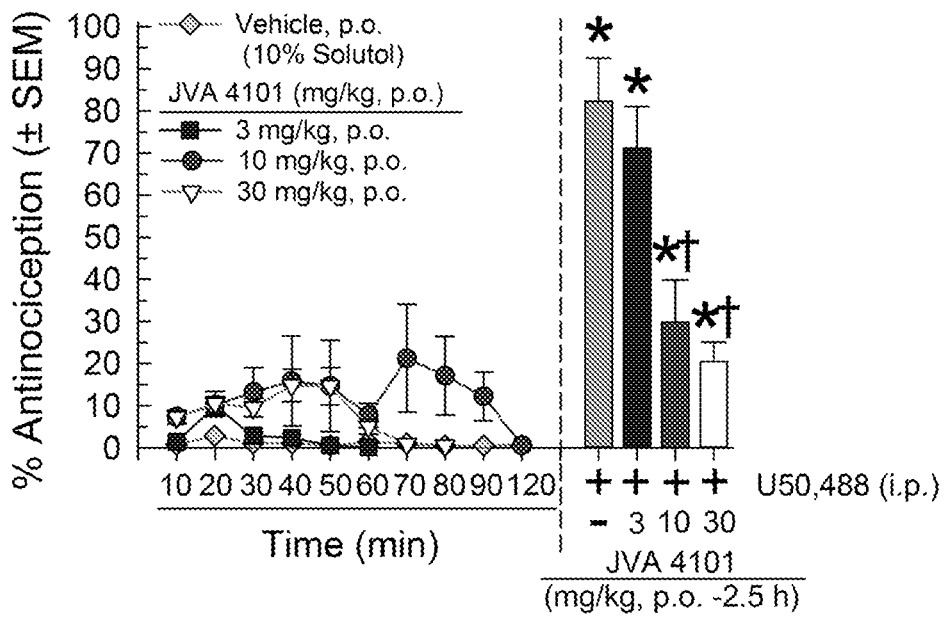
FIG. 6. shows the evaluation of cyclo[Phe-cis-D-Hyp-Phe-D-Trp] (Compound G, JVA 4101) in the mouse 55° C. warm water tail withdrawal assay following oral administration. cyclo[Phe-cis-D-Hyp-Phe-D-Trp] (Compound G, JVA 4101) exhibited significant antagonism at doses of 10 and 30 mg/kg p.o. of the KOR agonist U50,488 administered intraperitoneal (i.p.). Significantly different from * vehicle treated control and t U50,488 alone, p<0.5.
Figure 7:
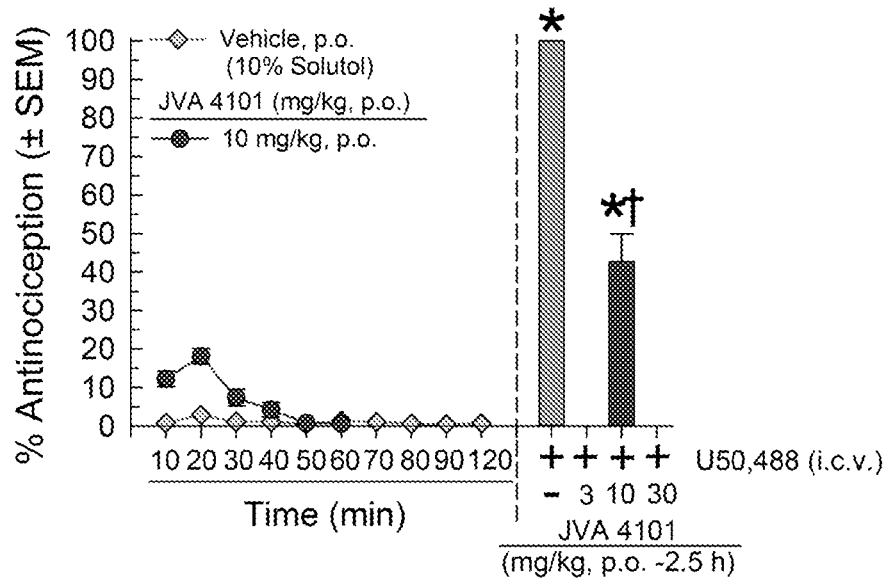
FIG. 7. shows the evaluation of cyclo[Phe-cis-D-Hyp-Phe-D-Trp] (Compound G, JVA 4101) in the mouse 55° C. warm water tail withdrawal assay following oral administration. cyclo[Phe-cis-D-Hyp-Phe-D-Trp] (Compound G, JVA 4101) (10 mg/kg p.o.) significantly antagonized U50,488 administered centrally (i.c.v.). Significantly different from * vehicle treated control and † U50,488 alone, p<0.5.
Figure 8:
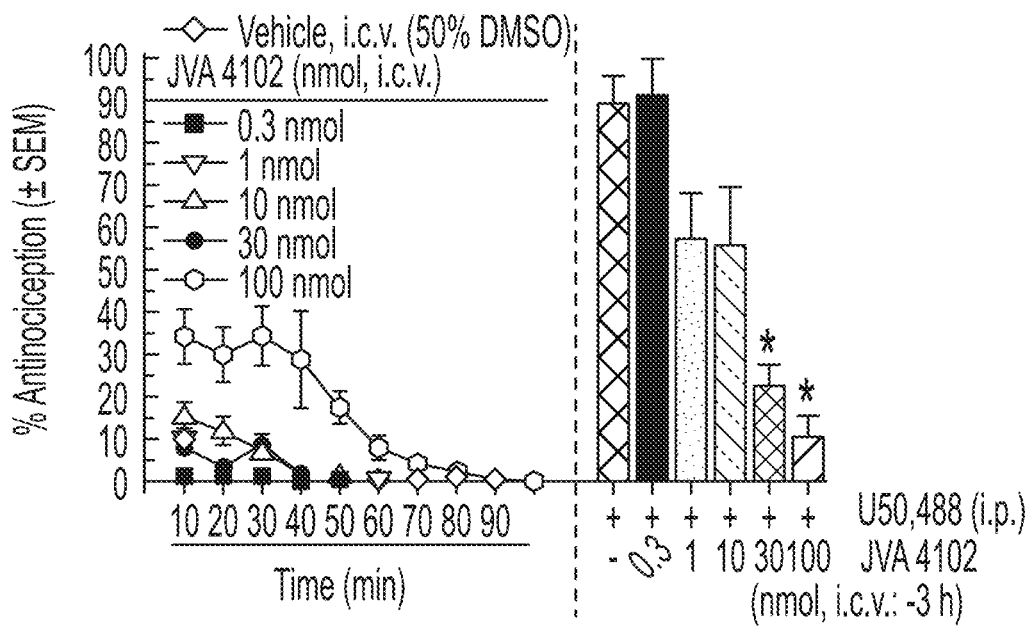
FIG. 8. shows the evaluation of cyclo[Phe-cis-D-Hyp(Gly)$^2$-Phe-D-Trp] (JVA 4102) in the mouse 55° C. warm water tail withdrawal assay. cyclo[Phe-cis-D-Hyp(Gly)$^2$-Phe-D-Trp] (JVA 4102) exhibited significant antagonism of U50,488 administered i.p. at doses of 30 and 100 nmol i.c.v. * Significantly different from U50,488 alone, p<0.5. B. JVA-4102 also exhibits significant KOR antagonism after subcutaneous administration (30 mg/kg). Significantly different from * vehicle treated control and † U50,488 alone, p<0.5.
Figure 9:
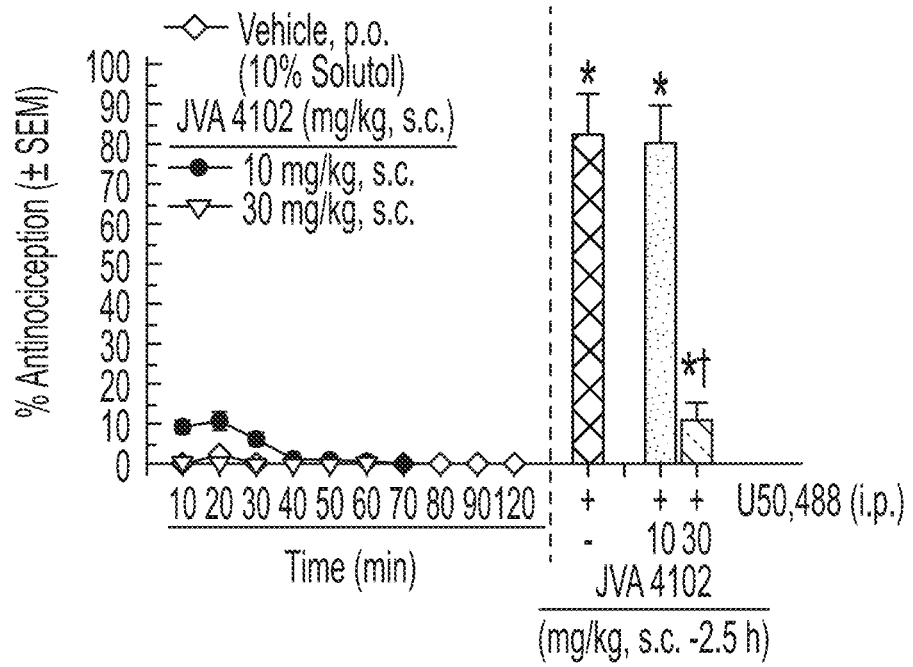
FIG. 9. shows the evaluation of cyclo[Phe-cis-D-Hyp(Gly)$^2$-Phe-D-Trp] (JVA 4102) in the mouse 55° C. warm water tail withdrawal assay. cyclo[Phe-cis-D-Hyp(Gly)$^2$-Phe-D-Trp] (JVA 4102) exhibited significant KOR antagonism after subcutaneous administration (30 mg/kg). Significantly different from * vehicle treated control and † U50,488 alone, p<0.5.

Student's t-tests and ANOVA with Tukey's HSD post hoc tests cane used to compare baseline and post-treatment tail-withdrawal latencies and to determine statistical significance for all tail-withdrawal data. Generally, independent experiments from several (e.g., seven to ten) mice are conducted and analyzed to increase the statistical significance of the tail-withdrawal data. Potency can be quantified by calculating ED$_{50}$ values with standard software known in the art (e.g., Prism 5.0 software, GraphPad Software, La Jolla, Calif., USA).

cyclo[Phe-cis-D-Hyp-Phe-D-Trp] (Compound G, JVA 4101) was evaluated using the above method by the treatment of the mice with cyclo[Phe-cis-D-Hyp-Phe-D-Trp] (Compound G, JVA 4101) 2.5 hours prior to receiving the KOR specific agonist, U50,488. The ED50 at 20 minutes was approximately 9 nmol after i.c.v. administration. Antagonist activity was observed at a dose of 3 nmol, with maximal antagonist activity achieved by 10 nmol (FIG. 3).

cyclo[Phe-cis-D-Hyp-Phe-D-Trp] (Compound G, JVA 4101) was orally administered to mice at a dose of 10 mg/kg. Antinociception was measured over a time course of 120 minutes. KOR antagonist activity was measured after treatment with cyclo[Phe-cis-D-Hyp-Phe-D-Trp] (Compound G, JVA 4101) for 2.5 hours followed by U50,488 administration. cyclo[Phe-cis-D-Hyp-Phe-D-Trp] (Compound G, JVA 4101) demonstrated agonist activity after oral administration. KOR antagonist activity was observed after oral administration, indicating blood brain barrier permeability (FIG. 5).

cyclo[Phe-cis-D-Hyp-Phe-D-Trp] (Compound G, JVA 4101) was evaluated in the mouse 55° C. warm water tail withdrawal assay following oral administration. cyclo[Phe-cis-D-Hyp-Phe-D-Trp] (Compound G, JVA 4101) exhibited significant antagonism at doses of 10 and 30 mg/kg p.o. of the KOR agonist U50,488 administered intraperitoneal (i.p.). Significantly different from * vehicle treated control and † U50,488 alone, p<0.5 (FIG. 6).

cyclo[Phe-cis-D-Hyp-Phe-D-Trp] (Compound G, JVA 4101) (10 mg/kg p.o.) significantly antagonized U50,488 administered centrally (i.c.v.). Significantly different from * vehicle treated control and † U50,488 alone, p<0.5 (FIG. 7).

cyclo[Phe-cis-D-Hyp(Gly) 2-Phe-D-Trp] (JVA 4102) exhibited significant antagonism of U50,488 administered i.p. at doses of 30 and 100 nmol i.c.v. * Significantly different from U50,488 alone, p<0.5. B. JVA 4102 also exhibited significant KOR antagonism after subcutaneous administration (30 mg/kg). Significantly different from * vehicle treated control and † U50,488 alone, p<0.5 (FIG. 8). cyclo[Phe-cis-D-Hyp(Gly)$^2$-Phe-D-Trp](JVA 4102) exhibited significant KOR antagonism after subcutaneous administration (30 mg/kg). Significantly different from * vehicle treated control and † U50,488 alone, p<0.5 (FIG. 9).

Example 11: Cocaine Conditioned Place Preference (CPP), Extinction, and Reinstatement Mice can be conditioned based on previously established biased cocaine CPP paradigm as published [Carey, A. N., Borozny, K., Aldrich, J. V., and McLaughlin, J. P., (2007) Reinstatement of cocaine place-conditioning prevented by the peptide kappa-opioid receptor antagonist, Arodyn Eur J Pharmacol 569, 84-89; Aldrich, J. V., Patkar, K. A., McLaughlin, J. P. (2009) Zyklophin, a systemically active selective kappa opioid receptor peptide antagonist with short duration of action Proc Natl Acad Sci USA 106, 18396-18401]. Briefly, individual mice are allowed to run freely between the three linear compartments comprising the apparatus for the 30 min testing period. Time spent in each compartment is measured, and the initial compartment preference of each mouse is determined. The mice are subsequently place-conditioned immediately following administration of cocaine (10 mg-kg$^{-1}$, s.c.) and confined to the appropriate outer compartment starting on day 2. Place-conditioning in the opposite outer compartment initially preferred by the mouse is performed daily with vehicle (0.9% saline, 0.3 mL per 30 g body weight, s.c.) 4 h after the cocaine conditioning. This place-conditioning cycle is repeated once each day on days 3-5, and on day 6 the animals are tested for a final place preference. Data are exhibited as the difference in time spent on cocaine- and vehicle-paired sides. By convention, the initial bias generates a negative value, and a positive value represents a conditioned preference for the cocaine-paired side. Conditioned place aversion, where the animals avoid the drug-paired compartment and spend a significantly greater time in the saline-paired compartment than initially demonstrated, may or may not be detected in this study under any conditions.

Preference tests are completed twice weekly for 30 min until extinction is established. Extinction is defined as a statistically significant decrease in the time spent in the cocaine-paired compartment during the extinction trial as compared with the post-conditioning response after the initial 4 days of conditioning [Szumlinski, K. K., Price, K. L., Frys, K. A., and Middaugh L. D. (2002) Unconditioned and conditioned factors contribute to the 'reinstatement' of cocaine place conditioning following extinction in C57Bl/6 mice Behav Brain Res 136, 151-160; Brabant, C., Quertemont, E., and Tirelli, E. (2005) Influence of the dose and number of druc-context pairings on the magnitude and the long-lasting retention of cocaine-induced condition place preference in C57Bl/6 mice Psychopharmacology (Berl) 180, 33-40]. Generally, CCP responses show extinction around 3 weeks for the C57Bl/6 strain of mice.

Following the demonstration of extinction, reinstatement of cocaine CPP can be examined after either exposure to forced swim stress (see Example 12) or an additional cycle of cocaine place-conditioning as described above. Briefly, half the tested mice are pretreated with either vehicle (i.c.v.) or the compound of the invention (i.c.v.) daily 20 min prior to forced swimming (see Example 12). Additional mice are also administered vehicle (i.c.v.) or the compound of the invention (i.c.v.) on days 28 and 29, and 20 min after the final administration of vehicle or the compound of the invention on day 29 an additional session of cocaine place conditioning is performed. On the day following the completion of stress exposure or cocaine place-conditioning, mice are tested for place preference (as described above).

Data for CPP experiments can be analyzed with ANOVA using standard software known in the art (e.g., SPSS 14.0 statistical package, Chicago, Ill., USA). Analyses examined the main effect of CPP phase (e.g., postconditioning, week of preference test, reinstatement) and the interaction of drug pretreatment (the compound of the invention or vehicle) under the appropriate reinstatement condition (stress or cocaine exposure). Significant effects can be further analyzed using Tukey's HSD post hoc test.

Example 12: Forced Swim Stress

To produce stress-induced reinstatement of cocaine CPP, a 2 day forced swim stress protocol can be used according to previously published methods [McLaughlin, J. P., Marton-Popovici, M., and Chavkin, C. (2003) Kappa opioid receptor antagonism and prodynorphin gene distribution block stress-induced behavioral response J Neurosci 23, 5674-5683; Carey, A. N., Borozny, K., Aldrich, J. V., and McLaughlin, J. P., (2007) Reinstatement of cocaine place-conditioning prevented by the peptide kappa-opioid receptor antagonist, Arodyn Eur J Pharmacol 569, 84-89]. Briefly, for each of the 2 days, mice are pretreated with either vehicle or the compound of the invention 20 min before exposure to forced swim stress. The day after the final exposure to swim stress, the place preference response of each mouse is tested to evaluate reinstatement of the extinguished cocaine CPP.

Example 13: Opioid Receptor Specificity

Figure 4:
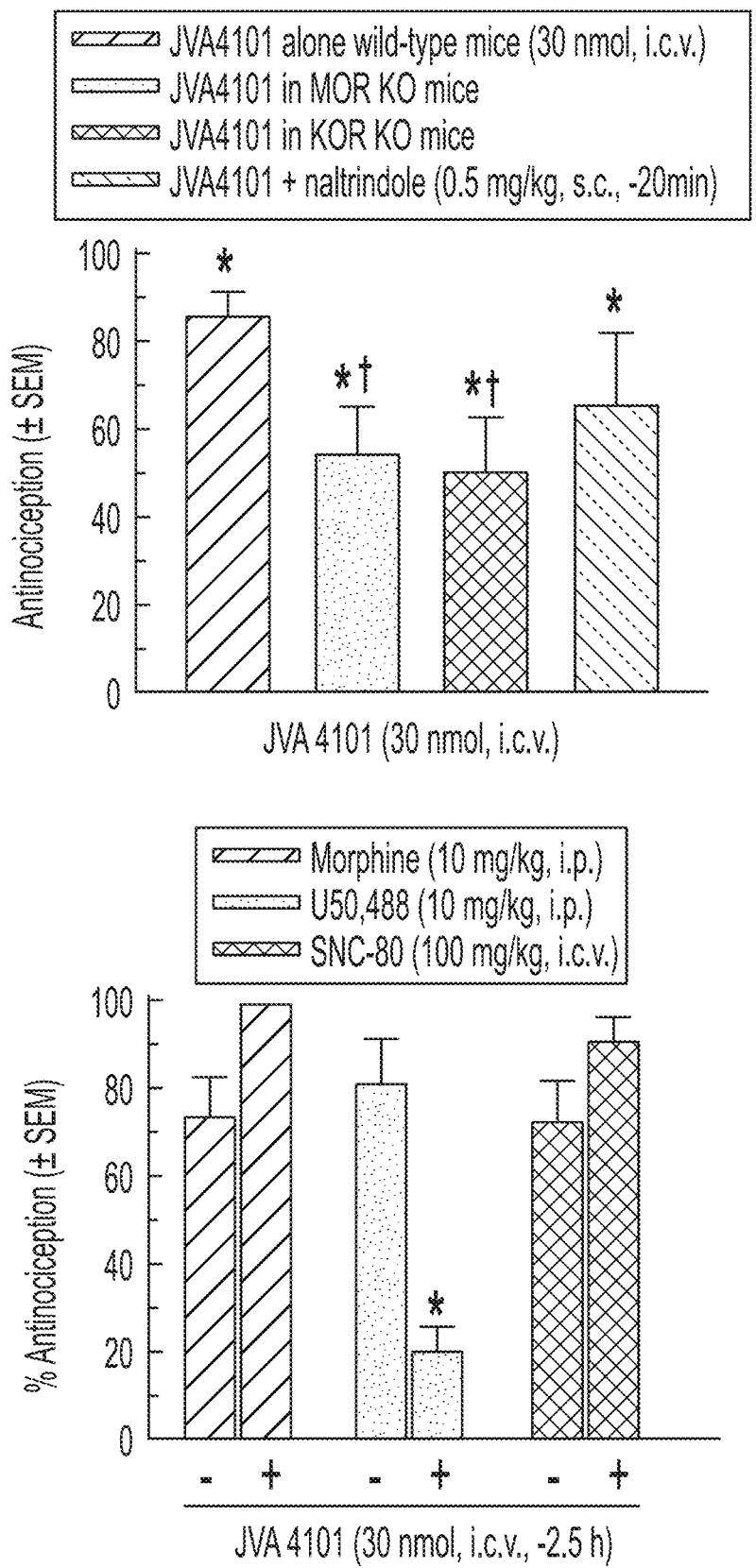
FIG. 4. shows opioid receptor specificity. To determine the opioid receptor specificity of the hydroxyproline derivative, agonist activity was measured in MOR or KOR knockout mice or in mice receiving a DOR specific antagonist. Antagonist activity was measured in mice receiving MOR, KOR, or DOR specific agonists. The hydroxyproline derivative displayed MOR and KOR agonist activity. KOR selective antagonist activity was observed.

The opioid receptor specificity of compounds of the invention can be determined by measuring the agonist activity of the compound of the invention in MOR or KOR knockout mice or in mice receiving a DOR specific agonists. Opioid receptor agonists are known in the art. The antagonist activity of compounds of the invention can be measured in mice receiving DOR, KOR, or MOR specific agonists. The 55° C. warm-water tail-withdrawal test (Example 10) can be used to determine opioid receptor specificity in mice carrying these gene knockouts.

cyclo[Phe-cis-D-Hyp-Phe-D-Trp] (Compound G, JVA 4101) displayed MOR and KOR agonist activity with KOR selective antagonist activity being observed (FIG. 4).

Figure 10:
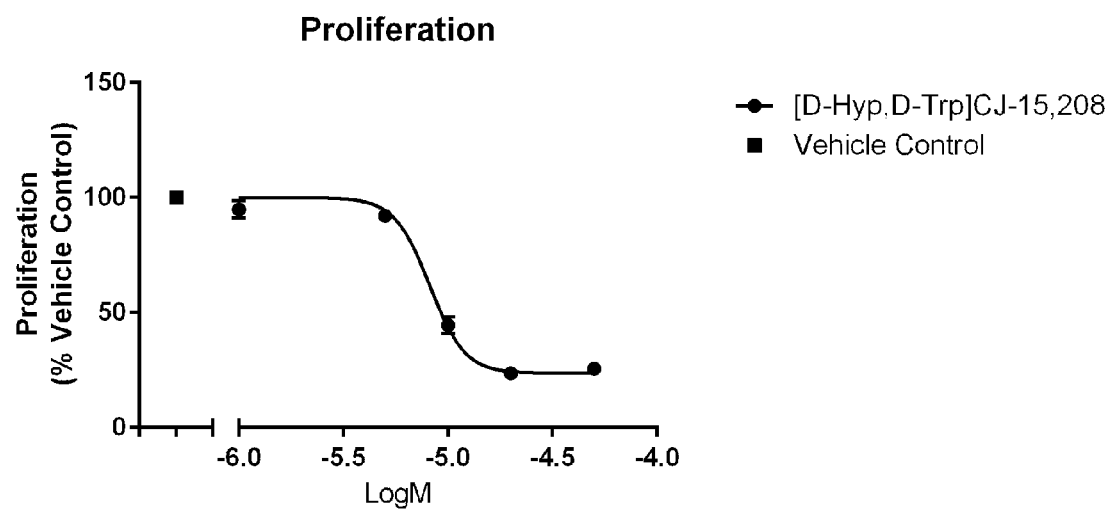
FIG. 10. shows the inhibition of the proliferation of PC-3 prostate cancer cells by cyclo[Phe-cis-D-Hyp-Phe-D-Trp] (Compound G, JVA 4101). The cells were treated with the compound or vehicle (0.5% DMSO) for 48 hours, and total cell counts measured using the Muse Cell Analyzer (Millipore). Data represents the average of three independent experiments, where error bars represent SEM.

Example 14: Cell Proliferation Assay cyclo[Phe-cis-D-Hyp-Phe-D-Trp] (Compound G, JVA 4101) inhibited the proliferation of PC-3 prostate cancer cells by cyclo[Phe-cis-D-Hyp-Phe-D-Trp] (Compound G, JVA 4101). The cells were treated with the compound or vehicle (0.5% DMSO) for 48 hours, and total cell counts measured using the Muse Cell Analyzer (Millipore). Data represents the average of three independent experiments, where error bars represent SEM (FIG. 10).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of formula (1), or a salt, solvate, hydrate or prodrug thereof:

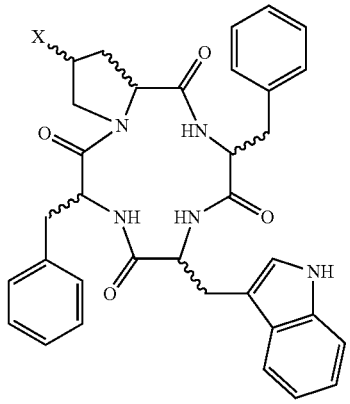

(1)

wherein, each X is independently —OH or —NH$_2$.

2. The compound of claim 1 of formula (2), or a salt, solvate, hydrate or prodrug thereof:

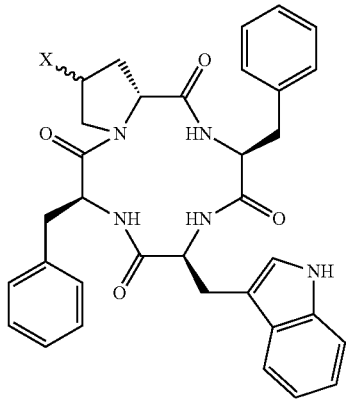

(2)

wherein, each X is independently —OH or —NH$_2$.

3. The compound of claim 1 of formula (3), or a salt, solvate, hydrate or prodrug thereof:

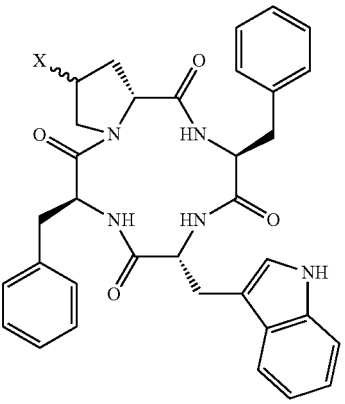

(3)

wherein, each X is independently —OH or —NH$_2$.

4. The compound of claim 1 of formula (4), or a salt, solvate, hydrate or prodrug thereof:

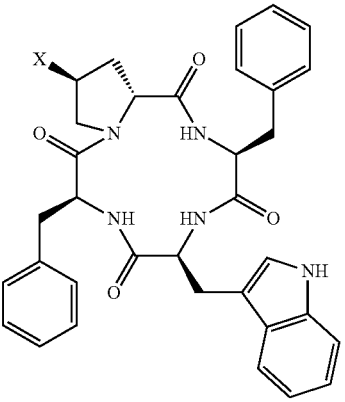

(4)

wherein, each X is independently —OH or —NH$_2$.

5. The compound of claim 1 of formula (5), or a salt, solvate, hydrate or prodrug thereof:

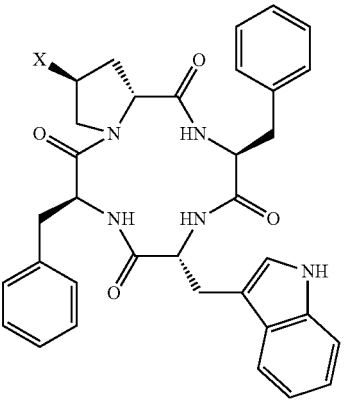

(5)

wherein, each X is independently —OH or —NH$_2$.

6. The compound of claim 1 of formula (6), or a salt, solvate, hydrate or prodrug thereof:
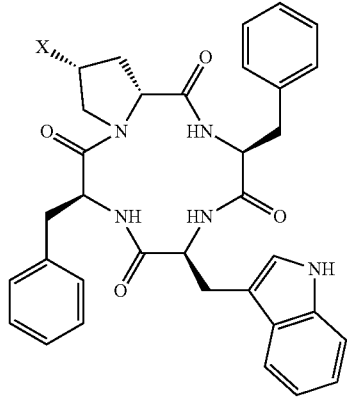
(6)
wherein, each X is independently —OH or —NH₂.
7. The compound of claim 1 of formula (7), or a salt, solvate, hydrate or prodrug thereof:
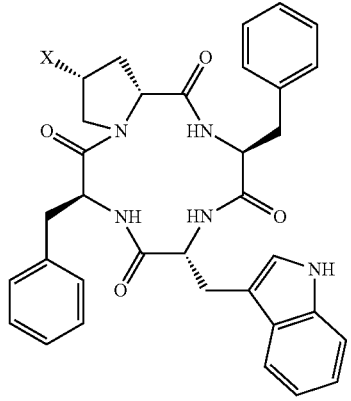
(7)
wherein, each X is independently —OH or —NH₂.
8. The compound of claim 1, wherein the compound is:
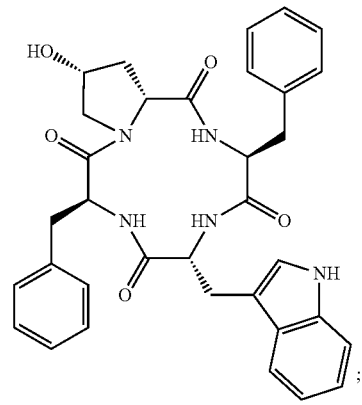
;
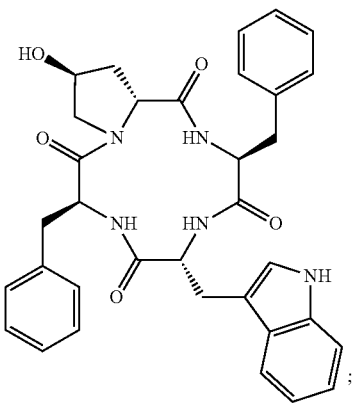
;
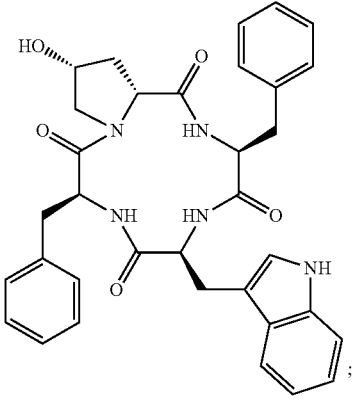
;
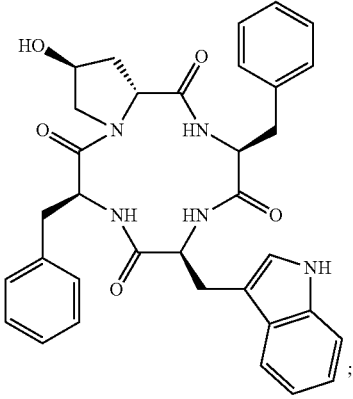
;
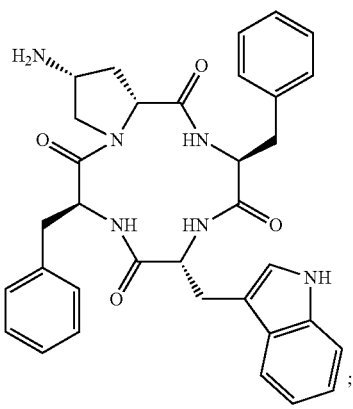
;

-continued

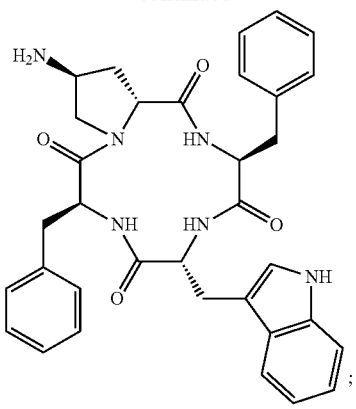

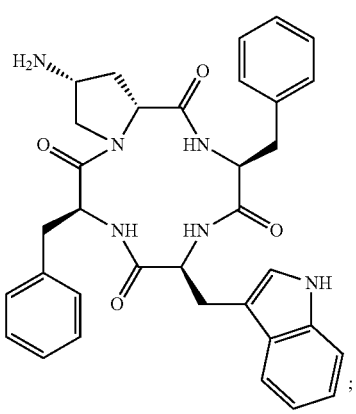

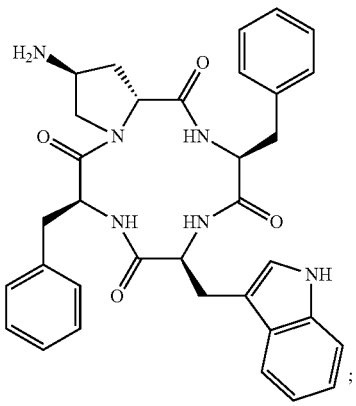

or a salt, solvate, hydrate, or prodrug thereof.

9. A compound of formula (8), or a salt, solvate, hydrate or prodrug thereof:

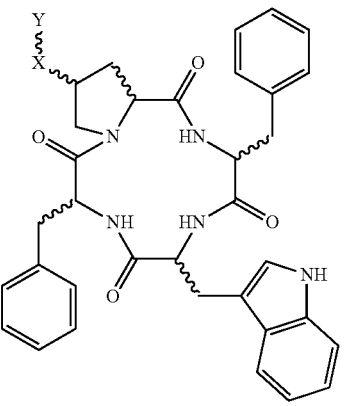

wherein,
  each X is independently —O or —NH;
  each Y is independently —COCH$_3$, —CO(CH$_2$)$_n$R$^1$, —COCH$_2$(OCH$_2$CH$_2$)$_m$R$^1$, or —R$^2$;
  each R$^1$ is independently NHR$^2$, N$_3$, or C$_{2-3}$ alkynyl;
  each R$^2$ is independently H or

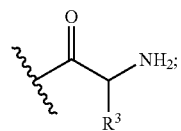

each R$^3$ is independently an amino acid side chain;
  each m is independently 0, 1, 2, 3, 4, 5, 6, 7, 8, 9, or 10; and
  each n is independently 0, 1, 2, 3, 4, 5, 6, 7, 8, 9, or 10.

10. The compound of claim 9, according to formula (9) or (10), or a salt, solvate, hydrate or prodrug thereof:

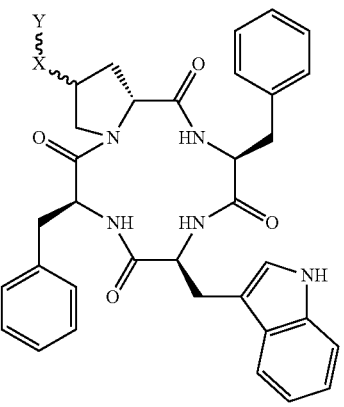

or

-continued (10)

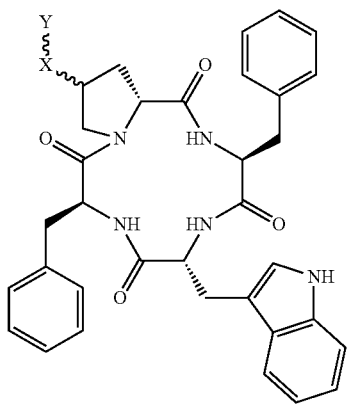

wherein, each X is independently —O or —NH;

each Y is independently —COCH$_3$, —CO(CH$_2$)$_n$R$^1$, —COCH$_2$(OCH$_2$CH$_2$)$_m$R$^1$, or —R$^2$;

each R$^1$ is independently NHR$^2$, N$_3$, or C$_{2-3}$ alkynyl;

each R$^2$ is independently H or

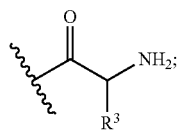

each R$^3$ is independently an amino acid side chain;

each m is independently 0, 1, 2, 3, 4, 5, 6, 7, 8, 9, or 10; and each n is independently 0, 1, 2, 3, 4, 5, 6, 7, 8, 9, or 10.

11. The compound of claim 9, according to formula (11) or (12), or a salt, solvate, hydrate or prodrug thereof:

(11)

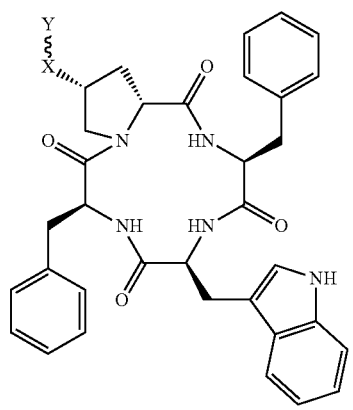

or

-continued (12)

wherein, each X is independently —O or —NH;

each Y is independently —COCH$_3$, —CO(CH$_2$)$_n$R$^1$, —COCH$_2$(OCH$_2$CH$_2$)$_m$R$^1$, or —R$^2$;

each R$^1$ is independently NHR$^2$, N$_3$, or C$_{2-3}$ alkynyl;

each R$^2$ is independently H or

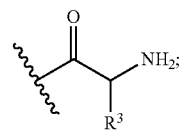

each R$^3$ is independently an amino acid side chain;

each m is independently 0, 1, 2, 3, 4, 5, 6, 7, 8, 9, or 10; and each n is independently 0, 1, 2, 3, 4, 5, 6, 7, 8, 9, or 10.

12. The compound of claim 9, according to formula (13) or (14), or a salt, solvate, hydrate or prodrug thereof:

(13)

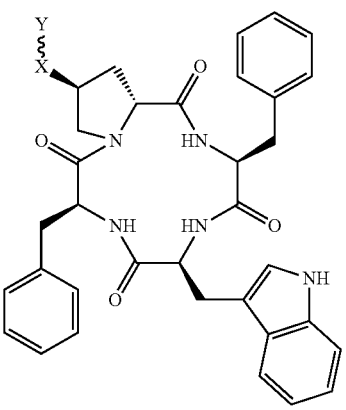

or (14)

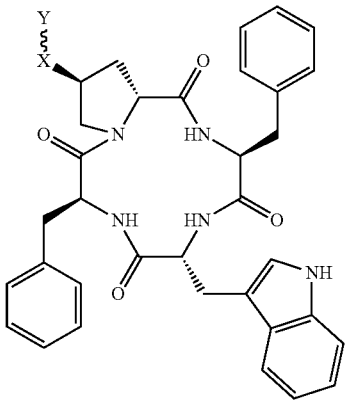

wherein,
    each X is independently —O or —NH;
    each Y is independently —COCH$_3$, —CO(CH$_2$)$_n$R$^1$, —COCH$_2$(OCH$_2$CH$_2$)$_m$R$^1$, or —R$^2$;
    each R$^1$ is independently NHR$^2$, N$_3$, or C$_{2-3}$ alkynyl;
    each R$^2$ is independently H or

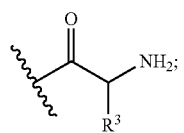

each R$^3$ is independently an amino acid side chain;
each m is independently 0, 1, 2, 3, 4, 5, 6, 7, 8, 9, or 10; and
each n is independently 0, 1, 2, 3, 4, 5, 6, 7, 8, 9, or 10.

13. The compound of claim 9, or a salt, solvate, hydrate or prodrug thereof, wherein the compound is:

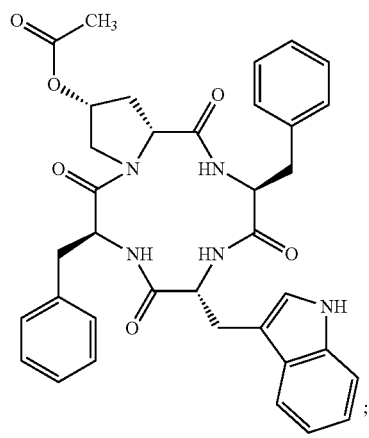

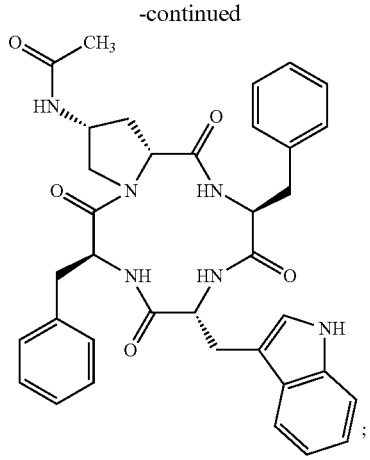

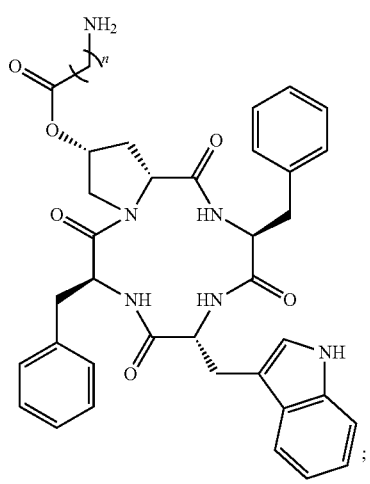

141
-continued
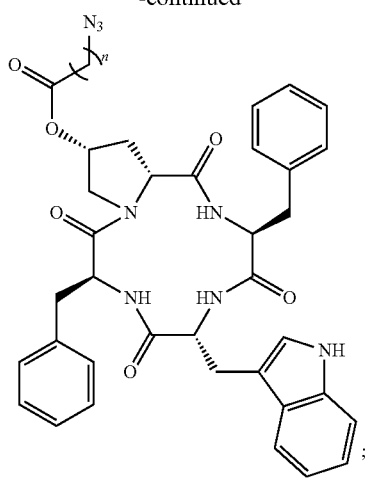
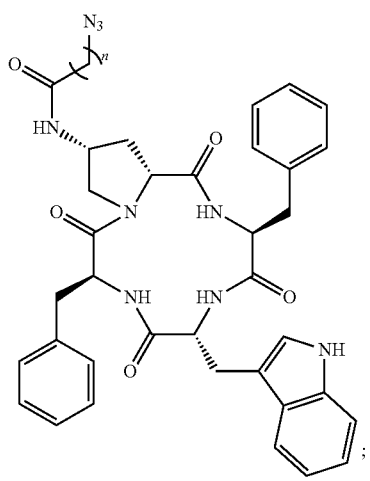
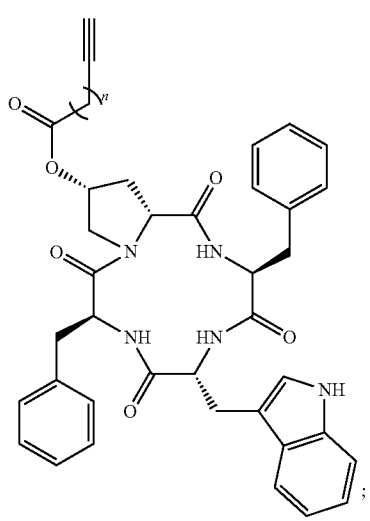
142
-continued
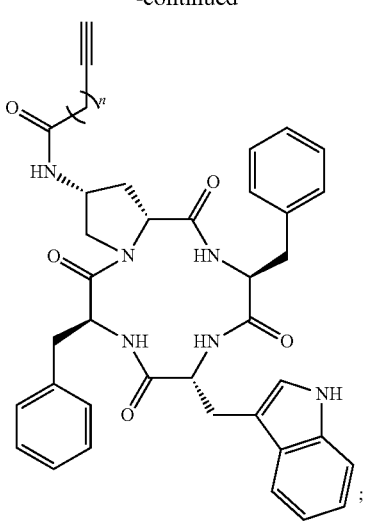
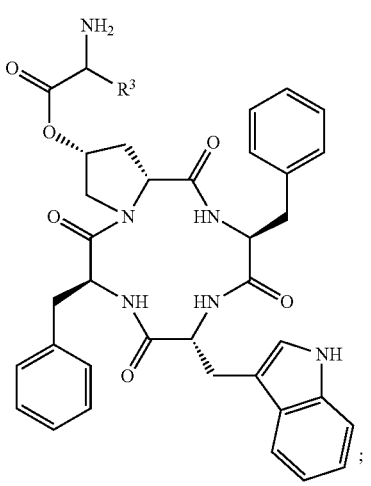
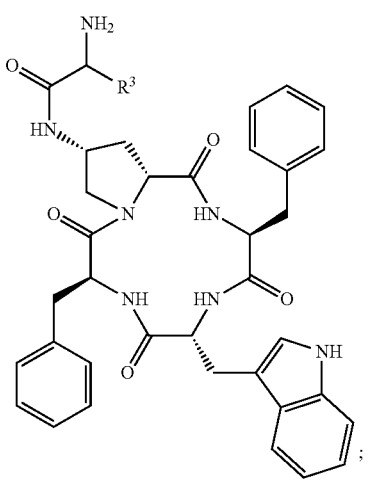

143
-continued
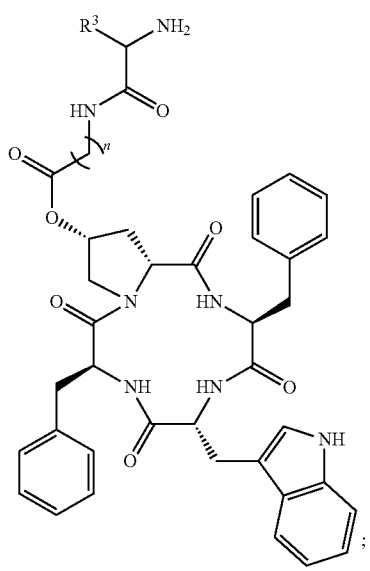
;
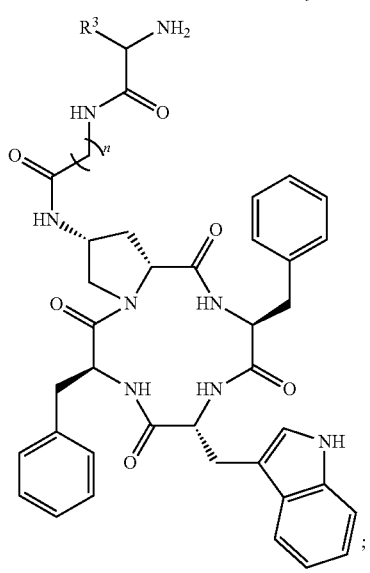
;
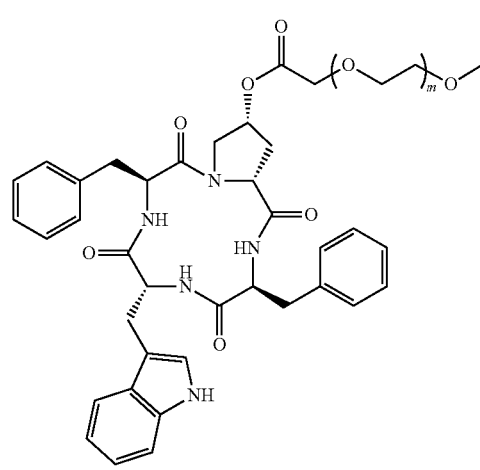
144
-continued
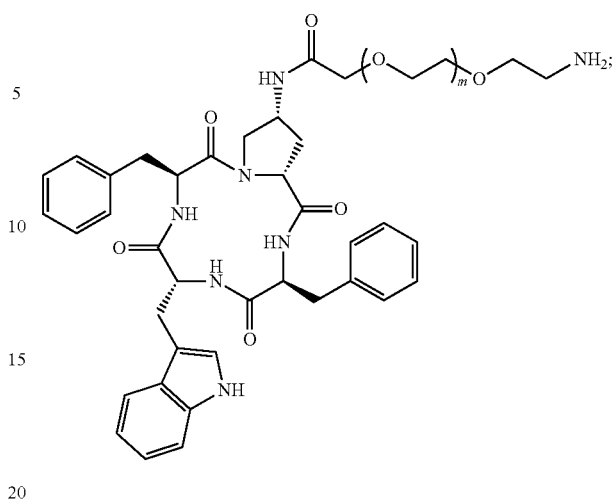
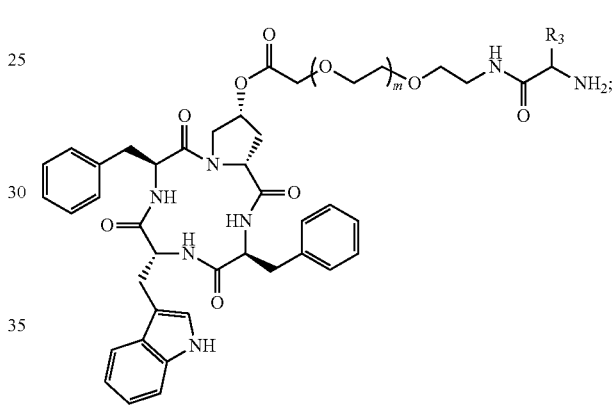
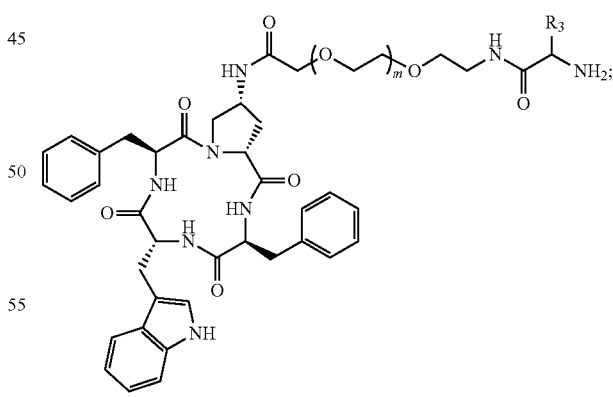
wherein,
  each $R^3$ is independently an amino acid side chain;
  each m is independently 0, 1, 2, 3, 4, 5, 6, 7, 8, 9, or 10; and
  each n is independently 0, 1, 2, 3, 4, 5, 6, 7, 8, 9, or 10;
  or a salt, solvate, hydrate or prodrug thereof.

14. The compound of claim 9, wherein the compound is:

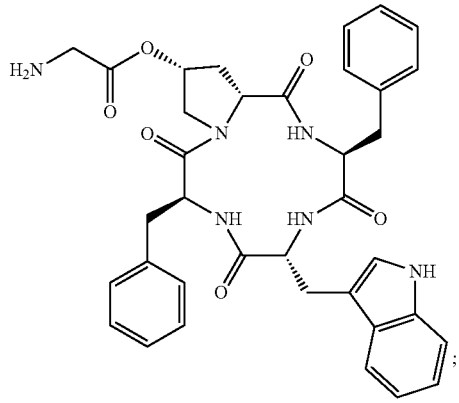

cyclo[Phe-cis-D-Hyp(Gly)²-Phe-D-Trp] (JVA 4102)

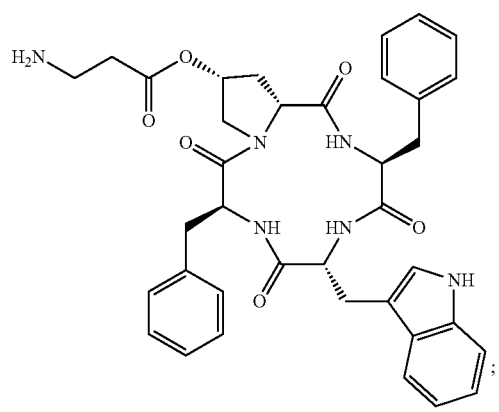

cyclo[Phe-cis-D-Hyp(β-Ala)²-Phe-D-Trp]

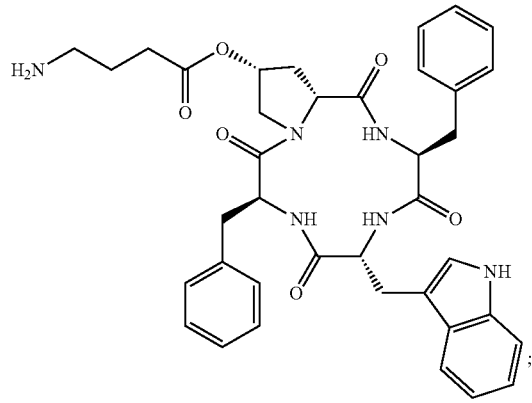

cyclo[Phe-cis-D-Hyp(γ-aminoisobutyric acid)²-Phe-D-Trp]

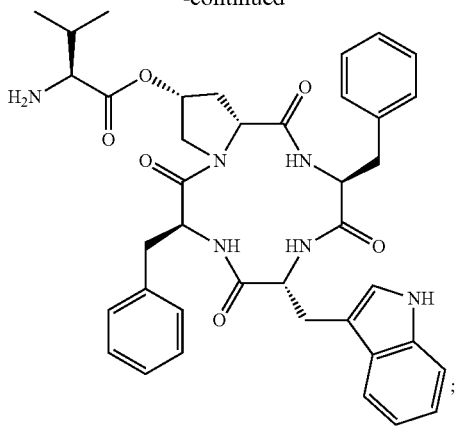

cyclo[Phe-cis-D-Hyp(Val)²-Phe-D-Trp]

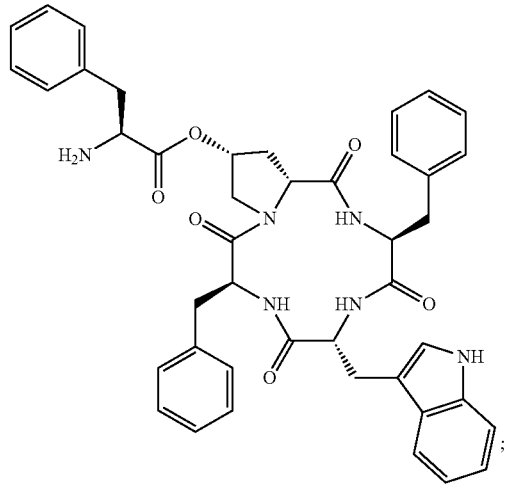

cyclo[Phe-cis-D-Hyp(Phe)²-Phe-D-Trp]

or a salt, solvate, hydrate or prodrug thereof.

15. A compound of formula (15), or a salt, solvate, hydrate or prodrug thereof:

(15)

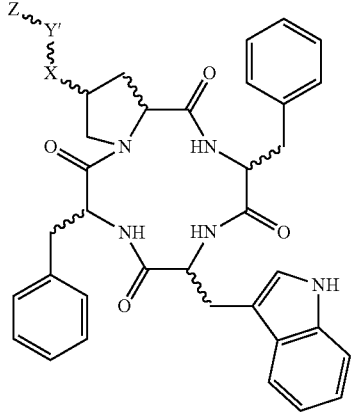

wherein,
each X is independently —O or —NH;
each Y' is independently —CO(CH$_2$)$_n$NHZ or —COCH$_2$(OCH$_2$CH$_2$)$_m$NHZ;

each Z is independently
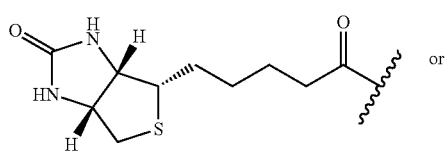 or
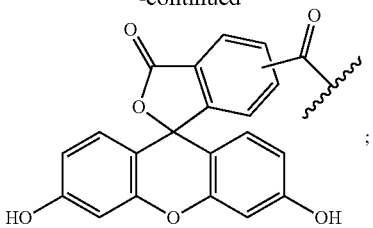
each m is independently 0, 1, 2, 3, 4, 5, 6, 7, 8, 9, or 10; and
each n is independently 0, 1, 2, 3, 4, 5, 6, 7, 8, 9, or 10.
16. The compound of claim 15, or a salt, solvate, hydrate or prodrug thereof, wherein the compound is:
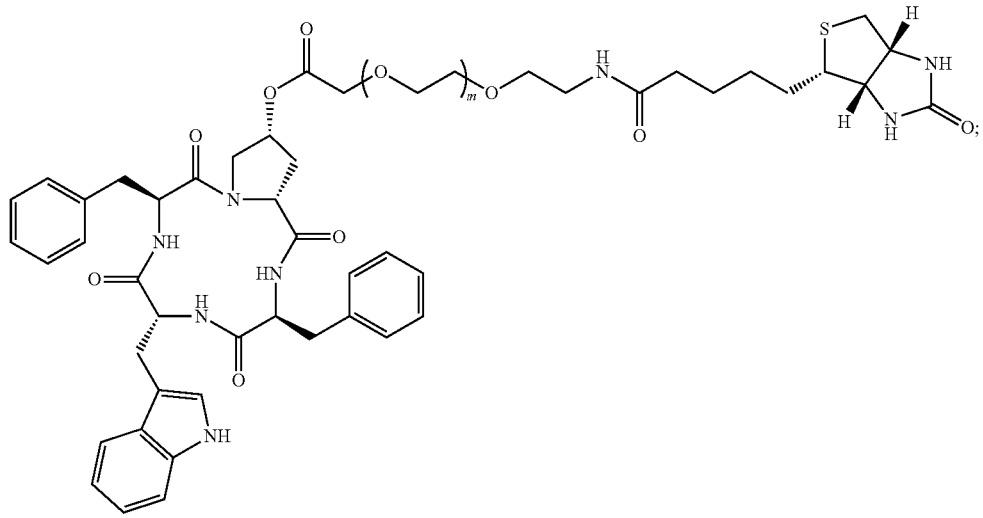
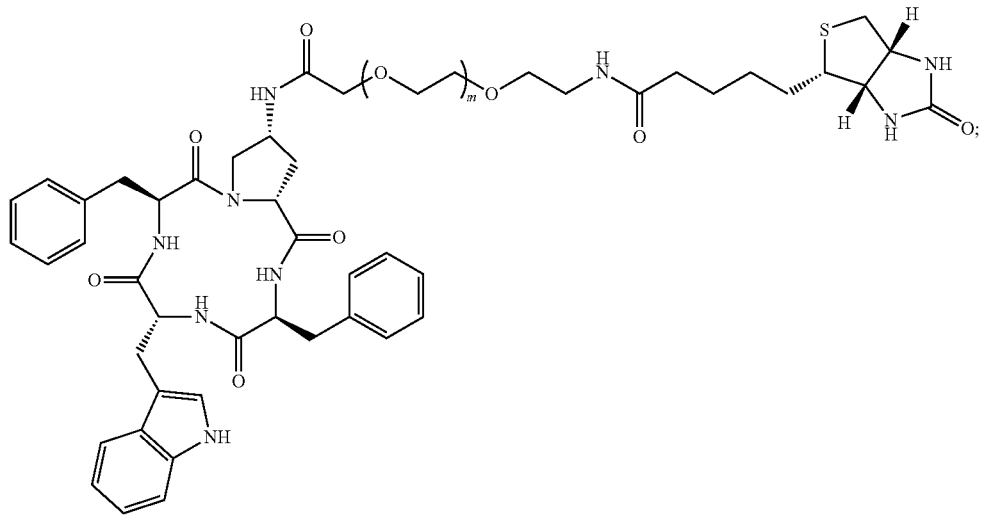

-continued
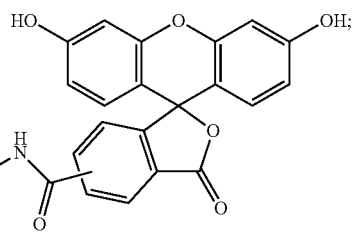
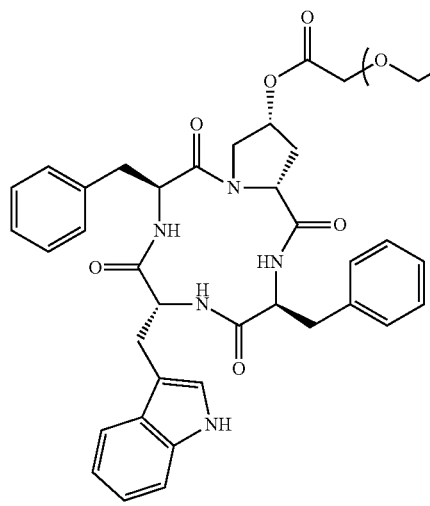
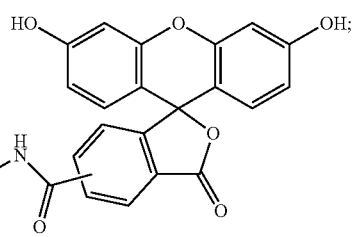
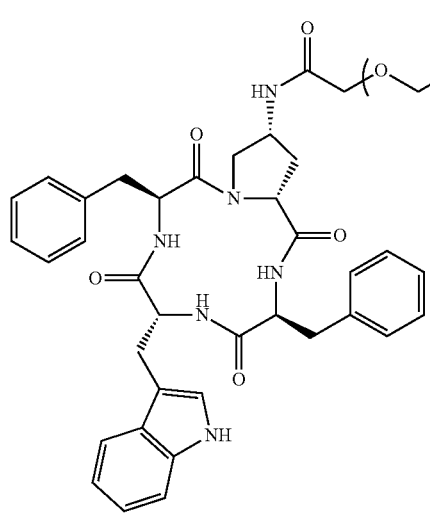
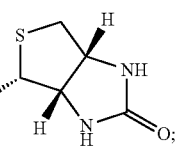
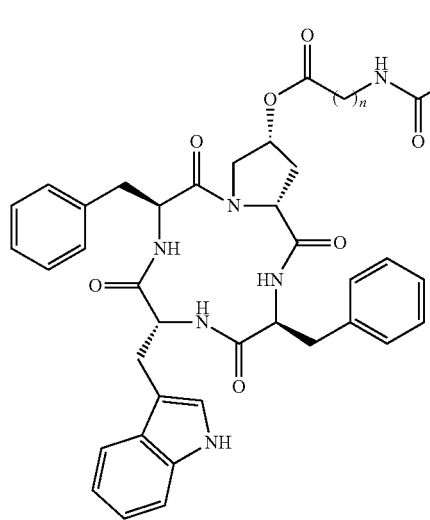

-continued
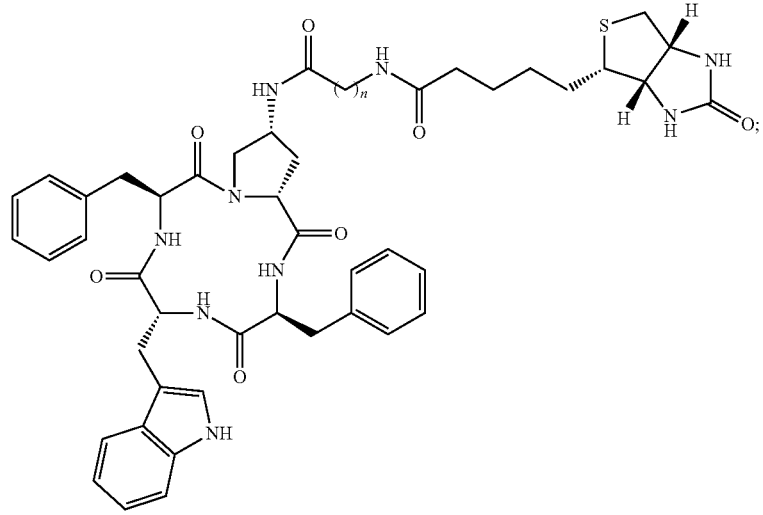
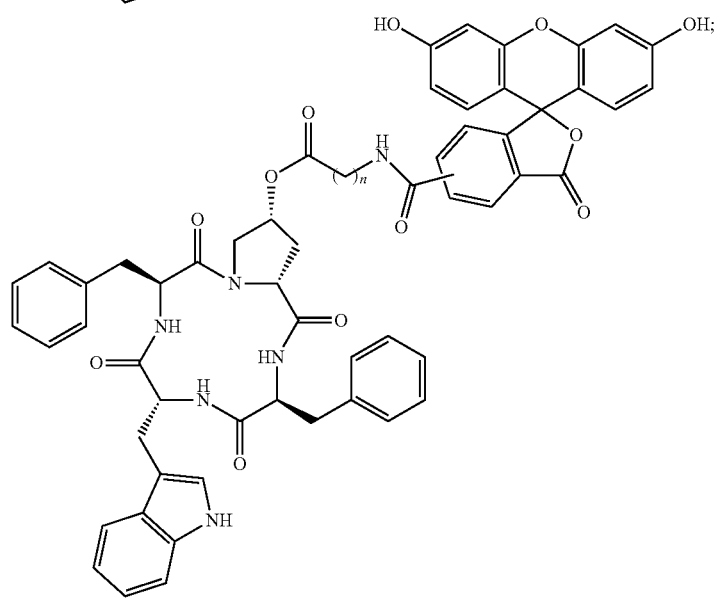
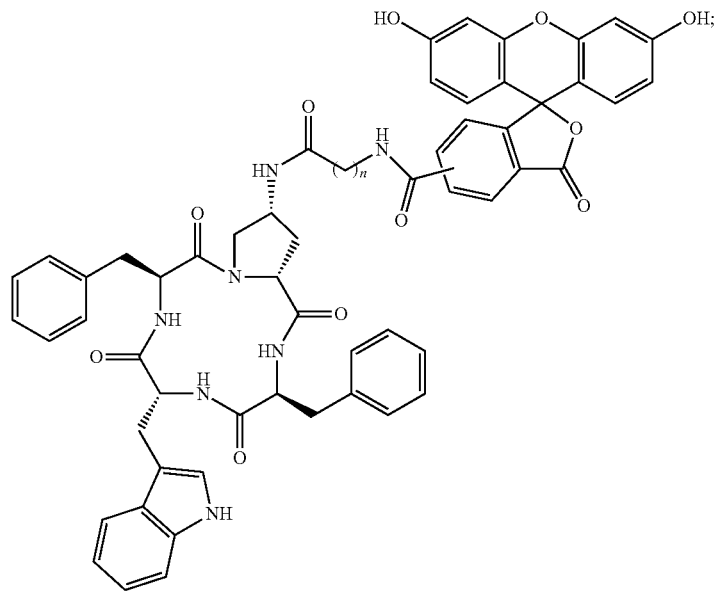

wherein,
each m is independently 0, 1, 2, 3, 4, 5, 6, 7, 8, 9, or 10; and
each n is independently 0, 1, 2, 3, 4, 5, 6, 7, 8, 9, or 10.

17. A method of treating a subject with a neurological disorder comprising administering to the subject in need thereof a therapeutically effective amount of a compound of claim 1, or a salt, solvate, hydrate or prodrug thereof, wherein the neurological disorder is addiction.

18. The method of claim 17, wherein the addiction is a drug addiction.

19. The method of claim 18, wherein the drug addiction is a cocaine addiction.

20. A method of treating a subject with a painful condition comprising administering to the subject in need thereof a therapeutically effective amount of a compound of claim 1, or a salt, solvate, hydrate or prodrug thereof.

21. A method of treating a subject with an opioid receptor mediated disorder comprising administering to the subject in need thereof a therapeutically effective amount of a compound of claim 1, or a salt, solvate, hydrate or prodrug thereof.

22. A pharmaceutical composition comprising a compound of claim 1, or a salt thereof, and a pharmaceutically acceptable carrier.

23. A method of treating a subject with a psychiatric disorder comprising administering to the subject in need thereof a therapeutically effective amount of a compound of claim 1, or a salt, solvate, hydrate or prodrug thereof, wherein the psychiatric disorder is an opioid receptor mediated psychiatric disorder.

24. The method of claim 23, wherein the opioid receptor mediated psychiatric disorder is a mood disorder.

25. The method of claim 23, wherein the opioid receptor mediated psychiatric disorder is a substance abuse disorder.

26. The method of claim 25, wherein the substance abuse disorder is a cocaine abuse disorder.

\* \* \* \* \*